(12) United States Patent
Korzekwa et al.

(10) Patent No.: US 6,643,591 B1
(45) Date of Patent: Nov. 4, 2003

(54) USE OF COMPUTATIONAL AND EXPERIMENTAL DATA TO MODEL ORGANIC COMPOUND REACTIVITY IN CYTOCHROME P450 MEDIATED REACTIONS AND TO OPTIMIZE THE DESIGN OF PHARMACEUTICALS

(75) Inventors: Kenneth R. Korzekwa, Mountain View, CA (US); Jeffrey P. Jones, Pullman, WA (US); Lee Ann Higgins, Seattle, WA (US)

(73) Assignees: University of Pittsburgh, Pittsburgh, PA (US); University of Rochester, Rochester, NY (US)

( * ) Notice: Subject to any disclaimer, the term of this patent is extended or adjusted under 35 U.S.C. 154(b) by 0 days.

(21) Appl. No.: 09/368,511

(22) Filed: Aug. 5, 1999

Related U.S. Application Data
(60) Provisional application No. 60/095,460, filed on Aug. 5, 1998.

(51) Int. Cl.$^7$ ............................ G06N 7/00; G06F 17/12; C12Q 1/26

(52) U.S. Cl. ............................... 702/27; 702/30; 703/2; 435/25

(58) Field of Search ........................ 702/27, 30; 703/2; 435/25; 436/135, 136

(56) References Cited

FOREIGN PATENT DOCUMENTS
WO        WO 95/18969         7/1995

OTHER PUBLICATIONS

Jones et al. The separation of the intramolecular isotope effect for the cytochrome P–450 catalyzed hydroxylation of n–octane into its primary and secondary components. J. Am. Chem. Soc. (1987) vol. 109 (7), pp. 2171–2173.*

Jones et al. The binding and regioselectivity of reaction of (R)– and (S)–nicotine with cytochrome P–450cam: Parallel experimental and theoretical studies. J. Am. Chem. Soc. (1993) vol. 115, pp. 381–387.*

Korzekwa et al. Electronic models for cytochrom P450 oxidations. Adv. Exp. Med. Biol. (1996) vol. 387, pp. 361–369.*

International Search Report for PCT/US99/17713 dated Nov. 11, 1999.

Hequn, Y., et al., "Designing safer chemicals: Predicting the rates of metabolism of halogenated alkanes", Proc. Natl. Acad. Scie. USA 92(24):11076–11080 (Nov. 1995).

Abstract No. XP–002122407, P84 to Johnson et al., "Automated Modeling Predicts Active Site Geometries Consistent with the Regiospecificity of P450s 2C3v and 2C5 for Progesterone Hydroxylation," FASEB Journal 11(9):P785 (1997).

Bradford, M.M., et al., "A Rapid and Sensitive Method for the Quantitation of Microgram Quantities of Protein Utilizing the Principle of Protein–Dye Binding," Anal. Biochem., (1976) 72:248–54.

Burka, L. T., et al., "Mechanism of Cytochrome P–450 Catalysis. Mechanism of N–Dealkylation and Amine Oxide Deoxygenation," J. Am. Chem. Soc., (1985) 107:2549–51.

Burka, L. T., et al., "Mechanisms of Hydroxylation by Cytochrome P–450: Metabolism of Monohalobenzenes by Phenobarbital–Induced Microsomes," Proc. Natl. Acad. Sci. USA (1983) 80:6680–4.

Cleland, W.W., "Partition Analysis and the Concept of Net Rate Constants as Tools in Enzyme Kinetics," Biochemistry, (1975) 14(14):3220–4.

Cleland, W.W., "The Use of Isotope Effects to Determine Transistion–State Structure for Enzymic Reactions," Methods Enzymol., (1982) 87:625–41.

Cupp–Vickery, J.R. et al., "Structure of Cytochrome P450eryF Involved in Erythromycin Biosynthesis," Structural Biology, (1995) 2(2):144–53.

Dinnocenzo, J.P., et al., "On Isotope Effects for the Cytochrome P–450 Oxidation of Substituted N,N–Dimethylanilines," J. Am. Chem. Soc., (1993) 115:7111–6.

Franchetti, P., et al., "Furanfurin and Thiophenfurin: Two Novel Tiazofurin Analogues. Synthesis, Structure, Antitumor Activity, and Interactions with Inosine Monophosphate Dehydrogenase," J. Med. Chem., (1995) 38:3829–37.

Gonzalez, F. J., et al., "Human Cytochromes P450: Problems and Prospects," TIPS Reviews, (1992) 13:346–52.

Gonzalez, F.J., et al., "Expression of Mammalian Cytochrome P450 Using Vaccinia Virus," Methods Enzymol., (1991) 206:85–92.

Grogan, J., et al., "Modeling Cyanide Release from Nitriles: Prediction of Cytochrome P450 Mediated Acute Nitrile Toxicity," Chem. Res. Toxicol., (1992) 5(4):548–52.

Groves, J. T., et al., "Aliphatic Hydroxylation by Highly Purified Liver Microsomal Cytochrome P–450. Evidence for a Carbon Radical Intermediate," Biochemical & Biophysical Research Communications (1978) 81(1):154–60.

(List continued on next page.)

*Primary Examiner*—Marjorie Moran
(74) *Attorney, Agent, or Firm*—Beyer, Weaver & Thomas, LLP

(57) ABSTRACT

The present invention is directed to the use of computational and other experimental data in the design of new pharmaceuticals, and in predicting the metabolism and toxicological profiles thereof. Computational and other information is used to further understand drug metabolism and toxicology, particulary in relation to monooxygenase enzymes, such as those of the CYP system, that are involved in drug metabolism. Information derived according to the practice of the invention is useful in determining the clearance or half-life of drugs, and the nature and toxicity of byproducts resulting from their metabolism. The invention provides novel and powerful new approaches to drug design.

40 Claims, 10 Drawing Sheets

OTHER PUBLICATIONS

Groves, J.T., et al., "Hydroxylation by Cytochrome P–450 and Metalloporphyrin Models. Evidence for Allylic Rearrangement," J. Am. Chem. Soc., (1984) 106: 2177–81.

Guengerich, F. P., et al., "Role of Human Cytochrome P–450 IIE1 in the Oxidation of Many Low Molecular Weight Cancer Suspects," Chem. Res. Toxicol., (1991) 4:168–79.

Guengerich, F. P., et al., "Evidence for a 1–Electron Oxidation Mechanism in N–Dealkylation of N,N–Dialkylanilines by Cytochrome P450 2B1," J. Biol. Chem., 271(44):27321–9 (Nov. 1996).

Hammond, G. S., "A Correlation of Reaction Rates," J. Am. Chem. Soc., (1955) 77(2):334–40.

Hanzlik, R.P., et al., "Intramolecular Kinetic Deuterium Isotope Effects on Microsomal Hydroxylation and Chemical Chlorination of Toluene–$\alpha$–$d_1$ and Toluene–$\alpha,\alpha$–$d_2$," J. Am. Chem. Soc., (1985) 107:7164–7.

Harada, N., et al., "Kinetic Isotope Effects on Cytochrome P–450–Catalyzed Oxidation Reaction," J. Biol. Chem., (1984) 259(5):3005–10.

Hasemann, C.A., et al., "Structure and Function of Cytochromes P450: A Comparative Analysis of Three Crystal Structures," Structure, (1995) 3(1):41–62.

Hasemann, C.A., et al., "Crystal Structure and Refinement of Cytochrome P450$_{terp}$ at 2•3 Å Resolution," J. Mol. Biol., (1994) 236:1169–85.

Héberger, K., "Linear Free Energy Relationships in Radical Reactions. II. Hydrogen Abstraction From Substituted Toluenes by TERT–Butyl, TERT–Butoxyl and Tert–Butylperoxyl Radicals," J. Phys. Org. Chem., (1994) 7:244–50.

Hermes, J.D., et al., "Use of Multiple Isotope Effects to Determine Enzyme Mechanisms and Intrinsic Isotope Effects. Malic Enzyme and Glucose–6–phosphate Dehydrogenase," Biochemistry, (1982) 21:5106–1428.

Hjelmeland, L. M., et al., "Intramolecular Determination of Primary Kinetic Isotope Effects in Hydroxylations Catalyzed by Cytochrome P–450," Biochem. Biophys. Res. Commun., (1977) 76:541–9.

Jones, J. et al., "Predicting The Rates And Regioselectivity of Reactions Mediated By The P450 Superfamily," Methods in Enzymology, (1996) 272:326–35.

Jones, J.P., et al., "Stereospecific Activation of the Procarcinogen Benzo[a]pyrene: A Probe for the Active Sites of the Cytochrome P450 Superfamily," Biochemistry, (1995) 34:6956–61.

Jones, J.P., et al., Accelerated Communication: Three Dimensional Quantitative Structure–Activity Relationship for Inhibitors of Cytochrome P4502C9, (1996) Drug Metab. Dispos., 24(1):1–6.

Karki, S.B., et al., "On the Mechanism of Amine Oxidations by P450," Xenobiotica, (1995) 25(7):711–24.

Karki, S.B., et al., "Mechanism of Oxidative Amine Dealkylation of Substituted N,N–Dimethylanilines by Cytochrome P–450: Application of Isotope Effect Profiles," J. Am. Chem. Soc., 117(13):3657–64 (Apr. 1995).

Kim, S.S., et al., "Comparative Hammett Studies of Imidoyl, Benzylic, Aldehydic Hydrogens Transfer and Related Reaction by t–Butoxyl Radical," Tetrahedron Lett., (1985) 26(7):891–4.

Kobayashi, Y., et al., "Probing the Active Site of Cytochrome P450 2B1: Metabolism of 7–Alkoxycoumarins by the Wild Type and Five Site–Directed Mutants," Biochemistry, (1998) 37(19):6679–88.

Korzekwa, K. R., et al., "Theoretical Studies on Cytochrome P–450 Mediated Hydroxylation: A Predictive Model for Hydrogen Atom Abstraction," J. Am. Chem. Soc., (1990) 112:7042–6.

Korzekwa, K., et al., "The Use of Brauman's Least Squares Approach for the Quantification of Deuterated Chlorophenols," Biomed. & Environ. Mass Spectrom., (1990) 19:211–7.

Korzekwa, K.R., et al., "Predicting the Cytochrome P450 Mediated Metabolism of Xenobiotics," Pharmacogenetics, (1993) 3:1–18.

Lindsay Smith, J.R., et al., "Model Systems for Cytochrome P450 Dependent Mono–Oxygenases. Part 2. [1,2] Kinetic Isotope Effects for the Oxidative Demethylation of Anisole and [Me–$^2H_3$]Anisole by Cytochrome P450 Dependent Mono–Oxygenases and Model Systems," J. Chem. Soc. Perkin Trans. II, (1983) 5:621–8.

Macdonald, T. L., et al., "Oxidation of Substituted N,N–Dimethylanilines by Cytochrome P–450: Estimation of the Effective Oxidation–Reduction Potential of Cytochrome P–450," (1989) Biochemistry, 28:2071–7.

Manchester, J.I., et al., "A New Mechanistic Probe for Cytochrome P450: An Application of Isotope Effect Profiles," J. Am. Chem. Soc., (1997) 119:5069–70.

Nelson, D.R., et al., "P450 Superfamily:Update on New Sequences, Gene Mapping, Accession Numbers and Nomenclature," Pharmacogenetics, (1996) 6:1–42.

Northrop, D.B., "Deuterium and Tritium Kinetic Isotope Effects on Initial Rates," Methods Enzymol., (1982) 87:607–25.

Northrop, D.B., "Steady–State Analysis of Kinetic Isotope Effects in Enzymic Reactions," Biochemistry, (1975) 14(12)2644–51.

Omura, T., et al., "The Carbon Monoxide–Binding Pigment of Liver Microsomes," J. Biol. Chem., (1964) 239(7):2370–8.

Poulos, T. L., et al., "High–Resolution Crystal Structure of CytochromeP450cam," J. Mol. Biol., (1987) 195:687–700.

Ravichandran, K. G., et al., "Crystal Structure of Hemoprotein Domain of P450BM–3, a Prototype for Microsomal P450's," Science, (1993) 261:731–6.

Sakurai, H., et al., "Polar and Solvent Effects on Homolytic Abstraction of Benzylic Hydrogen of Substituted Toluenes by t–Butoxy Radical," J. Am. Chem. Soc., (1967) 89(2):458–60.

Shimoji, M., et al., "Design of a Novel P450: A Functional Bacterial—Human Cytochrome P450 Chimera," Biochemistry, (1998) 37:8848–52.

Silver, E.H., et al., "Structural Considerations in the Metabolism of Nitriles to Cyanide In Vivo," Drug Metab. Dispos., (1982) 10(5):495–8.

Smith, P. B., et al., "4–Ipomeanol and 2–Aminoanthracene Cytotoxicity in C3H/10T1/2 Cells Expressing Rabbit Cytochrome P450 4B1," Biochem. Pharmacol., (1995) 50(10):1567–75.

Szklarz, G. D. et al., "Site–Directed Mutagenesis as a Tool for Molecular Modeling of Cytochrome P450 2B1," Biochemistry, (1995) 34:14312–22.

Tassaneeyakul, W., et al., "Human Cytochrome P450 Isoform Specificity in the Regioselective Metabolism of Toluene and o–,m– and p–Xylene," J. Pharmacol. Exp. Ther., (1996) 276(1):101–8.

Tyson, C. A., et al., "The Roles of Putidaredoxin and P450$_{cam}$ in Methylene Hydroxylation," J. Biol. Chem., (1972) 247(18):5777–84.

Watanabe, Y., et al., "Kinetic Study on Enzymatic S–Oxygenation Promoted by a Reconstituted System with Purified Cytochrome P–450," Tetrahedron Lett., (1980) 21:3685–8.

Westheimer, F. H., "The Magnitude of the Primary Kinetic Isotope Effect for Compounds of Hydrogen and Deuterium," Chem. Rev., (1961) 61(3):265–73.

White, R. E., et al., "Oxygen Activation by Cytochrome P–450," Ann. Rev. of Biochem., (1980) 49:315–56.

White, R.E., et al., "Active Site Mechanics of Liver Microsomal Cytochrome P–450," Arch. Biochem. Biophys., (1986) 246(1):19–32.

White, R.E., et al., "Stereochemical Dynamics of Aliphatic Hydroxylation by Cytochrome P–450," J. Am. Chem. Soc., (1986) 108: 6024–31.

Wislocki, P.G., et al., "Reactions Catalyzed by the Cytochrome P–450 System," Enzymatic Basis of Detoxication, (1980) 1:135–82.

Yin, H., et al., "Designing Safer Chemicals: Predicting the Rates of Metabolism of Halogenated Alkanes," Proc. Natl. Acad. Sci. USA, 92(24):11076–80 (Nov. 1995).

Zerner, Michael C., "Semiempirical Molecular Orbital Methods," Reviews in Computational Chemistry II, Chapter 8, 313–365 (1991).

* cited by examiner

Phenylacetonitrile

Benzo[a]pyrene o-Methylanisole p-Methylanisole

α-Chloromethyl-p-xylene

USE OF COMPUTATIONAL AND EXPERIMENTAL DATA TO MODEL ORGANIC COMPOUND REACTIVITY IN CYTOCHROME P450 MEDIATED REACTIONS AND TO OPTIMIZE THE DESIGN OF PHARMACEUTICALS

RELATED APPLICATIONS

This application claims benefit of priority from U.S. Provisional Application No. 60/095,460, filed Aug. 5, 1998, which is hereby incorporated by reference as if fully set forth.

The U.S. Government may have certain rights in this invention pursuant to NIH Grant Nos. 1RO1ES/GM/09122-01, ES09122.

FIELD OF THE INVENTION

The present invention is directed to the use of computational and other experimental data in the design of new pharmaceuticals, and in predicting the metabolism profiles thereof. Computational and other information is used to further understand drug metabolism and toxicology, particularly in relation to monooxygenase enzymes, such as those of the cytochrome P450 system, that are involved in drug metabolism. Information derived according to the practice of the invention is useful in predicting the clearance or half-life of drugs, the propensity for drug interactions, and the nature and toxicity of byproducts resulting from their metabolism. The invention provides novel and powerful new approaches to drug design.

BACKGROUND OF THE INVENTION

The opportunity to improve the efficiency of the discovery phase of drug discovery is widely recognized in the pharmaceutical industry. Combinatorial chemistry and parallel synthesis methodologies, genomics, robotics, miniaturization, high-throughput screening and information technology together have stimulated an explosion of potential new lead compounds. However, limited expertise and resources are available to move a compound from "candidate" to "lead". This is partially because the development of new technologies to address the later stages of the lead optimization process have not kept pace with the combinatorial technologies developed for synthesis and screening. As a result, there is a bottleneck in the drug discovery process that begins with lead optimization and extends all the way to the selection of clinical development candidates.

A primary consideration in the area of lead development is a compound's metabolic fate. It would be of great value to the pharmaceutical industry if the discovery of such lead substances could be accelerated by design approaches that minimize reliance on screening synthesized compounds, but instead take advantage of quantifiable chemical or biochemical properties of a molecule in order to predict its metabolic characteristics. Predictive models can not only help alleviate the bottleneck in lead optimization but to facilitate the design and selection of drug candidates with not just adequate but with optimal absorption, distribution, metabolism and excretion/pharmacokinetic (ADME/PK) profiles for progression to the later, more costly stages of the drug discovery/development process. Compounds thus selected will not only have a greater chance of development success but will ultimately lead to better medicines.

In connection with the design of optimized pharmaceutical compounds, one particular area of interest involves a class of enzymes known as heme-containing monooxygenases, mixed function oxygenases, or alternatively cytochrome P-450s. These enzymes, which are abundant in the liver, act on a very broad range of substrate compounds, which is a trait very unusual for enzymes. These enzymes react with molecular oxygen such that one of the oxygen atoms is reduced to water, and the other is inserted into a substrate organic compound. This metabolic reaction may also be referred to as a hydroxylation reaction.

The cytochrome P450 (CYP) enzymes comprise a superfamily of heme-containing enzymes that consists of more than 700 individual isoforms, and are found in plant, bacterial and mammalian species (Nelson et al. (1996) *Pharmacogenetics* 6, 1–42). These enzymes function mainly as monooxygenases (Wislocki et al. (1980) in *Enzymatic Basis of Detoxification* (Jakoby, W. B., Ed.) pp 135–82, Academic, New York). In mammals, they are responsible for the metabolism of certain endogenous as well as exogenous compounds (Gonzalez, F. J. (1992) *Trends Pharmacol. Sci.* 13, 346–52). The catalytic cycle for aliphatic hydroxylation by mammalian CYP is described here briefly and shown in FIG. 1. Substrate binding changes the equilibrium of the heme iron from the low spin to the high spin state (step 1). This change lowers the reduction potential for the iron and facilitates electron transfer from NADPH via another enzyme, cytochrome P450 reductase (step 2). Molecular oxygen binds and is reduced by one electron as iron changes from the ferrous to the ferric state (steps 3 and 4). A second electron reduction of oxygen occurs and a peroxy intermediate is formed (step 5). The peroxy species undergoes heterolytic cleavage: one atom of oxygen leaves as a hydroxyl anion and the other forms a reactive oxygen species which is coordinated with the iron (step 6). Oxygen is transferred to the substrate (steps 7 and 8) and product dissociates from the enzyme (step 9). The first three steps of the cycle have been characterized spectroscopically. The next three steps occur rapidly, and have proven difficult to measure. At least two mechanisms have been proposed for the step(s) of oxygen transfer (depicted as steps 7 and 8 in FIG. 1), and are described briefly below.

The consensus mechanism for oxygen transfer is a nonconcerted reaction. In this context, nonconcerted implies that there are two distinct steps and that each step has its own transition state. There is evidence that step 7 (FIG. 1) is abstraction of a hydrogen atom from the substrate by the reactive oxygen, which yields a carbon-based radical and an iron bound hydroxyl radical (White et al. (1980) *Ann. Rev. of Biochem.* 49, 315–56). The next step (step 8 in FIG. 1) is rapid recombination of the two radical species, the "oxygen rebound" step. The magnitudes of isotope effects (Groves et al. (1978) *Biochemical & Biophysical Research Communications* 81, 154–60; and Hjelmeland et al. (1977) *Biochem. Biophys. Res. Commun.* 76, 541–9), loss of stereoselectivity (Groves et al., Ibid; and White et al. (1986) *J. Am. Chem. Soc.* 108, 6024–31), and evidence for rearrangement of the radical-like product of the first step (Groves et al. (1984) *J. Am. Chem. Soc.* 106, 2177–81) in various CYP-mediated reactions support the case for the oxygen rebound mechanism.

Suitable substrates for CYP include steroids, prostaglandins, fatty acids, and exogenous drugs, pesticides and other toxic environmental contaminants including many carcinogens. Hydroxylation reactions are often the first step in the metabolism of foreign substances leading, for example, to the inactivation of administered pharmaceuticals. Depending upon the mechanism of action of a drug, and its toxicological profile, it may be desirable to accelerate or delay its breakdown once it enters the body. Additionally other potential pharmaceuticals may be too toxic to administer, but appropriate structural modifications thereof may lead, for example, to structures that are decomposed to different, and less toxic, metabolites.

For example, metabolism of phenylacetonitrile at the benzylic position (FIG. 2, see arrow) causes the release of the toxic metabolite cyanide, whereas aromatic oxidation leads to a less toxic product (Silver et al. (1982) *Drug Metab. Dispos.* 10, 495–8). The metabolism of benzo(12) pyrene (Franchetti et al. (1995) *J. Med. Chem.* 38, 3829–37) by CYP and epoxide hydrolase yields several metabolites including the extremely carcinogenic compound 7(R),8(S)-dihydrodiol 9(S),10(R)-epoxide. These are examples where regioselectivity and stereoselectivity are important determinants of toxicity.

In addition, potential drug interactions can be caused by differences in metabolism of multiple drugs by a single CYP isoform, as well as the induction or inhibition of individual CYP isoforms by drugs. Polymorphic enzyme expression among individuals may cause unusual patterns of drug metabolism, which can lead to unwanted side effects.

As aforementioned, there is a tremendous need to enhance presently available methods for drug design to minimize dependence on the testing of randomly modified structures. But while progress has been made in the area of basic research, the field of predictive metabolism is not widespread in industry at this time. The two main determinants of enzymatic reactions are the steric and electronic characteristics of the enzyme and the substrate. Various electronic models have been developed that use computational (Grogan et al. (1992) *Chem. Res. Toxicol.* 5, 548–52; Korzekwa et al. (1990) *J. Am. Chem. Soc.* 112, 7042–6; and Yin et al. (1995) *Proc. Natl. Acad. Sci. USA* 92, 11076–80) and chemical (Karki et al. (1995) *J. Am. Chem. Soc.* 117, 3657–64; and Manchester et al. (1997) *J. Am. Chem. Soc.* 119, 5069–70) approaches for the successful prediction of relative reaction rates and isotope effect profiles for some classes of small compounds which are metabolized by CYP. The small sizes of the compounds reduce, or nearly eliminate, the steric contribution to the outcome of metabolism.

In some cases steric factors are the main determinants of CYP-substrate interactions (Jones et al. (1995) Biochemistry 34, 6956–61). Computational methods, which include molecular dynamics and molecular modeling, are currently employed to probe the interactions between the substrate and the enzyme (Jones et al. (1993) *J. Am. Chem. Soc.* 115, 381–7). These methods rely on the crystal structure of a CYP protein, but only a few crystal structures exist for four (soluble) bacterial CYP isoforms (Ravichandran et al. (1993) *Science* 261, 731–6; Poulos et al. (1987) *Journal of Molecular Biology* 195, 687–700; Hasemann et al. (1994) *Journal of Molecular Biology* 236, 1169–85; and Cupp-Vickery et al. (1995) *Structural Biology* 2, 144–53). Crystal structures for the (membrane bound) mammalian isoforms are not available. Although there is low sequence homology between bacterial and mammalian CYPs, current data suggests that some degree of tertiary structure is conserved (Korzekwa et al. (1993) *Pharmacogenetics* 3, 1–18). With the bacterial isoforms as a template, homology modeling techniques have been used to generate structural models of the mammalian isoforms (Hasemann et al. (1995) *Structure* 3, 41–62). The structural models have proven successful in locating residues near the active sites of mammalian CYPs (Szklarz et al. (1995) *Biochemistry* 34, 14312–22). The results have initiated site-directed mutagenesis studies, which have provided additional information about the structural details of the active site (Kobayashi et al. (1998) *Biochemistry* 37, 6679–88). This additional information has in turn been used to refine the homology models. The challenge remains to find a model that combines structural and electronic information for the prediction of the outcome of mammalian CYP-mediated reactions.

The present invention is directed to the use of computational models, in concert with other experimental data, to identify probable therapeutic compounds having improved therapeutic or toxicological profiles. CYP enzymes are amenable to the development of electronically based or quantum chemical predictive computational models for two reasons. 1) Many isoforms display low substrate specificity due to weak enzyme-substrate interactions. 2) The catalytic step of the enzyme family is thought to be the heterolytic cleavage of molecular oxygen (step 6 in FIG. 1). Therefore, for substrates that have weak interactions with the binding site of the enzyme, it is possible that the electronic features of the active oxygen and the inherent reactivities of various functional groups on a single molecule will dictate relative rates of metabolism.

The invention thus provides a system whereby computational and experimental data can be combined to define a unified model of drug reactivity. The methods thus provide for computational models for predicting rates and regiospecificity of drug metabolism. Although the approach is described in reference to properties resultant from interaction with monooxygenase enzymes such as CYP, it will be appreciated that the general principles are applicable in a wide variety of contexts.

SUMMARY OF THE INVENTION

The present invention is directed to methods that use experimental data, and also quantum mechanical (including electronic configuration) data, to parameterize the predicted reactivities of various substances, and their metabolites and precursors, upon interaction with an enzyme. The methods are most applicable for enzymes with broad substrate specificity (or low substrate selectivity). Examples of such enzymes include monooxygenases, glucoronyl transferases, and glutathione transferases.

Sample substances for which parameterization is desirable include various drug compounds or pharmaceutically active agents as well as any molecule introduced (such as by ingestion or inhalation) into a living organism. Upon such introduction, the substances may undergo reactions with various enzymes, including the monooxygenase cytochrome P-450 (CYP). Substrate reactions with CYP type enzymes, include for example, resultant hydrogen atom abstraction, aromatic oxidation, and metabolism at carbonyl groups or at heteroatoms.

Thus one aspect of the invention involves analysis of regioselectivities of various possible enzymatic reactions, and of the underlying chemical reactions, to identify structural features in pharmaceuticals that provide for advantages in non-adverse metabolism or bioactivation to toxic metabolites, half-life and dosing. As surprisingly described below, the regioselectivity of the underlying chemical reactions is often of greatest importance in such determinations.

In an uncatalyzed reaction, the regioselectivity of the reaction reflects the energetic differences for reaction of the various positions of the involved molecules. In an enzyme catalyzed reaction, however, the substrate compound is often bound to the enzyme in a very specific fashion, thereby changing the regioselectivity. The separation of reactivity differences intrinsic to the substrate from those attributed to steric interactions imposed by the enzyme is generally very difficult. Stated differently, it would generally be difficult to predict the effect of a structural modification of a target compound upon its metabolism by enzymes, given that the molecular mechanisms of its metabolism involve an intimate combination of effects contributed by the metabolizing enzymes and the compounds themselves.

According to the practice of the present invention however, it has been determined that, with respect to metabolism of various compounds (including potential pharmaceutical substances), large amounts of predictive information pertaining to optimized metabolism by enzymes with broad substrate specificity are, in fact, directly derivable from the regioselectivity of underlying electronic structure of the reactants. As such, the information may be derived without requiring reference to the enzymes. This greatly facilitates computational analysis of optimized structural features in newly designed therapeutics.

Without being limited as to theory, it is believed that certain enzymes, such as CYP, have evolved to metabolize a wide range of substances not otherwise readily metabolized or detoxified. As a result, and in order to provide a broad range of response, the normal high selectivity of enzymes for particular substances, and the steric requirements normally found at enzyme active sites, have been lessened, thus substantially enhancing the value of computational information that may be derived solely by reference to the electronic configuration of the metabolized substrates.

Although the above concepts are primarily described herein with respect to human pharmaceuticals and CYP, the methods of the invention are also applicable to any enzyme with broad substrate specificity for the design of industrial or agricultural chemicals, and the like, where interest is focused not on optimizing dose or pharmacodynamics, but rather avoiding metabolism (bioactivation or inactivation) of substances that may come in contact with the human body (such as pesticides or pharmaceutical agents) where it is intended to avoid undesirable metabolism.

DETAILED DESCRIPTION OF THE INVENTION

Figure 1:
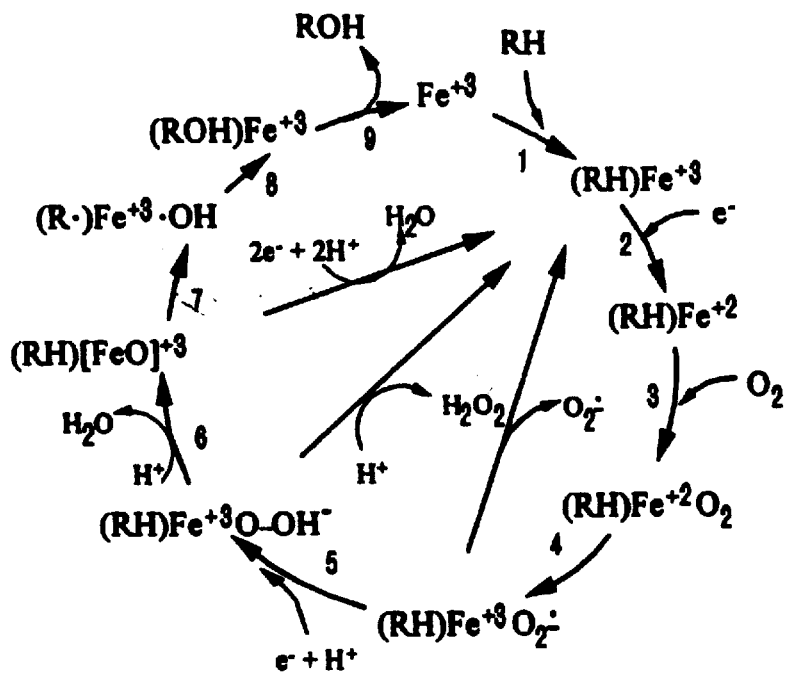
FIG. 1 depicts a proposed catalytic-cycle for cytochrome P450.
Figure 2:
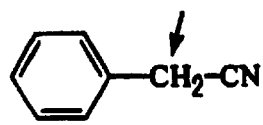
FIG. 2 shows cytochrome P450 substrates which can be metabolized to toxic compounds.
Figure 2:
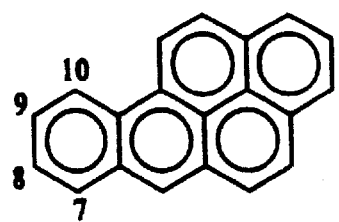

As described above, the present invention is directed to methods of determining the electronic tendency for metabolism of a compound by enzymes with broad substrate specificity. Such methods use experimental data, and also quantum mechanical (including electronic configuration) data, to parameterize the predicted reactivities of various substances upon reaction with such enzymes. While such reactions may include steric factors in addition to electronic factors, or even be sterically driven, the methods of the invention provide a means of determining enzymatic metabolism of various substances.

In one embodiment of the invention, such methods comprise the steps of a) determining, without reference to said enzyme, the regiospecific reactivity of each functional group in said compound towards metabolic transformation by any reaction(s) mediated by said enzyme;

b) deriving one or more equations relating the activation energy for each enzyme mediated reaction to quantum chemical descriptors;

c) determining, from said one or more equations, the metabolism of said compound by predicting the activation energies for each reaction;

wherein said determined electronic tendency provides the electronic component for said reactions.

As such, the methods determine the metabolism of various compounds by use of the regiospecific reactivity of functional groups, such as C—H, C—C, C=C, C≡C, C=O, C—N, C=N, —S—, —N—, —N=, —CHO, —OH, and —COH, in combination with equations relating the activation energy for each enzyme mediated reaction to quantum chemical descriptors. The activation energy for each enzyme mediated reaction may further be related to the heat of reaction with said compound. One means for deriving the equations is by use of semiempirical methods.

The equations can be refined by parameterization with experimental results to correct errors in activation energies due to the use of semiempirical methods. Such experimental parameterization may be accomplished by identifying the relative rates of substrate rotation in the active site of the enzyme by determining the isotope effect profiles for said reaction(s).

The equations can also be refined by calculating high level quantum chemical parameters to correct the errors in activation energies. The use of high level quantum chemical parameters may be used in combination with the experimental parameterization described above, and includes the use of ab initio methods to correct the quantum chemical activation energy (AM1) and/or the spin contamination in said one or more equations.

With such methods, it can be determined whether metabolism of a compound results in one or more of the following:

(1) the production of an excess concentration of a toxic metabolite;

(2) an excessive rate of metabolism of a pharmaceutically useful substance;

(3) an inadequate rate of metabolism of a pharmaceutically useful substance; and (4) an excessive rate of metabolism of a non-pharmaceutically useful substance into a toxic metabolite.

While the methods of the invention may be applied to any enzyme with broad substrate specificity, the following discussion is based on the use of a monooxygenase, CYP, as a representative example. As such, the predominant enzyme mediated reactions discussed concerns hydrogen atom abstraction and oxygen addition. These reactions include hydroxylation and aromatic oxidation. Obviously, the use of other low substrate selectivity enzymes such as glucoronyl and glutathione transferases would focus on other chemical reactions.

Essentially any new hydrophobic drug or xenobiotic will serve as a substrate for the cytochrome P450 (CYP) system. As such a predictive model for reactions catalyzed by these enzymes, in particular human CYP enzymes, would be an extremely useful tool. If the rate of a given CYP mediated oxidation of a substrate can be predicted, a number of properties could be anticipated, including: the clearance of drugs, the toxicity of xenobiotics, and the amounts of different metabolites that would come from a given substrate. These predictions will be useful in drug design, drug metabolism, and toxicology.

Certain CYP enzyme characteristics render them suitable for theoretical calculations to be used to model their reactivity. First, the enzyme's principle catalytic steps involve the generation of an active oxygenating species. Other than by possibly initiating the steps, substrates are not directly involved. Upon generation of the active oxygenating species, the substrate is reacted in a manner that appears to be "chemical-like", such that only the broad regioselectivity of the reaction is influenced by the enzyme. Secondly, many CYP mediated reactions are unlikely to involve significant charge generation during the initial step of oxidation because the active oxygen is believed to have radical characteristics. Additionally, the CYP active site is thought to be a more hydrophobic than polar environment, so that gas-phase calculations would be a better approximation.

With respect to the present invention, the following references are specifically incorporated by reference herein, as if fully set forth, and form a part of the present disclosure: J. Grogan et al., *Chem. Res. Toxicol.*, Vol. 5, No. 4, pp. 548–552, 1992; H. Yin et al., *Proc. Natl. Acad. Sci. USA*, Vol. 92, No.5, pp. 11076–11080, 1995; J. Jones et al., "Predicting the Rates and Regiospecificity of Reactions Mediated by the P450 Superfamily", in *Methods in Enzymology*, Vol. 272, pp. 326–335, 1996; and K. Korzekwa et al., *J. Am. Chem. Soc.*, Vol 112, pp. 7042–7046, 1990.

The predictive models for drug metabolism of the invention are based upon the application of quantum chemistry methods. These include semiempirical (electronic) methods and gaussian-based ab initio methods. These methods are known in the art (see Lickowitz et al. ed., Reviews in Computational Chemistry II, VCH Publishers, 1991, pp. 313–315). To a first approximation, the electronic structure of a molecule is determined by the orientation of the atoms in space. Stable geometries of molecules are associated with atomic configurations that provide the lowest energy electronic configurations. Reactions occur through changes in atomic configurations from reactants to products. Along the reaction coordinate, the energy increases from the reactant geometry (stable, low energy configuration) to the transition state geometry (unstable, high energy configuration) and then decreases again to form products.

Quantum chemical techniques attempt to model the electronic configurations and energies associated with atomic orientations. Approximate geometries can be optimized to stable geometries by minimization of the energy with respect to the atomic coordinates. Reactions can be modeled by transforming the reactant geometry to product geometry and minimizing all but one degree of freedom.

Thus, the "heart" of a quantum chemical method is the method used to calculate the electronic structure for a given atomic configuration. The electronic configuration of a molecule is obtained by combining the atomic orbitals to form molecular orbitals. The equations for the electronic wavefunctions have been around since the beginning of this century, but they are not amenable to solution. Therefore, different approximations are used in the solution of the equations.

The complex part of the electronic structure calculation is associated with the multicenter electron repulsion terms. Semiempirical (electronic) methods approximate these terms with functions that are optimized to reproduce geometries and heats of formation. The resulting electronic configurations and energies are dependent on the initial parameterization of the semiempirical method. In contrast, ab initio methods make no use of experimental data. Instead these calculations approximate the atomic orbitals with combinations of gaussian functions that are amenable to integration. The more gaussian functions that are used (larger basis set), the more accurate the electronic representation. Also, the lower the energy, the better the calculation.

Another important concept is that a lower energy can be obtained by mixing in excited state electronic configurations. This is due to electron correlation, the tendency for electrons to keep away from each other. This energy gain is insignificant for most molecules, but are important for radicals, excited states and unstable geometries such as transition states. Accurate ab initio calculations require additional efforts to include correlation.

Semiempirical calculations are fast, allowing very large molecules to be modeled. Ab initio calculations with large basis sets and correlation corrections are very slow, due primarily to the correlation correction. Calculations are presently limited to about ten heavy (non-hydrogen) atoms.

An additional ab initio method based on density functional theory is also used in the invention. These methods include a correlation functional in the wavefunctions calculation. Although these calculations are much faster than correlation-corrected-calculations, the exact form of the correlation functional is not implicit. Therefore, these functionals are parameterized, resulting in some of the same deficiencies of semiempirical calculations, i.e. a lower energy does not necessarily imply a better calculation. These calculations appear to be excellent for ground states (i.e. reactants and products) and may be applicable for transition state calculations upon modification.

The invention uses semiempirical calculations (AM1) to construct predictive models of drug metabolism. These models are based on the electronic tendency for metabolism, as determined by the reactions of substrates with small organic oxygen radicals. The speed of semiempirical calculations allows essentially any drug molecule to be modeled. Correlated (MP2) ab initio methods and density functional methods are used to provide more meaningful energies that can be used to validate and correct the semiempirical results.

Based on the above, the present invention is directed to models for CYP mediated hydrogen atom abstraction and aromatic oxidation reactions based on reactions between a number of small radicals and substrates. The radicals used include p-nitrosophenoxy radical (PNR), t-butoxy radical, methoxy radical, HSO radical, and FO radical. Other radicals may be used for generating additional models for hydrogen atom abstraction and aromatic oxidation reactions as well as other P450 mediated reactions.

PNR model limitations

Our previously published model uses the p-nitrosophenoxy radical in hydrogen abstraction reactions as a model for CYP mediated hydrogen atom abstraction. Using this model, the relative rates of reaction for several classes of small hydrophobic compounds can be accurately predicted. For example, the model has been able to predict the toxicity ($LD_{50}$) of nitrites, the rates of in vitro metabolism of substituted toluenes and haloalkanes, and the rates of in vivo metabolism of halogenated hydrocarbon anesthetics. This model is based solely on computational data. Since only one kind of reaction is involved, parameterization of the linear model to generate absolute rates is not necessary, because the relationship between the relative rates will be maintained irrespective of the absolute values of the parameters.

Although the PNR model is useful in predicting one class of CYP reactions (hydrogen atom abstractions), a complete predictive model for the CYP enzymes must also include other reaction types. These include aromatic oxidation, olefinic oxidation, carbonyl metabolism, N-oxidation and S-oxidation. Deficiencies with the previously published PNR model became apparent when other reactions were modeled. These problems are summarized as follows:

1) Systematic errors within a computational method may not be consistent across different reaction types. Differences in systematic errors are expected since:
   a) The systematic errors are dependent on the nature of the potential energy surface. As an example, the absolute activation energies are greatly overestimated within the AM1 formalism. The value of the computation is due to its ability to provide relative activation energies.
   b) Entropy terms are expected to cancel out within a series of related reactions, but will not cancel when different reactions are considered.

2) Radical addition reactions have substantial spin contamination. This is a deficiency of the UHF (unrestricted Hartree-Fock) method, in which the wave function for open shell systems are contaminated with higher spin state wave functions. This bestows more uncertainty on the relative energetics of the calculations. The transition states have $<S^2>$ values of approximately 2.1 and the tetrahedral intermediates have, $S^2>$ values of approximately 1.1. Pure doublets have $<S^2>$ values of 0.75, indicating significant contamination with higher spin states. If the amount of spin contamination remains constant, as is the case for the substituted benzenes, the error is also likely to be constant and will not be problematic. However, calculations on polycyclic aromatic hydrocarbons show that the degree of spin contamination depends on the extent of conjugation of the radical, i.e., the degree of spin contamination is not size consistent. Therefore, different substrates will have different errors due to spin contamination.

3) Although addition of the nitrosophenoxy radical to an aromatic carbon progresses smoothly through a transition state and on to a tetrahedral intermediate, the electronic state of the tetrahedral intermediate is not the ground state. Thus, the reactions from reactants to products and products to reactants occur on two different potential energy surfaces. In addition to complicating any transition state studies, the value of any Bronsted correlations will be in doubt, since the transition states are not necessarily intermediate between products and reactants.

Therefore, it was necessary to use a completely different approach to develop more comprehensive predictive models for the CYP enzymes. This invention describes a method that uses experimental data and additional quantum chemical methods to parameterize models that will predict several types of CYP mediated oxidation reactions, including hydrogen atom abstraction, aromatic oxidation and the metabolism of carbonyl compounds. This model does not require the calculation of transition states for a model oxygen radical such as the nitrophenoxy radical. Instead, the model is parameterized using experimental regioselectivities of enzymatic reactions. Additional input for model development is provided by rates of reactions of chemical systems, and ab initio quantum chemical calculations using alkoxy radicals.

Parameterization with Enzymatic Systems

Based on a number of CYP characteristics described in the Examples below, the validity of deriving predictive information from the underlying electronic structure of the reactants is demonstrated. The characteristics include the demonstration by kinetic isotope effects (KIEs) that the active CYP oxygen is equivalent in a number of CYP isoforms; and the indication by intramolecular and intermolecular KIEs as well as the ratio of products from competing CYP mediated reactions on a model substrate that rapid substrate rotation permits use of electronic factors alone to predict regioselectivity. The latter point is of particular significance because it permits the use of model radicals in place of CYP enzymes in obtaining model data for deriving predictive models.

Given these results, models for hydrogen atom abstraction and aromatic oxidation were derived upon application of quantum chemistry methods.

Use of semiempirical (electronic) methods, however, result in incorrect absolute activation energy (AM1) barriers, making the methods inappropriate for comparing the energetics of different reaction mechanisms. But it is preferable to use models based on these methods to minimize the computational costs of the calculations. In order to calculate ratios of metabolites from a single compound and to include other reaction mechanisms, the AM1 barriers need to be corrected by correlation with experimental data. Experimental data is obtained from metabolite ratios when a substrate undergoes rapid exchange between positions of metabolism. This rapid exchange, which is also referred to as rapid equilibrium, reflects the rapid substrate rotation in CYP mediated reactions and may be determined by KIE studies.

Hydrogen atom abstraction

Based on the above, an initial model for hydrogen atom abstraction by CYP of the invention was formulated based on the semiempirical quantum chemical activation energy (AM1) from quantum chemical descriptors of the substrate and the radical product. This can be expressed by the following formula of Equation 1, relating the activation energy ($\Delta H_{act}$) to the respective heat of reaction ($\Delta H_R$) for each hydrogen atom abstraction reaction and the ionization potential of the resulting radical ($IP_{rad}$). This allows for the prediction of AM1 activation energies with a rapid calculation of ground state properties.

$$\Delta H_{act}=2.60+0.22(\Delta H_R)+2.38(IP_{rad}) \qquad \text{Eq. 1}$$

This equation, when used alone, can reproduce the AM1 activation energies, but the AM1 formalism is known to overestimate these barriers. Thus, as described above, experimental data can be correlated with this equation to correct the overestimation. This is possible upon correlations with regression of experimental data on parameters that include functions of this AM1 activation energy. The overestimated barriers are corrected by a proportionality constant of the regression equation. The improvement based on correlation with the regression is dependent on the number of experimental data points used in the regression. As such, the accuracy of the equation can be repeatedly improved by correlating with regressions based on increasing amounts of experimental data.

Five substrates shown to undergo rapid equilibrium between positions of metabolism have been used to prepare data for regression and then correlation with Eq. 1. The differences in activation energy calculated by the experimental regioselectivity of the substrates, along with the differences in AM1 activation enthalpies, are given in Table 1. Regression of the experimental data gives a slope correction for AM1 activation energies of 0.75±0.20.

TABLE 1

Experimental and AM1 energy differences.

| Substrate | $\Delta\Delta G$ (experimental) | $\Delta\Delta H$ (AM1, PNR) |
|---|---|---|
| 4-methylanisole | 1.1 | 2.2 |
| 2-methylanisole | 0.3 | 2.3 |
| a-chloro-p-xylene | −1 | −1.3 |
| Octane | −3.13 | −2.6 |
| Valproate | −2.48 | −2.6 |

Another source for correcting AM1 activation energies is with high level ab initio calculations, which may be combined with experimental corrections. As stated above, t-butoxy and methoxy radicals can be used as models for CYP mediated hydrogen atom abstraction reactions. Table 2 gives the ab initio MP2/6311+G* activation energies for methoxy radical mediated hydrogen atom abstraction, compared to the AM1 results with the p-nitrosophenoxy radical. MP2 and 6311+G* are ab initio quantum chemical formalisms known in the art.

TABLE 2

Ab initio and AM1 Activation Energies.

| Substrate | $\Delta H_{MP2}$ (MP2/6311 + G*) | $\Delta\Delta H_{AM1}$ |
|---|---|---|
| Propene | 10.60318 | 21.53 |
| methylamine | 9.078607 | 17.78 |
| acetonitrile | 15.72245 | 26.33 |
| ethane | 13.34009 | 24.57 |
| methane | 16.46698 | 26.99 |

Regression of this data gives Eq. 2, with an $r^2=0.95$.

$$\Delta H_{MP2} = -6.11 + 0.82(\Delta H_{AM1}) \quad \text{Eq. 2}$$

The slope correction of 0.82 is similar to the experimental correction of 0.75 described above. The intercept correction of −6.11 is essentially cosmetic because it cancels when relative free energy differences are calculated. Using the experimental correction of 0.75 and an intercept correction of −6.11 as corrections to Eq. 1 results in the experimentally corrected equation for hydrogen atom abstraction (Eq. 3).

$$\Delta H_{act} = -4.16 + 0.165 \, (\Delta H)_R + 1.78(IP_{rad}) \quad \text{Eq. 3}$$

This equation gives the best fit of AM1 heats of reaction and ionization potential to the experimental data in Table 1.

It also brings the absolute values in line with the calculated MP2/6311+G* activation energies.

Given the above, predictions for the electronic tendency for hydrogen atom abstraction of a given compound of interest by CYP can be made by simply calculating the radical and substrate heats of formation, which provide the heat of reaction by subtracting the former from the latter, and the ionization potential of the radical. For substrates that rotate rapidly in the P450 active site, the model will predict regioselectivity. If steric effects are involved, the model will predict the electronic component of the reaction.

The validity of this method to predict hydrogen atom abstraction is Observed for the CYP3A4 enzyme. This enzyme has the broadest substrate specificity and apparently minimal steric interactions for most substrates. A representative list of CYP3A4 substrates is shown in Table 3.

TABLE 3

Use of CYP3A4 Regioselectivity to Validate the Electronic Model for Hydrogen Atom Abstraction.

| Compound | Primary metabolism predicted to be 1st Electronic | Primary metabolism predicted to be in top 3 <-------------> | Not in top 3 Steric |
|---|---|---|---|
| Buprenorphine | X | | |
| Cocaine | X | | |
| Estrone | X | | |
| Nifedipine | X | | |
| Nitrendipine | X | | |
| Morphine | X | | |
| Ethylmorphine | X | | |
| Dextromethorphan | X | | |
| Cyclobenzaprine | X | | |
| Codeine | X | | |
| Clozapine | X | | |
| Tamoxifen | X | | |
| Testosterone | | X | |
| Salmetrol | | | X |
| Quinidine | | | X |

In this Table, the model accurately predicted the primary metabolite for 12 of 15 substrates. This suggesets that the oxidation of these substrates is electronically controlled. Compounds that are metabolized in deactivated positions are likely to be sterically controlled.

Aromatic Oxidation

Aromatic oxidation is likely to occur through a radical addition mechanism. Unfortunately, addition of the p-nitrosophenoxy radical to an aromatic carbon progresses smoothly through a transition state and onto a tetrahedral intermediate where the electronic state of the intermediate is not the ground state. Thus, the reactions from reactants to products and products to reactants occur on two different potential energy surfaces. In addition to complicating transition state studies, the value of any Brönsted correlations for addition to substituted benzenes will be doubtful because the transition tates are not necessarily intermediate between products and reactants.

Thus the p-nitrosophenoxy radical alone is not likely to serve as a versatile model for other CYP mediated oxidations. The difficulties in developing a quantum chemical model with the PNR model can be summarized as 1) inaccurate energies associated with AM1 calculations, 2) spin contamination for unrestricted Hartree-Fock (UHF) calculations, and 3) surface crossings for the p-nitrosophenoxy radical model. These problems have been solved by 1) using experimental parameterization, and 2) use of high level ab initio calculations to guide the experimental parameterization, and 3) use of methoxy radical as the model oxidant.

The validity of using experimental parameterization is presented by the following, which shows the likely rapid rotation of substrates undergoing CYP mediated aromatic oxidation and the validity of using radicals to model CYP mediated aromatic oxidation reactions.

To address the issue of inaccurate energies associated with AM1 calculations, small oxygen radicals other than the p-nitrosophenoxy radical were tested within the AM1 formalism. HSO and FO radicals were found to add smoothly to aromatic compounds using the AM1 formalism. In contrast to the p-nitrosophenoxy radical previously used, HSO and FO radicals remain on a single potential energy surface. Both radicals provide excellent modified Brönsted correlations for addition to substituted benzenes, with $R^2$ values of 0.98 for HSO and 0.99 for FO. These excellent correlations for both the meta and para positions indicate that models can be developed to describe diverse electronic characteristics. This data also suggest that the activation energies will simply be a function of heats of reaction and do not need to be corrected for resonance.

The issue of significant amount of spin contamination along the reaction coordinate for UHF calculations is a more difficult problem. This reflects a deficiency of the UHF method, in which the wave function for open shell systems are contaminated with higher spin state wave functions. This results in added uncertainty in the relative energetics of the calculations. The transition states have $<S^2>$ values of approximately 1.2 and the tetrahedral intermediates have $<S^2>$ values of approximately 1.1. Pure doublets have $<S^2>$ values of 0.75, indicating significant contamination with higher spin states. If the amount of spin contamination remains constant, as is the case for substituted benzenes, the error is also likely to be constant and not problematic. Calculations on polycyclic aromatic hydrocarbons, however, show that the degree of spin contamination depends on the extent of conjugation of the radical, i.e. the degree of spin contamination is not size consistent. Thus correction for spin contamination is necessary.

One means of correcting for spin contamination is with ab initio calculations. MP2, MP4, and density functional ab initio calculations have been used to obtain ground state substrates, and when possible and necessary, transition states. Obtaining reasonably accurate energetics requires at least an MP2 level of theory with a 6-31 G* basis set. MP4, 6-31 G*, and DFT are ab initio quantum chemical formalisms known in the art. Using this basis set, hydrogen atoms were abstracted from a series of substrates using tert-butoxy and methoxy radicals. The methoxy radical adds smoothly to aromatic systems. The MP2 calculations have minimal spin contamination after projection.

Figure 3:
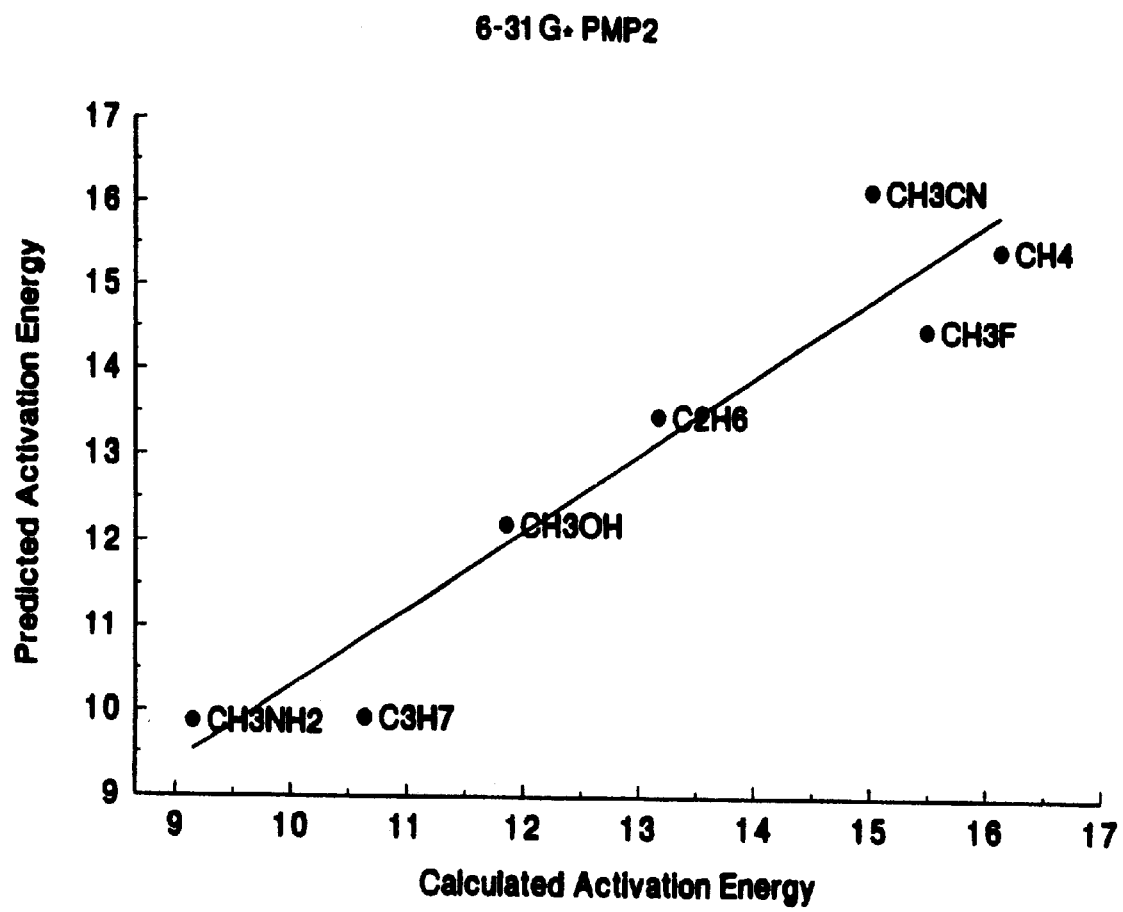
FIG. 3 depicts results of hydrogen abstraction reactions with the methoxy radical.

The modified Brönsted correlations for the methoxy radical calculation are shown in FIG. 3. Similar results were obtained for the tert-butoxy radical calculations. The methoxy radical was used since it is substantially smaller than the tert-butoxy radical. Since the upper limit for the number of non-hydrogen atoms in a molecule is approximately ten, many more reactions can be modeled if the methoxy radical is used. The energetics for these two molecules are likely to be similar since the experimental OH bond dissociation energies are almost identical. As with the semi-empirical PNR model, reasonable modified Brönsted correlations are obtained for both methoxy ($R^2=0.91$) and tert-butoxy radicals ($R^2=0.92$). Therefore, methoxy radical calculations (6-31 G*/MP2) may provide a reasonable model for P450 oxidations. These results suggest that ab initio calculations with alkoxy radicals can be used to guide the parameterization of the computational models.

Another method of correcting for spin contamination is with density functional calculations. These methods are fast, high level ab initio methods that can provide correlated results with very little spin contamination. Although their value in transition state calculations is uncertain, they can provide good uncontaminated ground state energies. For example, the bond dissociation energies for seven carbon hydrogen bonds were found proportional to the spin projected MP2 bond dissociation energies ($R^2=0.93$), and an excellent correlation between tert-butoxy radical abstraction rates and DFT calculations has been obtained (see below). DFT calculations have no spin contamination.

Figure 4:
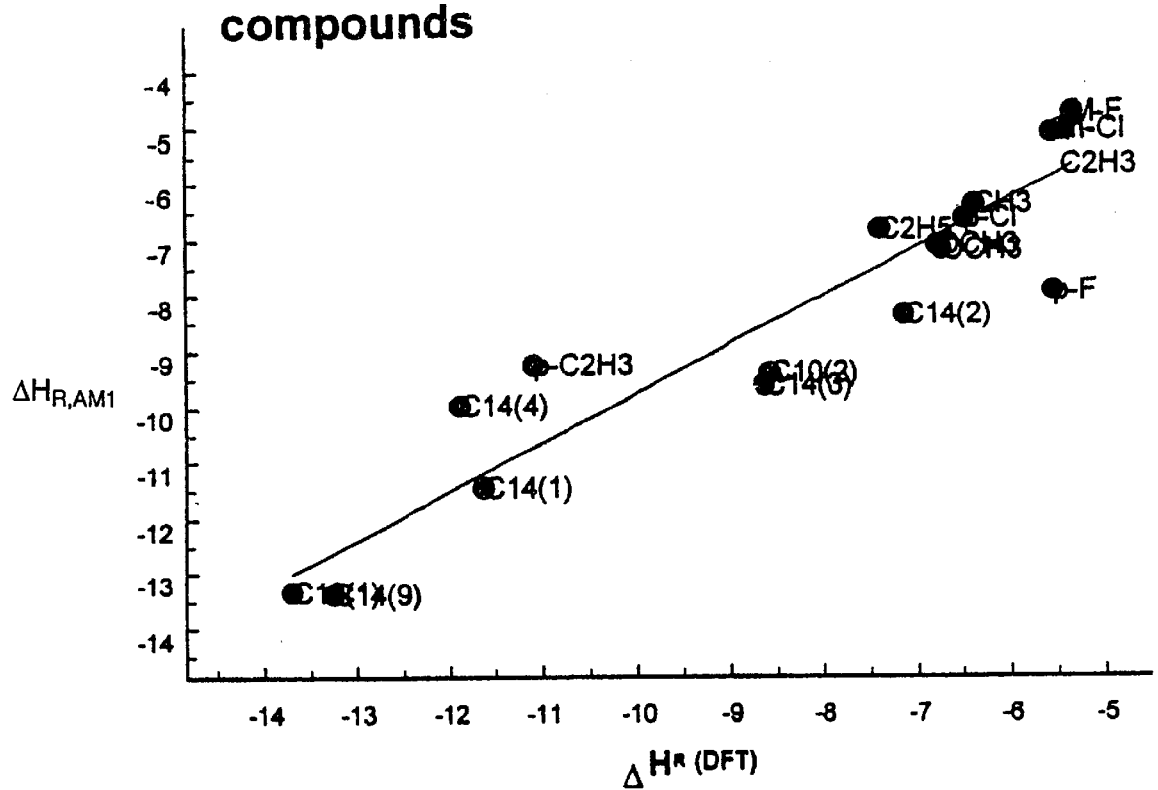
FIG. 4 shows correction of AM1 heats of reaction to match DFT values

Therefore, an approach is to use density functional ab initio methods to correct for spin contamination in heats of reaction. These corrected heats of reaction can then be used to predict activation energies for aromatic oxidation. FIG. 4 shows the correlation between density functional (B3LYP) and AM 1 heats of reaction for methoxy radical addition to aromatic rings. The parameters for the fit is given in Eq. 4, where a value $\Delta S^2$ is a correction for UHF spin contamination in the AM1 calculation.

$$\Delta H_{R,DFT} = 19.2 + 1.32(\Delta H_{R,AM1}) + 5.47(\Delta S^2) \quad \text{Eq. 4}$$

The generation of an accurate combined model for hydrogen atom abstraction and aromatic oxidation requires consideration of competing oxidation reactions hydrogen atom abstraction reactions since. The relationship between these competing reactions can be expressed by Equations 5 and 6, where a is the intercept correction for aromatic oxidation, b is the slope term for aromatic oxidation, the term a(1−y) is used with y=1 when an intercept correction is not needed (as in Eq. 5) and y=0 when an intercept correction is needed (as in Eq.6). These equations permit simultaneous solution of data sets containing aromatic oxidation with and without hydrogen abstraction ratios.

$$\ln\frac{P_{arom1}}{P_{arom2}} = a(1-y) + b(\Delta\Delta H_{R,arom}) \quad \text{Eq. 5}$$

$$\ln\frac{P_{arom}}{P_{Habs}} = a(1-y) + b(\Delta H_{R,arom}) - \Delta H_{Habs} \quad \text{Eq. 6}$$

These equations may be solved with the data in Table 4, which provides experimental data for aromatic oxidation reactions with a number of substrates.

TABLE 4

Experimental Product Ratios for Aromatic Oxidation

| Substrate | Ratio Description | Experimental Ratio | $\Delta\Delta H$ (AM1) $H_{abs}$ | $\Delta H_R$ (AM1) aromatic | $\Delta\Delta H_R$ (AM1) aromatic |
|---|---|---|---|---|---|
| Toluene | Arom/benz | 0.13 | 12.32 | −7.19 | — |
| Anisole | Arom/benz | 10.6 | 11.29 | −6.39 | — |
| Ethylbenzene | Arom/benz | 0.086 | 10.21 | −6.83 | — |
| 2-methylanisole | Arom/benz | 1.76 | 10.52 | −7.12 | — |
| Phenanthrene | 1-OHP/9-OHP | 0.61 | — | — | −1.90 |
| Phenanthrene | 4-OHP/9-OHP | 0.35 | — | — | −3.40 |

Upon solution, the data in Table 4 gives parameters of a=11.72 and b=0.28. Solving for aromatic oxidation on the corrected hydrogen abstraction scale results in Eq. 7.

$$\Delta H_{arom} = 11.25 + 0.24(\Delta H_{R,arom}) \quad \text{Eq. 7}$$

Combining Equations 7 and 4 results in Eq. 8, which predicts aromatic oxidation with AM1 parameters.

$$\Delta H_{arom} = 15.86 + 0.32(\Delta H_{R,AM1}) + 1.31(\Delta S^2) \qquad \text{Eq. 8}$$

As with the equations for hydrogen abstraction provided above, the accuracy of the above equations can be repeatedly improved by use of increasing amounts of experimental data.

Figure 5:
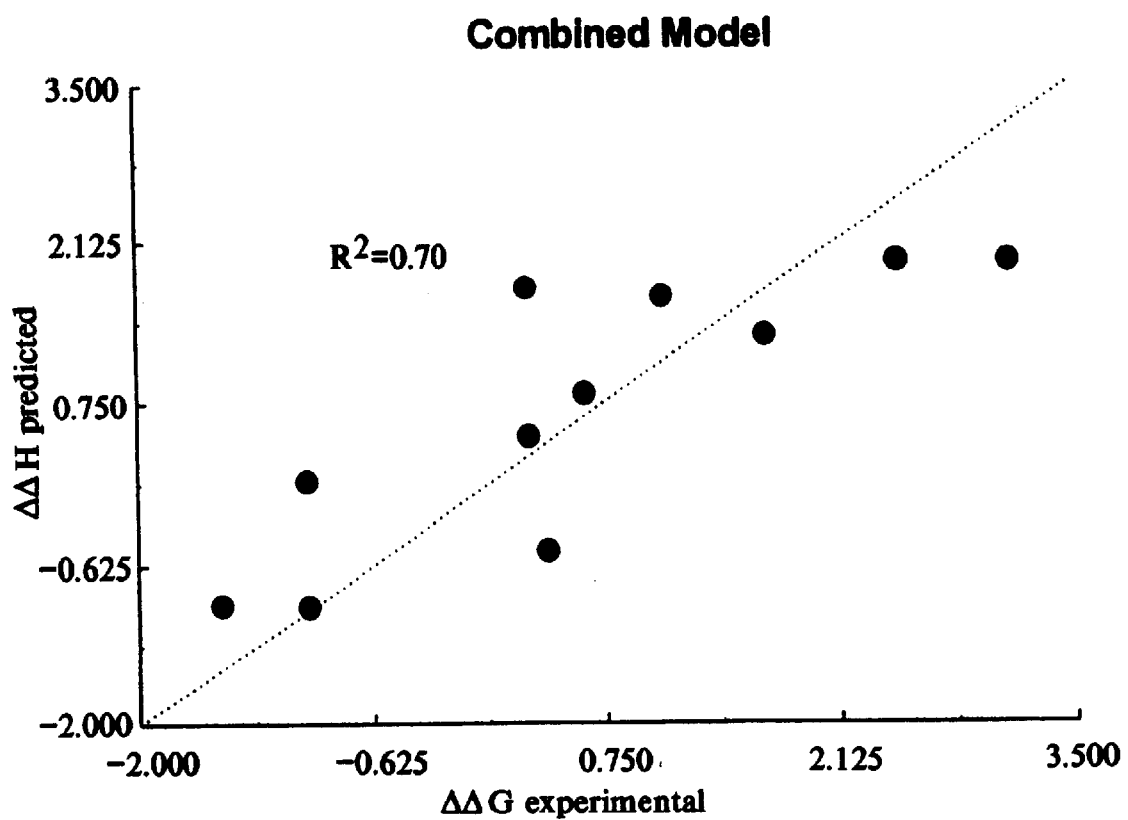
FIG. 5 shows experimental $\Delta\Delta G$ versus predicted $\Delta\Delta H$ for ratios of hydrogen abstraction and aromatic oxidation reactions.

Given the above, and similar to the situation for hydrogen atom abstraction, predictions for aromatic oxidation of a given compound of interest by CYP can be made by calculating the AM1 heats of reaction and measuring the spin contamination of the resulting radical. Eq. 8 above, is used to predict the activation energy of the reaction. This activation energy can be directly compared with hydrogen abstraction reactions calculated by Eq. 3. FIG. 5 shows the ability of the above methods to predict both hydrogen abstraction and aromatic oxidation. The energy differences obtained from both experimental and predicted data demonstrates the consistency of the predictive model.

The equations correct models derived from pure AM1 quantum chemical calculations to better match experimental data. Availability of additional experimental data will provide a means for further refinement of the coefficients in each equation.

Other CYP mediated reactions

CYP is capable of mediating additional reactions beyond hydrogen atom abstraction and aromatic oxidation. These reactions include olefinic oxidation, carbonyl metabolism, N-oxidation and S-oxidation. The formulation of predictive models for these reactions may be conducted in the same manner as that provided above for hydrogen atom abstraction and aromatic oxidation. The mechanism of each reaction is first modeled and then separately parameterized by experimentation as provided above.

For example, carbonyl metabolism is likely to be hydrogen atom abstraction based. As such, rapidly rotating substrates capable of the carbonyl metabolism reactions of compounds of interest will be modeled with semiempirical (electronic) methods and then parameterized with ab initio methods. Similarly, N- and S-oxidation probably proceed by oxygen addition, which may also be modeled by rapidly rotating substrates undergoing oxygen addition. These substrates may then be used for experimental parameterization by both semiempirical and ab initio methods.

Having described the invention with regard to CYP enzymes in general, it should be clear that all of the disclosed invention is applicable to human CYP enzymes, including, but not limited to CYP2E1, CYP3A4, CYP2B6, CYP2C8, CYP2C9, CYP1A1, CYP1A2, CYP2C19, CYP2D6, CYP1B1, and CYP2A6.

The following examples are intended to support and illustrate but not to limit the invention.

EXAMPLE 1

General Computing Methods

A variety of software packages that are commercially available or otherwise in the public domain are useful in performing the quantum chemical calculations used in the practice of the invention.

Both ab initio and semiempirical calculations can be performed using Gaussian 94 or Gaussian 98, which are available from Gaussian, Inc., Carnegie Office Park, Building 6, Suite 230, Carnegie, Pa. 15106, USA. Semiempirical and density functional calculations can be performed from within the Insight II software offered by Molecular Simulations Inc., 9685 Scranton Road, San Diego, Calif., USA. Semiempirical calculations can also be performed using the commercial and public domain versions of MOPAC which is available from the Quantum Chemical Program Exchange, Indiana University, Creative Arts Building, Bloomington, Id., USA

EXAMPLE 2

Similarity in Energetics of Active Oxygen in CYP Enzymes

Due to heterogeneity in the CYP enzyme family, it was necessary to confirm that the energetics of any given reaction would be similar for each CYP. One means of confirming this is by comparing isotope effect profiles (IEPs) of a number of CYP enzymes to verify that the active oxygen in each energetically equivalent. For CYP mediated reactions, the physical characteristics of a compound and the nature of the active oxygen species dictate the magnitude of an intrinsic isotope effect. An IEP consists of isotope effect measurements for a series of structurally related compounds that most nearly approximate intrinsic isotope effects using multiple CYPs. When intrinsic kinetic isotope effects (KIEs) are available, comparable trends in IEPs between different systems or different isoforms support similar mechanisms (Karki et al. (1995) *J. Am. Chem. Soc.* 117, 3657–64; Manchester et al. (1997) *J. Am. Chem. Soc.* 119, 5069–70; and Hermes et al. (1982) *Biochemistry* 21, 5106–1428).

Isotope effects are reaction rate changes brought about by isotopic substitution. These usually carry mechanistic information. This invention is based on the comparison of relative reaction rates and enzyme kinetic constants for metabolism of CYP substrates that contain a carbon-hydrogen (C—H) bond to the metabolism of substrates that contain a carbon-deuterium (C—D) bond. A primary isotope effect refers to the rate change that is measured when the bond to the isotopic atom is broken. A secondary isotope effect refers to the rate change that is measured when the bond to the isotopic atom is not broken.

Deuterium isotope effects arise from mass differences between hydrogen (H) and deuterium (D). The frequencies (v) for the stretching of C—H and C—D bonds are around 9 and 6.3 ($\times 10^{13}$ s$^{-1}$), respectively (Isaacs, N. S. (1987) *Physical Organic Chemistry*, John Wiley & Sons, Inc., New York). The zero point energy of a bond, which is the vibrational energy remaining at 0 K, is defined by $E_v = \frac{1}{2} h\nu$, when V (the vibrational quantum number)=0, and where h=Planck's constant. The zero point energy for a C—D bond is lower than that for a C—H bond. The isotopic difference in zero point energy decreases as V increases, and approaches zero in the transition state when bond dissociation is about to occur. Therefore, more energy is required to break a C—D bond than a C—H bond.

In order to obtain mechanistic information from enzyme kinetic studies, intramolecular KIEs can be used. While this type of experimental design cannot be used for all enzymes, it is appropriate in cases where it can be used to provide a closer estimate of the intrinsic isotope effect, since the potential for masking is decreased. An intrinsic isotope effect is the maximum isotope effect for a compound, and is dependent on only the inherent physical properties of the C—D and C—H bonds (Northrop, D. B. (1975) *Biochemistry* 14, 2644–51). Rate limiting steps in an enzyme catalytic cycle that occur before the isotopically sensitive step can have the effect of reducing, or masking, the true (or intrinsic) rate difference associated with isotopic substitution.

For the intramolecular isotope effect experiments herein, a substrate is chosen that contains at least two symmetrical sites, with at least one site, but not all, isotopically labeled. A single concentration of substrate is incubated with enzyme, and the ratio of labeled to unlabeled compound in the isotopic mixture of products (or the corresponding rates of formation of products) are used to calculate a KIE.

Scheme 1 illustrates a simplified mechanism for an intramolecular isotope effect.

Scheme 1

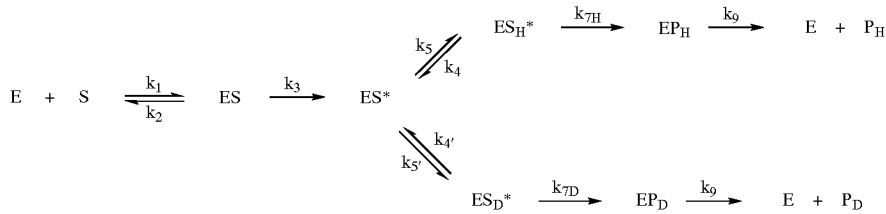

$$\left(\frac{P_H}{P_D}\right) = \frac{[ES_H^*]k_{7H}}{[ES_D^*]k_{7D}} \quad \text{(Eq. 9)}$$

$$\left(\frac{k_H}{k_D}\right)_{observed} = \frac{\frac{k_{7H}}{k_{7D}} + \frac{k_{7H}}{k_4}}{1 + \frac{k_{7H}}{k_4}} \quad \text{(Eq. 10)}$$

Rate constants $k_1$ and $k_2$ represent substrate binding to and debinding from enzyme (see step 1 in the FIG. 1 catalytic cycle). Rate constant $k_3$ is shown as an irreversible step that represents steps that occur after substrate binding, up to and including oxygen activation (steps 2–6 in the catalytic cycle, FIG. 1). An 'activated complex' between the enzyme and the substrate is formed (ES*) as a result of oxygen activation. Two possible orientations exist for the substrate in the active site (occurring between steps 6 and 7 of the catalytic cycle, FIG. 1). The orientations differ in the proximity of the H or D to the activated oxygen. Exchange between the positions is represented by the steps $k_4$, $k_4'$, $k_5'$, and $k_5$, and symbolizes rotation about the methyl group for a substrate of the form R—CH$_2$D. Product release is represented by $k_9$ (step 9 in the catalytic cycle of FIG. 1).

The observed isotope effect is the experimentally measured ratio of $P_H$ to $P_D$, and is described by Eq 9. The concentrations of the ES* species can be expressed in terms of rate constants to yield Eq 10. The intrinsic isotope effect, $k_{7H}/k_{7D}$, and the ratio of $k_{7H}$ to $k_4$ determine the observed isotope effect. Equation 10 reveals that as the magnitude of $k_4$ increases, the observed KIE will approach the intrinsic KIE. Since rotation about a methyl group is known to be fast, $k_4$ is large relative to $k_{7H}$, and the observed intramolecular KIE closely estimates the intrinsic KIE.

The 'product' of the hydrogen atom abstraction step carried out by the iron-oxygen species [FeO]$^{+3}$ in CYP can be thought of as a benzylic carbon radical, which allows one to evaluate the reaction coordinate for the hydrogen atom abstraction step. According to the Hammond postulate (Hammond, G. S. (1955) J. Am. Chem. Soc. 77, 334–40), a highly exothermic reaction will be expected to have a transition state resembling reactants, while an endothermic reaction will have a transition state more similar to products. As a substituent becomes more electron withdrawing, a benzylic radical is less stabilized. Consequently, the reaction is less exothermic (more endothermic), and the magnitude of the intrinsic isotope effect increases.

A three-center transition state complex and Melander and Westheimer's theory for the explanation of the magnitude of isotope effects (Melander, L. (1960) Isotope Effects on Reaction Rates, Ronald Press, New York; Westheimer, F. H. (1961) Chem. Rev. 61, 265–73; and Kresge, A. J. (1977) in Isotope Effects on Enzyme-Catalyzed Reactions (Cleland et al., Eds.) pp 37–63, University Park Press, Baltimore) can be used in the mechanistic interpretation of IEPs. The main concept of the theory is that the symmetric stretching vibration can supply isotope dependent zero-point energy to the transition-state, which can offset the isotope dependent zero-point energy of the ground state molecules. In a symmetrical transition-state, the force constants of the two partial bonds are equal, and the central atom is stationary. Therefore, replacing H with D will not change the moving mass, and $v_H$ will be the same as $V_D$. The isotope dependent zero-point energy difference in the transition-state will be smallest for an isothermic (symmetric) reaction, leading to the largest isotope effect. When $f_1 \neq f_2$, $v_H \neq v_D$ (i.e., for asymmetric transition states), and isotope effects will be smaller than the KIE for a symmetric reaction (Kresge, Ibid; and Cleland, W. W. (1982) Methods Enzymol. 87, 625–41).

The CYP mediated primary KIE for octane is near the maximal possible value for hydrogen atom abstraction, therefore, a symmetrical transition state and an isothermic reaction are inferred. Thus, increasingly endothermic reactions relative to octane will yield increasingly smaller intrinsic KIE, and increasingly exothermic reactions will yield increasingly smaller intrinsic KIE. A plot of KIE as a function of the extent of hydrogen transfer in the transition state would be a parabola.

An IEP consists of isotope effect measurements in a system (e.g., chemical or enzymatic) using a series of compounds that are structurally related. To determine if the mechanisms of two reactions are similar, IEPs are preferred over a single measurement since the trend in isotope effects provides additional information about the energetics of the reaction and makes fortuitous agreement between the two systems unlikely (Karki et al. (1995) Xenobiotica 25, 711–24). When intrinsic KIEs are available, comparable trends in KIE profiles between different systems argue for similar mechanisms, while different trends are indicative of dissimilar mechanisms. As described above, maximum isotope effects will be observed with reactions that have symmetrical reaction coordinates. Mechanisms with non-symmetrical reaction coordinates will yield smaller isotope effects. From this information it can be inferred that intrinsic KIEs that are measured for a series of compounds that differ in some systematic (e.g., chemical or physical) way can serve as a sensitive probe of the energetics of the isotopically sensitive step.

Figure 6:
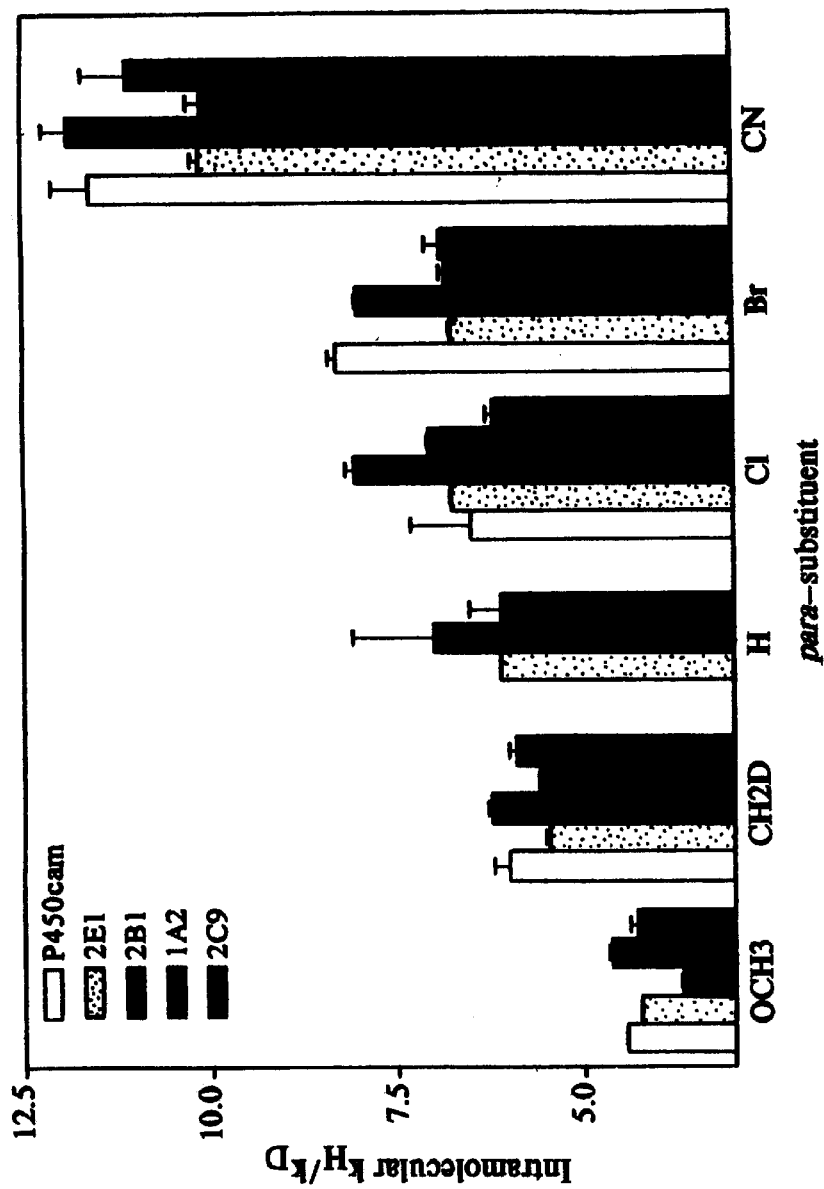
FIG. 6 shows isotope effect profiles (IEPs) for six para-substituted toluenes with expressed CYPs.

The IEPs for multiple CYP isoforms were measured in order to test the hypothesis that the active oxygen of multiple CYPs is conserved. The intramolecular isotope effects for six para-substituted toluenes (p-X-Ph-CH$_2$D: X=OCH$_3$, CH$_2$D, H, Cl, Br, CN; Ph=phenyl) using expressed CYPs 1A2, 2B1, 2E1 and 2C9 and purified P450cam are listed in Table 5. These experiments were performed with expressed CYP3A4 also, but product formation was too low to accurately measure. Isotope effects measured with substrates that contain hydrogen and deuterium bonded to the same carbon atom permit close measures of the intrinsic isotope effects (see prior discussion of intramolecular isotope effects). Table 5 shows that for each isoform, the IEPs for the toluenes are practically identical: the values range from 4–11, and the magnitudes of the isotope effects have the same rank order. In addition, for each substrate the KIE for all five CYPs are in close agreement, which exemplifies the conserved nature of the active oxygen species. The data in FIG. 6 illustrates the close agreement of intramolecular isotope effects for each substrate in multiple CYPs, which exemplifies the conserved nature of the active oxygen species.

TABLE 5

Intramolecular Isotope Effects for Six Para-Substituted Toluenes Using Various CYP Isoforms

| p-substituent | 2E1 | 2B1 | 1A2 | 2C9 | P450cam |
|---|---|---|---|---|---|
| $OCH_3$ | 4.24 (1) | 3.69 (3) | 4.64 (4) | 4.3 (1) | 4.44 (1) |
| $CH_2D^a$ | 5.45 (5) | 6.23 (5) | 5.59 (1) | 5.9 (1) | 6.0 (2) |
| H | 6.1 (1) | 7 (1) | 6.1 (4) | nd[b] | nd |
| Cl | 6.75 (2) | 8.1 (1) | 7.06 (2) | 6.2 (1) | 6.5 (8) |
| Br | 6.75 (3) | 8.02 (3) | 6.83 (8) | 6.9 (2) | 8.3 (1) |
| CN | 10.1 (1) | 11.9 (3) | 10.1 (2) | 11.1 (6) | 11.6 (5) |

Each result is the average of three determinations and the numbers in parentheses indicate the standard deviation in the last significant digit of the mean isotope effect value. [a]p-Xylene-$\alpha$-$^2H_1$-$\alpha'$-$^2H_1$ was used as the substrate. [b]Not determined due to low Levels of Product Formation The IEPs herein provide evidence for a common reaction mechanism for aliphatic hydroxylation at the benzylic position in four mammalian CYP isoforms as well as one bacterial isoform. Inclusion of P450cam into the series of IEPs is the first extension of this application to a P450 outside of the Class II P450s. P450cam belongs to Class I, which consists of P450s that interact with two electron-transfer partners. Class II members differ in that they have only one protein as a reducing partner (Peterson et al. (1995) in *Cytochrome P450: Structure, Mechanism, and Biochemistry* (Ortiz de Montellano, P. R., Ed.) pp 151–80, Plenum Press, New York). The finding that the KIE profile for P450cam is not different from the CYPs that belong to Class II is significant because it indicates that the mechanism of hydrogen atom abstraction is independent of the steps that occur prior to the irreversible formation of an active oxygen species.

These results agree with other IEP data in the literature for different groups of compounds that are metabolized by CYP. Isotope effects for a series of N,N-dimethylanilines were measured using mammalian CYPs 2B1 (purified), 4B1 and 1A2 (expressed), rat liver microsomes, and purified bacterial CYP102, and compared them to KIE in two different chemical systems (Karki et al. (1995) *J. Am. Chem. Soc.* 117, 3657–6416). Practically identical IEPs for all of the P450s and the tert-butoxyl radical system provide strong evidence for a similar mechanism of N-dealkylation, i.e., initial hydrogen atom abstraction. Furthermore, the mechanism was conserved among all the CYPs that were tested, which includes both mammalian and bacterial members of the Class II P450s. Isotope effect profiles reported for various CYPs and for tert-butoxy radical in several small molecules also support the mechanism of (initial) hydrogen atom abstraction for CYPs (Manchester et al. (1997) *J. Am. Chem. Soc.* 119, 5069–70). This abundant amount of data for both mammalian and bacterial isoforms strongly supports a common mechanism for multiple CYPs.

A comparison of all the isotope effect values for the tested substrates except toluene revealed that the means were statistically different from each other at the 0.05 significance level. This can best be explained by the fact that the standard deviations reflect the precision of the method and do not take into account systematic and day to day errors. The design of intramolecular isotope effect experiments of substrates of the form R—$CH_2D$ specifically lends itself to very precise data. The magnitude of the intramolecular KIE is independent of substrate concentration, and no internal standard is necessary for the calculation of the results.

In this regard, IEP's are enlightening. While 2B1 shows the smallest KIE for the p-$OCH_3$ compound, it gives one of the higher means for other substrates. In fact, it is obvious from FIG. 6 that no isoform consistently gives an IEP that is either high or low relative to other enzymes.

Thus for the CYP enzymes tested, the energetics of the active-oxygen species appear to be the same.

In this example, all solvents were purchased from J. T. Baker, Inc. (Phillipsburg, N.J.). Chemicals were purchased from Aldrich Chemical Co. (Milwaukee, Wis.) with the following exceptions: MTBSTFA (+1% tert-butyldimethylchlorosilane) was purchased from Regis Technologies, Inc. (Morton Grove, Ill.), and potassium phosphate dibasic and monobasic and magnesium sulfate were from EM Science (associate of E. Merck, Darmstadt, Germany). p-Chlorotoluene, p-methylanisole, and p-xylene were purified by distillation before use. p-Bromotoluene was crystallized from ethanol and p-tolunitrile was crystallized from benzene:pet ether. Gibco BRL products (Gaithersburg, Md.) were used for all cell culture methods. Biochemicals were purchased from Sigma (St. Louis, Mo.). p-Xylene-$\alpha$, $\alpha$, $\alpha$, $\alpha'$, $\alpha'$, $\alpha'$-$d_6$ (99.8% pure by GC) was purchased from Aldrich Chemical Company.

Substituted Toluene-$\alpha$-$^2H_1$ and -$\alpha$-$^2H_1$-$\alpha'$-$^2H_1$

Monodeuterated analogues of p-bromotoluene, p-chlorotoluene, p-methylanisole, and toluene were synthesized by the mesylation of the corresponding nondeuterated benzyl alcohols according to the same procedure described above for the trideuterated compounds, and p-xylene-$\alpha$-$^2H_1$-$\alpha'$-$^2H_1$ was synthesized with the same method from benzene dimethanol, except that the mole ratio of benzene dimethanol to the other reactants was 1:2.

For p-tolunitrile-$\alpha$-$^2H_1$, the benzyl alcohol was first synthesized by the reduction of p-cyanobenzaldehyde using sodium borohydride. For this procedure, the sodium borohydride (0.05 mol) was mixed with about 100 mL of ethanol and stirred under $N_2$. The aldehyde (0.025 mol) was dissolved in a small amount of ethanol and added dropwise to the NaBH4 solution. The reaction was monitored by TLC (silica gel: 50% ethyl acetate, 50% hexane). After about 1.5 h, the mixture was filtered and the solvent was evaporated. The oil that remained was mixed with water and then extracted with $CH_2Cl_2$. The organic layer was dried over $MgSO_4$ and evaporated to yield a white solid, which was recrystallized with hexane and assessed for purity by NMR and GC-MS.

Preparation of HepG2-Expressed CYP

Individual CYP isoforms (1A2, 2B1, 2E1, and 2C9) were obtained using the HepG2 vaccinia expression system described previously (Gonzalez et al. (1991) *Methods Enzymol.* 206, 85–92). Briefly, the recombinant vaccinia viruses containing cDNAs encoding a single CYP were propagated in human TK⁻ 143 (human embryoblast) cells, which were then used to infect confluent flasks of hepatoma HepG2 cells (American Type Culture Collection, Rockville, Md.). For each isoform, cells were scraped from 50 flasks, pooled, divided into 1-mL aliquots, and stored at −78° C. Microsomal preparations from crude cell lysates were obtained immediately before use according to the following procedure: aliquots were thawed, mixed with 1 mL of 50 mM KPi buffer pH 7.4, sonicated with a Branson Sonifier Model 450, and centrifuged for 15 min at 300000 g in a cold (4° C.) Beckman TL-100 ultracentrifuge; pellets were reconstituted with 2 mL of KPi buffer pH 7.4, pooled, and homogenized in a cold room. The total protein concentration of the final enzyme-buffer mixture was typically 3–4 mg mL$^{-1}$ by Bradford assay (Bradford, M. M. (1976) *Anal. Biochem.* 72, 248–54) with bovine serum albumin as the standard. The typical low levels of P450 obtained using this expression system were undetectable by CO difference spectra by the method of Omura and Sato (Omura et al. (1964) *J. Biol. Chem.* 239, 2370–8).

Cytochrome P450cam, Putidaredoxin, and Putidaredoxin Reductase

Construction of expression plasmids for P450cam, Pd, and PdR as well as protein expression and purification have been described previously (Shimoji et al. (1998) *Biochemistry* 37, 8848–52).

Incubation Conditions and Isolation of Products

All incubations using HepG2-expressed CYP were run for 20 min in a shaking water bath at 37° C. and contained the following: 300–400 μg of protein suspension, depending on the isoform; 10 mM glucose-6-phosphate, 1 mM NADP$^+$, and 1 U glucose-6-phosphate dehydrogenase as an NADPH generating system; and 1400 U catalase in a total volume of 5 mL of 50 mM KPi buffer, pH 7.4, 2 mM MgCl$_2$. For P450cam, the assays were carried out at 37° C. for 20 min in a 1-mL reaction mixture in 50 mM KPi buffer, pH 7.4, 200 mM KCl, 1.5 μM P450cam, 3 μM Pd, 1.5 μM PdR, and 0.3 mM NADH. Reactions were initiated by the addition of 50 μL (HepG2-expressed CYPs) or 10 μL (P450cam) of a substrate solution in CH$_3$CN, terminated upon addition of 3 mL of CH$_2$Cl$_2$, and 10 μL of internal standard in CH$_3$CN was added, if applicable (see below). Samples were extracted three times with CH$_2$Cl$_2$; the organic fractions were pooled, dried with anhydrous MgSO$_4$, and concentrated gently under a stream of N$_2$ to a volume of approximately 100 μL. After reconstitution with 300 μL (HepG2-expressed CYPs) or 100 μL (P450cam) of CH$_3$CN, samples were derivatized with 50 μL of MTBSTFA+1% t-BDMCS were heated overnight at 70° C.

Enzyme incubations with monodeuterated toluenes and p-xylene-α-$^2$H$_1$-α'-$^2$H$_1$ were performed in triplicate at a single substrate concentration of 0.25 mM. Controls for toluene-α-$^2$H$_1$ showed a small peak at the same retention time as product that originated from the derivatizing agent, which was quantified and subtracted from the observed amount of alcohol product. The kinetic parameters for metabolism of the substituted toluenes were determined by GC-MS analysis of the M-(dimethylsilyl) derivative of the product benzyl alcohols (see below). Control experiments using a mixture of deuterated and non-deuterated products showed that there was no isotope effect on product work-up.

Product Analysis by GC-MS

All samples were analyzed with an HP (Palo Alto, Calif.) GC-MS 5890/5972 system, equipped with an HP 7673A automatic injector. An HP-1 capillary column (25 m, 0.2-mm ID, 0.5-μm film thickness) was used for product analysis from all substrates except toluene and p-xylene, which were analyzed with an HPWax capillary column (30 m, 0.25-mm ID, 0.5-μm film thickness). For the HP-1 column, the injector and detector temperatures were both set at 250° C.; for the HPWax column, the injector and detector temperatures were 230 and 240° C., respectively. All samples were injected in the splitless mode. Oven conditions for the HP-1 column were 50° C. for 0.5 min, 10° C./min to 250° C., and 2 min at 250° C. except when p-tolunitrile was used as the substrate, in which case a gradient of 15° C./min was used. For the HPWax column the oven conditions were 50° C. for 0.5 min, 10° C./min to 240° C., and 3 min at 240° C. The MS was operated at an ionizing voltage of −70 eV and a 20-ms dwell time. Scans of authentic standards of the derivatized benzyl alcohols were used to find peak retention times and to verify products formed from enzyme incubations. Selected ion recording of the M-(dimethylsilyl) ion of products and internal standards was used to determine the amount of metabolism. The ratio of the protio and deuterio products was corrected for ion overlap and percent deuterium incorporation with Brauman's least-squares approach (Korzekwa et al. (1990) *Biomed. & Environ. Mass Spectrom.* 19, 211–7). Deuterium incorporation of substrates was measured with an HP GC-MS 5890/5970 system with an HP-1 column using the same operating conditions as above except the MS ionizing voltage was adjusted to −10.0 eV.

Data Analysis

Kinetic expressions were solved using the program Mathematica (Wolfram Research, Champain, Ill.).

EXAMPLE 3

A Linear Free-energy Relationship (LFER) Electronic Model Can Describe CYP Enzymes Given the indication that the active oxygen is very similar in multiple CYP isoforms, a single electronic model can be used to describe (the corresponding) multiple CYP enzymes. One potential model is the use of linear free-energy relationships (LFERs), which are utilized in chemistry and enzymology as a predictive tool and as a probe of the electronic characteristics of the transition state of a reaction. The following tests a second hypothesis that LFERs can be used to predict relative rates of metabolism by CYP and to evaluate physical characteristics of CYP reactions.

Relatively few LFERs have been reported for CYPs. This is not surprising given the fact that the rate-limiting step in the catalytic cycle has been shown to occur prior to the step for substrate oxidation (White et al. (1980) *Ann. Rev. of Biochem.* 49, 315–56; and Tyson et al. (1972) *J. Biol. Chem.* 247, 5777–84). Good correlation of V$_{max}$ and k$_{cat}$ values with either Hanmuett σ or oxidation-reduction potentials have been found for series of para-substituted N,N-dimethylanilines (Burka et al. (1985) *J. Am. Chem. Soc.* 107, 2549–51; and Macdonald et al. (1989) *Biochemistry* 28, 2071–7) and para-substituted sulfides (Watanabe et al. (1980) *Tetrahedron Lett.* 21, 3685–8). These data have been used to support the mechanism of electron transfer from the lone pair of the heteroatom in the substrate to the active oxygen of CYP. Similarly, hydrophobic and electronic factors were found to be good descriptors of k$_{cat}$ values for a series of para-substituted toluenes (White et al. (1986) *Arch. Biochem. Biophys.* 246, 19–32).

LFERs correlate rates and equilibrium constants. The term free energy arises from the fact that equilibrium constants (K) and rates (k) are related to free energy (ΔG=−2.303RT logK and ΔG$^\ddagger$=−2.303RT log(kh/kT)). LFERs can be used to observe the effects of substituents or solvents on the reactivity of a reaction. The degree and type of perturbation can provide mechanistic information about the chemical reaction. Rates for a reaction of interest are often compared to empirically determined constants. The most widely used empirical constants are Hammett constants. The Hammett constant σ$^+$$_{para}$ is a physical parameter that indicates the relative degree of electronic perturbation that a substituent imparts in the para position. The Hammett constant $\sigma^+_{para}$ is defined by Eq. 11 where $K_X$ is the acidity constant for a $$\rho\sigma^+_X = \log\frac{K_X}{K_H} \quad\quad (Eq\ 11)$$

para-substituted tert-cumyl chloride and $K_H$ is the acidity constant for tert-cumyl chloride (in 90% acetone-$H_2O$).

Given the above data (Example 2) supporting the concept that CYPs act with similar chemical mechanisms; the next question addressed was whether LFER can be used to predict the relative reaction rates of substituted toluenes. If relative rates of product formation are masked by other steps in an enzymatic cycle, however, LFERs must be interpreted with caution. Kinetic information can be deduced, but not mechanistic information, if relative reaction rates are masked. Therefore, it is important to assess whether or not masking occurs with the substrates chosen for a LFER analysis.

The first isoform chosen for kinetic studies was CYP2E1, since this is a low-$K_m$ isoform for small hydrophobic molecules (Guengerich et al. (1991) *Chem. Res. Toxicol.* 4, 168–79). The steady state kinetic constants $V_{max}$ and $K_m$ for benzylic hydroxylation were determined for five para-substituted toluenes (p-X-Ph-$CH_3$: X=$OCH_3$, $CH_3$, Cl, Br, CN; Ph=phenyl) using expressed CYP2E1, which displayed typical Michaelis-Menton behavior (Table 6). The choices of para-substituents allow for a range of electronic perturbation at the benzylic group, thus a LFER with the Hammett constant $\sigma^+_p$ was originally explored (Hansch et al. (1979) *Substituent Constants for Correlation Analysis in Chemistry and Biology*, John Wiley & Sons, New York). Hammett constants have been shown in other cases to correlate well with rates of hydrogen atom abstraction from substituted toluenes (Kim et al. (1985) *Tetrahedron Lett.* 26, 891–4; Sakurai et al. (1967) *J. Am. Chem. Soc.* 89, 458–60; and Heberger, K. (1994) *J. Phys. Org. Chem.* 7, 244–50).

TABLE 6

Kinetic Constants for the Formation of Para-Substituted Benzyl Alcohols from the Corresponding Para-Substituted Toluenes Using Expressed CYP2E1[a]

| para substituent | $V_{max}$[b] | S.E.[c] $V_{max}$ | V/K[d] | S.E. V/K | $r^2$[e] | n[f] |
|---|---|---|---|---|---|---|
| CN | 61.7 | 0.4 | 0.014 | 0.001 | 1 | 6 |
| Br | 58.5 | 1.3 | 0.043 | 0.005 | 0.979 | 12 |
| Cl | 50.4 | 0.8 | 0.033 | 0.002 | 0.998 | 6 |
| $CH_3$ | 58.6 | 1.2 | 0.022 | 0.002 | 0.990 | 11 |
| $OCH_3$ | 41.0 | 1.1 | 0.017 | 0.002 | 0.983 | 11 |
| Br-$d_3$ | 54.8 | 0.8 | 0.027 | 0.002 | 0.997 | 6 |
| Cl-$d_3$ | 31.4 | 1.0 | 0.020 | 0.003 | 0.991 | 6 |
| [g]$CH_3$-$d_6$ | 55.7 | 0.4 | 0.019 | 0.001 | 1 | 6 |
| $OCH_3$-$d_3$ | 18.0 | 0.3 | 0.007 | 0.001 | 0.996 | 6 |

[a]$V_{max}$ and V/K were determined by nonlinear regression. [b]Units of nM min$^{-1}$. [c]Standard error of the indicated constant. [d]Units of min$^{-1}$. [e]Correlation coefficient for the nonlinear regression fit to kinetic data. [f]Number of points used for the determination of kinetic constants $V_{max}$ and V/K. Experiments were performed with nondeuterated or trideuterated (at the benzylic position) substrates, except for p-xylene. [g]p-Xylene-α, α, α, α′, α′, α′-$d_6$ was used as the deuterated analogue of p-xylene.

Only poor correlation was found in a plot of $V_{max}$ versus $\sigma^+_p$ (Log $V_{max}$=0.11 $\sigma^+_p$+1.73; $r^2$=0.588) as well as other physical constants (data not shown), and poor correlation with V/K and various parameters. In addition to the poor correlation of $V_{max}$ and $\sigma^+_p$, the slope is positive, which is unexpected based on the rates of H-atom abstraction from toluenes using various oxygen radicals, which yield negative slopes (Kim et al., Ibid; and Heberger et al., Ibid.). A positive slope indicates that a transition state is stabilized by electron withdrawing substituents. This would normally be interpreted to mean that the transition-state is negatively charged.

Three possibilities were considered for the explanation of the poor correlations: 1) electronic parameters do not determine CYP2E1 substrate reactivity, 2) the kinetic constants ($V_{max}$ and V/K) are masked or partially masked, and 3) the transition state is negatively charged. The first two possibilities were analyzed with the appropriate methodology and the results are discussed in detail below.

Correlation of Electronic Parameters of Substrates with KDIE

First, the question of whether or not electronic factors of CYP substrates have any observable effect on the oxidation step was addressed. The natural log of the intramolecular KIEs for the six toluenes listed in Table 5 above were plotted as a function of $\sigma^+_p$ for each p-substituent. The substituent and corresponding $\sigma^+_p$ value are (respectively): $OCH_3$, −0.78; $CH_3$, 0.31; H, 0; Cl, 0.11; Br, 0.15; CN, 0.66 (Hansch et al., Ibid). In this series of substituted toluenes, it is proposed that the force constant between the benzylic carbon and the abstractable hydrogen is different for each substituent, and varies as a function of $\sigma^+_p$. The data in the poor correlation plot of $V_{max}$ versus $\pi^+_p$ (described above) support this idea. A KIE plot (of the six toluenes listed in Table 5 above versus $\pi^+_p$ for each p-substituent) demonstrated values that lie on the ascending slope of the parabolic curve described above in Example 2. It is concluded that the transition-state is sensitive to electronic effects, and that electron-donating substituents stabilize the transition-state.

KIEs and Linear Free-Energy Relationships

When LFERs are sought, experiments should be performed that definitively answer the question: is the rate of product formation masked (is product formation limited) by a rate determining step in the catalytic cycle that is not the chemical step of interest? Fortunately, innovative methods for investigation of masking in enzymatic systems were developed by Cleland and Northrop (Northrop (1975); and Cleland, W. W. (1975) *Biochemistry* 14, 3220–4). With this approach, KIEs are measured on the enzymatic parameters $V_{max}$ and V/K. Isotope effects on $V_{max}$ and V/K are expressions for the isotope effects on rates of product formation with the limiting conditions of high and low substrate concentrations, respectively.

Reported herein are deuterium isotope effects on $V_{max}$ and V/K which are designated $^DV$ and $^D(V/K)$. The expressions for both $^DV$ and $^D(V/K)$ contain the rate constant for the isotopically sensitive step, but they differ in the following ways: only $^DV$ contains the rate constant for dissociation of product from enzyme, and only $^D(V/K)$ contains the rate constants for binding of free substrate and enzyme, and dissociation of the first ES complex to free substrate and enzyme. The relative magnitudes of these steps as well as others to the isotopically sensitive step determine the degree to which the intrinsic KIE (the KIE associated solely with the bond breaking step, i.e., $k_H/k_D$) will be expressed in $^DV$ or $^D(V/K)$. Therefore, comparisons of $^DV$ and $^D(V/K)$ isotope effects to an intrinsic KIE can provide information regarding which steps, if any, are involved in masking the relative rates of product formation. These types of studies can reveal if LFERs can be used to make mechanistic conclusions. It should be noted that even if a linear relationship is seen between ln rates and descriptors for a series of compounds, it does not mean that the relative rates are unmasked.

Intermolecular KIEs were used to investigated whether or not the poor correlation of $V_{max}$ and $\sigma^+_p$ was caused by masking of $V_{max}$ by some other (slower) step in the catalytic cycle. Most enzyme catalyzed reactions contain multiple steps, and it is not uncommon for masking of reaction rates to occur. For CYP reactions, it is generally accepted that the rate limiting step is transfer of the second electron from P450 reductase to P450, a step that occurs prior to formation of product. Consequently, experimentally measured kinetic constants may be partially masked due to the presence of the slow electron transfer step unless branching to an alternate position is fast enough to unmask the intrinsic value for the kinetic constant under investigation. In summary, information gained from an enzymatic rate measurement is mechanistically meaningless if the rate is not that for the reaction step(s) of interest.

To ascertain if the $V_{max}$ values from Table 6 were masked, intermolecular isotope effects were measured and compared to the corresponding intramolecular KIE from Table 5. Isotope effect experiments of the noncompetitive intermolecular design were performed in order to evaluate the two kinetic constants $V_{max}$ and V/K. Table 7 shows that the observed KIE on both $V_{max}$ and V/K for four of the p-substituted toluenes listed in Tables 5 and 6 range from 1 to 3, while the intramolecular KIE for the corresponding toluenes in 2E1 range from 4 to 8. Since the intermolecular KIEs are smaller than the intramolecular KIEs, it can be concluded that both $^DV$ and $^D(V/K)$ are masked. The fact that $^DV_{P1}=^D(V/K)_{P1}$ values are almost identical support the fact that the external commitments to catalysis are small (see Scheme 3 and corresponding discussion).

TABLE 7

Comparison of Isotope Effects on Benzyl Alcohol Product Formation for Various Para-Substituted Toluenes Among Three Different Types of Isotope Effect Experiments

| CYP | para sub- stituent | Intra- molecular[a] $k_H/k_D$ | Intermolecular Noncompetitive[a] | | Inter- molecular Competitive[b] |
|---|---|---|---|---|---|
| | | | $^DV$ | $^D(V/K)$ | $^D(V/K)$ |
| 2E1 | Br[c] | 6.75 ± 0.03 | 1.07 ± 0.04 | 1.58 ± 0.01 | 2.06 ± 0.07 |
| | CH$_3$[d] | 5.45 ± 0.05 | 1.05 ± 0.03 | 1.19 ± 0.01 | 1.18 ± 0.03 |
| | OCH$_3$[c] | 4.24 ± 0.01 | 2.28 ± 0.10 | 2.60 ± 0.01 | 2.57 ± 0.02 |
| | Cl[c] | 6.75 ± 0.02 | 1.61 ± 0.01 | 1.62 ± 0.01 | 3.18 ± 0.62 |
| 2B1 | Cl[c] | 8.06 ± 0.12 | nd[e] | nd | 3.21 ± 0.03 |
| 1A2 | Cl[c] | 7.06 ± 0.02 | nd | nd | 2.47 ± 0.10 |

[a]The numbers after the ± sign are propagated errors. [b]Intermolecular competitive values are expressed as mean ± standard deviation of three samples. The substrate analogues used for experiments of intermolecular design were either [c]$d_0$ and $d_3$, or [d]$d_0$ and $d_6$; only benzylic position(s) were deuterated. [e]Not determined.

Intermolecular isotope effects, while usually not providing significant mechanistic information since the intrinsic isotope effect is not observed, can provide information about the kinetic mechanism. For example, this type of experiment is traditionally used to determine if a bond-breaking step is rate-limiting. An intermolecular noncompetitive KIE experiment involves the independent determination of $V_{max}$ and V/K using protonated and isotopically labeled substrates, for example, $R_1$—$CH_3$ and $R_1$—$CD_3$. For the calculation of a KIE, the kinetic constant ($V_{max}$ or V/K) pertaining to unlabeled substrate is divided by the corresponding constant for labeled substrate.

Scheme 2 shows a potential kinetic mechanism that describes an intermolecular noncompetitive KIE, and equations 12 and 13 are the expressions for $^DV$ and $^D(V/K)$ obtained for this scheme. Substrate ($S_H$ or $S_D$) combines with enzyme (E) reversibly to form the corresponding ES complex ($ES_H$ or $ES_D$). (Subscript 'H' or 'D' signifies the involvement of a compound or complex in the pathway for abstraction of hydrogen or deuterium, respectively). Formation of an 'activated'

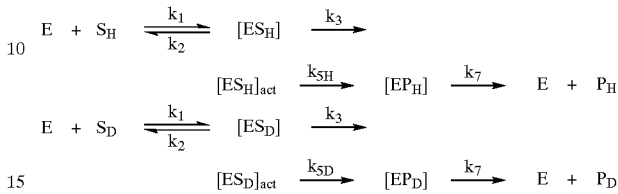

Scheme 2

$$E + S_H \xrightleftharpoons[k_2]{k_1} [ES_H] \xrightarrow{k_3}$$
$$[ES_H]_{act} \xrightarrow{k_{5H}} [EP_H] \xrightarrow{k_7} E + P_H$$
$$E + S_D \xrightleftharpoons[k_2]{k_1} [ES_D] \xrightarrow{k_3}$$
$$[ES_D]_{act} \xrightarrow{k_{5D}} [EP_D] \xrightarrow{k_7} E + P_D$$

$$D_V = \frac{\frac{k_{5H}}{k_{5D}} + \frac{k_{5H}}{k_3} + \frac{k_{5H}}{k_7}}{1 + \frac{k_{5H}}{k_3} + \frac{k_{5H}}{k_7}} \quad (Eq.\ 12)$$

$$^D(V/K) = 1 \quad (Eq.\ 13)$$

complex $ES_H^*$ or $ES_D^*$, from $ES_H$ or $ES_D$, respectively, is depicted here as an irreversible step that occurs prior to the isotopically sensitive step. This irreversible step is consistent with the understanding of the kinetic mechanism of CYP. It is a kinetic representation of a collection of steps that include: the first electron reduction ($Fe^{3+}\rightarrow Fe^{2+}$); oxygen binding and reduction; the second electron reduction of oxygen; and the heterolytic cleavage of the peroxy anion, a postulated step which is presumed to be irreversible. Product is formed at the isotopically sensitive step, producing an enzyme-product complex ($EP_H$ or $EP_D$), which is followed by dissociation of the corresponding product from the enzyme. Rate constants $k_1$, $k_2$, $k_3$ and $k_7$ may each actually represent more than one step, and inclusion of additional steps increases the complexity of the KIE equations but does not modify this analysis. When there is no pathway for alternate product formation, which is typical for most enzymes, the value of $^DV$ depends on the relative magnitudes of $k_3$ and $k_7$ to $k_{5H}$. As the rate constants $k_3$ and $k_7$ decrease relative to $k_{5H}$, $^DV$ becomes masked (see Eq. 12). $^D(V/K)$ for the noncompetitive KIE with the kinetic mechanism shown in Scheme 2, which has no branching pathway from $ES_H^*$ or the corresponding $ES_D^*$ position, is completely masked (Eq. 13).

While the $^D(V/K)$ is completely masked given Scheme 2, a branched pathway has the potential to unmask both $^DV$ and $^D(V/K)$. This is illustrated using Scheme 3, which represents the formation of two different products from one substrate, either deuterated or non-deuterated. Metabolism at an alternate, isotopically insensitive step, $k_9$, is in competition with the isotopically sensitive step, $k_7$. Rate constants $k_1$ and $k_2$ represent substrate binding to and debinding from the enzyme. Rate constant $k_3$ is shown as an irreversible step that represent steps that occur after substrate binding, up to and including oxygen activation. These steps lead to formation of 'activated complexes' (ES1* and ES2*) between the enzyme and the substrate in the relative positions 1 and 2. The active oxygen species is stable enough to permit translational and conformational changes of substrate in the active site of the enzyme.

Scheme 3

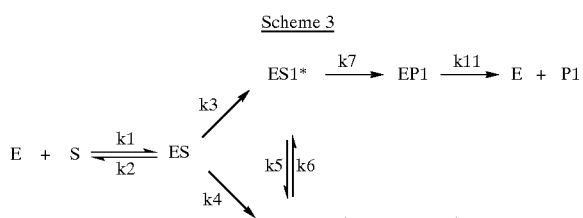

$$D(V/K)_{PI} = \frac{\frac{k_{7H}}{k_{7D}} + \frac{k_{7H}k_6}{k_5k_9} + \frac{k_{7H}}{k_5}}{1 + \frac{k_{5H}k_6}{k_5k_9} + \frac{k_{7H}}{k_5}} \quad \text{(Eq. 14)}$$

$$DV_{PI} = \frac{\frac{k_{7H}}{k_{7D}} + \left[\frac{k_{7H}k_6}{k_5k_9} + \frac{k_{7H}}{k_5}\right] + \left[\frac{2k_3k_{7H}}{k_{13}k_{7D}} + \frac{k_3k_{7H}}{k_{11}k_5} + \frac{k_3k_{7H}}{k_{13}k_5} + \frac{2k_3k_6k_{7H}}{k_{11}k_5k_9}\right]}{1 + \left[\frac{k_{7H}k_6}{k_5k_9} + \frac{k_{7H}}{k_5}\right] + \left[\frac{2k_3}{k_{13}} + \frac{k_3k_{7H}}{k_{11}k_5} + \frac{k_3k_{7H}}{k_{13}k_5} + \frac{2k_3k_6k_{7H}}{k_{11}k_5k_9}\right]} \quad \text{(Eq. 15)}$$

Consequently, it is possible for an equilibrium to be established between ES1* and ES2* (see $k_5$ and $k_6$). This is the key to unmasking KIEs. When deuterium is substituted for hydrogen at the site of metabolism, the rate constant for product formation is reduced. This can be expressed as $k_{7D}<k_{7H}$, where $k_{7D}$ represents the rate constant for oxidation at a deuterated position on a substrate, and k7H represents the rate constant for oxidation at the same position on a nondeuterated analogue of the substrate. Deuterium substitution will cause the concentration of $ES1_D^*$ to increase relative to the concentration of $ES1_H^*$ unless $ES1_D^*$ is in equilibrium with another complex, for example, the $ES^2_D^*$. If an alternate pathway does not exist, then $[ES1_D^*]>[ES1_H^*]$, and an isotope effect is masked.

Oxidation at an alternate, unlabelled position on a substrate with the formation of a second product (P2) can unmask a KIE. This is accomplished by the redirection of "excess" $ES1_D^*$ towards $ES2_D^*$ which allows $[ES1_D^*]=[ES1_H^*]$, which is necessary for the expression of a maximum, or unmasked, isotope effect. According to convention, a substrate with a low forward internal commitment to catalysis will branch from ES1 towards ES2 (Scheme 3), and isotope effects on $DV$ and $D(V/K)$ will be unmasked, depending on the magnitude of the commitment terms. The extent to which $D(V/K)$ is unmasked depends on the relative values of $k_5$ and $k_9$ to $k_{7H}$ (Eq. 14). As the rate of substrate rotation and branching increase relative to the rate of P1 formation, the rate of unmasking increases. The expression for a KIE on $DV$ for Scheme 3 is quite complex (not shown) but can be simplified to Eq. 15 with the following two assumptions. If it is assumed that reduction of oxygen is rate limiting (see prior discussion), and is significantly smaller than: (i) rotation of substrate in the active site ($k_3<<k_5, k_6$); and (ii) the rates of product formation $k_{7H}$ and $k_9$, the expression for $DV_{P1}$ is simplified to Eq. 15. If the external reverse commitment to catalysis is small ($k_{11}$, $k_{13}>>k_3$), i.e., product release is not rate limiting, and Eq. 15 reduces to Eq. 14 ($DV_{P1}=D(V/K)_{P1}$).

CYP has the potential to function as an oxidase, whereby molecular oxygen undergoes a four electron reduction, with the overall formation of two molecules of water. Formation of the second molecule of water acts as a branch point leading from the ES complex in Scheme 3, and precludes substrate oxidation. As a consequence, if branching to water is fast relative to product formation, KIEs (or rates of product formation) can become unmasked.

The rate equations 12 and 13 for an intermolecular noncompetitive KIE without branching to alternate product (see Scheme 2) can be used to interpret these results. As the relative ratio of $k_{5H}$ to $k_3$ and/or $k_7$ increases, the degree of masking of $DV$ increases. An irreversible step preceding the isotopically sensitive step, such as formation of the active oxygen species, can mask $DV$ if it is slow enough. In addition, an irreversible step following product formation, such as product release, can produce the same effect, depending on its magnitude. For a noncompetitive scheme with no branching from the activated complex $ES_H^*$ or $ES_D^*$, $D(V/K)$ will be equal to 1. Since the $D(V/K)$ KIEs observed are larger than one, branching to an alternate pathway (not shown in Scheme 2) may account for the partially unmasked values of 1.2–2.7 observed (see Eq. 13 and relevant discussion).

Branching to an alternate oxidation site(s) on the substrate, or through the pathway leading to water formation have been shown to unmask isotope effects for various compounds. With most of the substrates used in this study, it is possible that branching to water serves to slightly unmask $D(V/K)$. Benzylic hydroxylation accounts for 70% or more of the total oxidation of toluene, depending on the source of CYP, and ~95% of p-xylene metabolism. Ring hydroxylation is energetically less favorable for p-bromotoluene, p-chlorotoluene and p-tolunitrile, as compared to benzylic hydroxylation. In these cases, since metabolism at the alternate position on the substrate is slower than metabolism at the benzylic group, it cannot fully unmask an isotope effect. The data in Table 7 indicate that at least for p-methylanisole and p-chlorotoluene the intermolecular isotope effects at the benzylic position are slightly unmasked. One likely interpretation is that a small amount of branching to water is responsible for this unmasking. Furthermore, since $D(V/K)$ and $DV$ isotope effects are nearly identical, the masking must be due to high internal commitments to catalysis. The distinction between internal and external commitments to catalysis are described by Northrop (Methods Enzymol. 87, 607–25, 1982).

In order to confirm the intermolecular noncompetitive KIE data, intermolecular competitive $D(V/K)$ were measured for the same substrates using CYP2E1 (Table 7). Isotope effects of the intermolecular competitive design are simpler to perform as compared to experiments of noncompetitive design since only one concentration of each substrate (deuterated and nondeuterated) is used. In this type of experiment, both substrates are added to the same incubation mixture at a single (usually equal) concentration, and a competition between the deuterated and nondeuterated compounds is established. Only isotope effects on V/K are measured with experiments of this design.

The results of the competitively determined $D(V/K)$ for four substituted toluenes are listed in Table 7. The values of 1.2–3.2 indicate that the KIE are masked, when compared to the intramolecular KIE values for the same substrates, which range from 4 to 7. For p-xylene and p-methylanisole, the $^D(V/K)$ KIE determined competitively and noncompetitively are the same. The KIEs for p-bromotoluene determined by competitive and noncompetitive experiments are 1.5 and 2.1, respectively, and for p-chlorotoluene the values are 1.6 and 3.2. The discrepancies in $^D(V/K)$ for p-bromotoluene and p-chlorotoluene can be interpreted in terms of the kinetic constants that define the schemes for the two types of experiments. In experiments of the competitive design only, steps that pertain to debinding of both deuterated and nondeuterated substrates from one (or more) of the ES complexes can potentially unmask (or at least partially unmask) a KIE, depending on the magnitudes of the rate constants for these steps relative to others. The reason for the substrate dependence on the differences in $^D(V/K)$ for the toluenes is not known at this time, but it is certain that KIEs are masked in both types of experiments.

Competitive KIE experiments were performed for p-chlorotoluene using expressed 2B1 and 1A2 to address whether or not masking of $^D(V/K)$ occurs in other CYPs (Table 7). The V/K isotope effects were 3.1 (2B1) and 2.5 (1A2), as compared to intramolecular KIE of 8.1 (2B1) and 7.1 (1A2). The results imply that the same degree of masking occurs in all three isoforms (for p-chlorotoluene).

A number of LFER with CYP can be found in the literature. Burka et al. (*Proc. Natl. Acad. Sci. USA* 80, 6680–4, 1983) found a linear correlation between $V_{max}$ for aromatic hydroxylation and $\sigma^+$, and argued for an initial electron transfer mechanism directly from the benzene ring, for a small number of substituted monohalobenzenes. Rates of CYP-mediated N-dealkylation was correlated with oxidation-reduction potential, in accordance with Marcus theory, according to Guengerich, et al. (*J. Biol. Chem.* 271, 27321–9, 1996). Rates of S-oxygenation by CYPs were correlated with Hammett $\sigma^+$ to give a negative slope, which the authors used to argue the development positive charge in the transition state (Watanabe et al. (1980) *Tetrahedron Lett.* 21, 3685–8). White and McCarthy found a LFER with a series of substituted toluenes (*Arch. Biochem. Biophys.* 246, 19–32, 1986). Both the electronic parameter Hammett sigma, and a lipophilicity parameter correlated well with their data. However, isotope effects for a of substituted N,N-dimethylanilines by Dinnocenzo, et al (*J. Am. Chem. Soc.* 115, 7111–6, 1993) showed that isotope effects were masked, and therefore rates, were masked. The LFER and KIE data also supports the theory that rates and isotope effects are for CYP reactions are masked. In addition, the isotope effect for toluene that was measured by White and McCarthy was 2, which indicates that the rates were masked (*Arch. Biochem. Biophys.* 246, 19–32, 1986). In conclusion, it has been shown that the chemical step is masked for benzylic hydroxylation of a series of substituted toluenes. This is likely to apply to all LFERs that have been done on CYP to date.

In this example, chemicals and reagents were obtained as described in Example 2.

Synthesis of Compounds. Para-Substituted benzyl-$\alpha$-$^2H_2$ Alcohols

Methyl 4-bromobenzoate, methyl 4-chlorobenzoate, methyl 4-cyanobenzoate, methyl 4-methylbenzoate, and methyl 4-methoxybenzoate were used as starting materials for the synthesis of the corresponding para-substituted benzyl alcohols according to the following procedure. Lithium aluminum deuteride (1.2 mol) was suspended in ether and cooled to 0° C. in an ice bath while under $N_2$. The substituted benzoate (1 mol) was dissolved in a small amount of ether and added drop-wise to the LAD suspension while keeping the temperature at 0° C. After the addition, the mixture was stirred at 0° C. for an additional hour, or until complete by TLC (silica gel: 80% hexane, 20% ethyl acetate). The unreacted LAD was decomposed, and the mixture was filtered, dried over $MgSO_4$, and evaporated to dryness. The crude product was purified by recrystallization and/or distillation, and purity was assessed by NMR and GC-MS. All NMR and GC-MS data was consistent with commercially available compounds.

Para-Substituted Toluenes-$\alpha$, $\alpha$, $\alpha$-$^2H_3$ p-Bromotoluene, p-chlorotoluene, and p-methylanisole were synthesized from the corresponding p-substituted benzyl-$d_2$ alcohols according to the following method. Methane sulfonyl chloride (0.11 mol) was dissolved in a small amount of $CH_2Cl_2$ and added drop-wise to a solution of the p-substituted benzyl-$d_2$ alcohol (0.10 mol) and triethylamine (0.15 mol) in $CH_2Cl_2$ that was cooled to –78° C. in a dry ice-acetone bath. The reaction was stirred for another 30 minutes at –78° C. Because the mesylates are generally unstable, they were not isolated, and the procedure was continued by adding ice water, separating the layers, and extracting the aqueous layer with $CH_2Cl_2$. The organic layers were combined, washed with saturated sodium bicarbonate, and dried over $MgSO_4$, and the solvent was removed under reduced pressure. The oil that remained was reconstituted in ether and reduced with LAD using the same procedure as described for the reduction of the benzoates. The products were purified by chromatography (silica gel: 100% $CH_2Cl_2$), distilled under vacuum using a Kugelrohr, and, when necessary, purified again with a neutral alumina column and 100% hexane to remove any residual benzyl alcohol. Any residual benzyl alcohol was detected by select ion monitoring using GC-MS as described below.

Preparation of HepG2-Expressed CYP
   See Example 2.

Incubation Conditions and Isolation of Products

As in Example 2 and the following. Upon termination of incubations by the addition of 3 mL of $CH_2Cl_2$, 10 nmol of the appropriate internal standard (in 10 $\mu L$ of $CH_3CN$) was added, if applicable (see below).

Determinations of $V_{max}$ and $K_{max}$ for $D_0$ or $D_3$ substrates were made using at least six samples, with six different substrate concentrations in a range between 0.5 and 100 $\mu M$, and 10 nmol of the appropriate para-substituted benzyl alcohol as the internal standard. Product formation from $D_0$ substrates was measured with the corresponding para-substituted benzyl alcohol dideuterated at the benzylic carbon as the internal standard; for $D_3$ substrates the internal standard was the corresponding nondeuterated benzyl alcohol. Competitive experiments were performed in triplicate with mixtures of $D_0$ and $D_3$ substrates, each at a final concentration of 0.25 mM.

Data Analysis
   See Example 2.

EXAMPLE 4

Rapid Substrate Rotation in CYP Mediated Hydrogen Atom Abstraction Reactions

While the regioselectivity of an uncatalyzed reaction reflects the energetic differences for oxidation of the various positions in a substrate molecule, an enzyme catalyzed reaction the substrate molecule can be bound in a specific fashion to the enzyme, and bias the regioselectivity of reaction to favor a higher energy pathway than the uncatalyzed reaction. The separation of the reactivity differences intrinsic to the substrate from the steric interactions imposed by the enzyme is a challenging problem. This problem becomes particularly important when developing computational models for an enzymatic system, such as CYP, since the intrinsic reactivity differences need to be addressed with quantum chemistry, while the steric factors need to be addressed with molecular mechanics/dynamics. In this example, a method for determining if the intrinsic reactivity differences are free of CYP steric interactions is described using a combination of isotope effects and the regioselectivity of the reaction.

Figure 7:
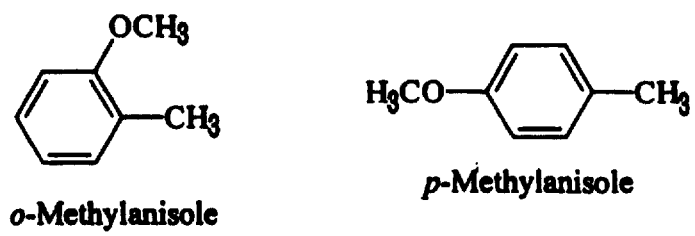
FIG. 7 shows CYP substrates used for the measurement of regioselectivity.
Figure 7:
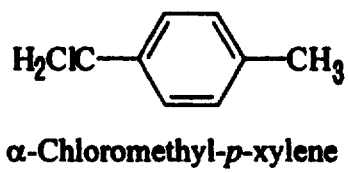

A set of small substrates were used for the development and testing of methods to determine factors that govern regioselectivity. The substrates o- and p-methylanisole and α-chloromethyl-p-xylene (FIG. 7) are relatively small, and may be free from steric constraints imposed by the enzyme active site for most CYPisoforms. Upon comparing regioselectivity and KIE data among multiple isoforms, a rank order of reactivity for the functional groups found in the substrates shown in FIG. 7 was established.

Thus a process has been established by which computational and experimental data with different energy scales can be combined to give a unified model of reactivity. This approach allows the prediction of regioselectivity and rates of drug metabolism reactions. The computational methods that can be developed from this technique allow the extension of established computational methods for hydrogen atom abstractions to aromatic oxidation and other mechanistically distinct CYP mediated reactions. Furthermore, this method will allow the incorporation of computational and experimental models for other reactions involved in drug metabolism. This approach will assist in the assessment of metabolic properties of new drugs and in the redesign of promising compounds with better metabolic characteristics.

Figure 8:
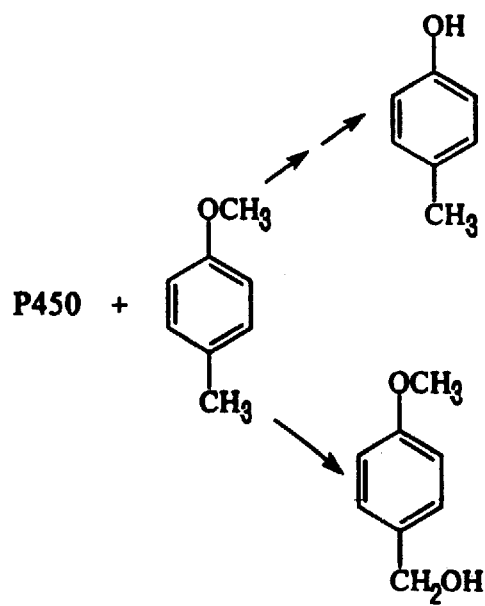
FIG. 8 shows the formation of p-cresol and p-methoxybenzyl alcohol from p-methylanisole by P450.

The schemes and the corresponding arguments in this example provide the fundamental concepts for the formulated method which allows the separation of electronic factors from steric factors for CYP-mediated enzymatic reactions. FIG. 8 illustrates the CYP-mediated formation of two potential products from one substrate. Oxidation at the functional group near the tail of an arrow leads to the formation of the product near the head of the corresponding arrow. The goal is to answer the following question: does the observed ratio of products reflect only the intrinsic electronic differences between the two functional groups, or does the protein interact with or constrain the substrate, such that the product ratio reflects both electronic and enzyme-based steric factors?

Scheme 4 illustrates a kinetic model for the formation of two products from one substrate. The details of each step and the nomenclature have been described in Example 3. It has been inferred from isotope effect experiments using various substrates and numerous CYP isoforms that the lifetime of the active oxygen permits some degree of substrate reorientation or movement after formation of the active oxygen species. Thus, ES1* and ES2* can interchange if $k_6$, and $k_6'$ >zero. In addition, an equilibrium can exist between complexes ES1* and ES2*, which is defined by the equation $(k_5/k_6)/(k_5'/k_6')$.

$$\left(\frac{[P1]}{[P2]}\right)_{observed} = \frac{k_7[ES1^*]}{k_9[ES2^*]} \qquad \text{(Eq. 16)}$$

$$\left(\frac{[P1]}{[P2]}\right)_{obs} = \frac{\frac{k_7}{k_9} + \frac{k_7}{k_6}}{1 + \frac{k_7}{k_6}} \qquad \text{Eq. 17)}$$

Equation 16 shows the relationship between the observed product ratio $(([P1]/[P2])_{observed})$ and the intrinsic ratio for the relative rates of product formation, $k_7/k_9$. (The intrinsic ratio $k_7/k_9$ can be likened to the ratio that would be observed if a chemical reaction occurred between a hypothetical $[FeO]^{+3}$ species and the substrate, in the absence of protein.) The value for the observed product ratio depends on the intrinsic ratio for the relative rates of product formation and $[ES1^*]/[ES2^*]$. Equation 16 can be rearranged to Eq. 17 upon solving for the steady-state concentrations of ES1* and ES2* (and assuming that $K_{eq}=1$). In order for the observed product ratio to accurately reflect the intrinsic differences in rates of metabolism, two criteria must be met. Criterion 1) The ES1* and ES2* complexes must be able to interchange rapidly relative to product formation, that is, $k_6 >> k_7$ in Eq. 17. Criterion 2) The equilibrium constant $K_{eq}$ for interchange of ES1* and ES2* must be equal to 1, that is, $[ES1^*]/[ES2^*]=1$, or $k_5=k_5$ and $k_6'=k_6'$.

Criterion 1 can be evaluated by assessing rates of rotation with KIEs. First, intermolecular competitive isotope effects were measured using sets of substrates that have one site of metabolism that is isotopically substituted and has at least one other site of metabolism. Scheme 5 shows a mechanism that describes an intermolecular competitive KIE for substrates that have two oxidation sites. The details of each step and the nomenclature have been described in Example 3. In Scheme 5, S1 represents nondeuterated substrate and S2 represents deuterated substrate. Oxidation occurs irreversibly at either the isotopically labeled position (through steps $k_{7H}$ for $ES1_H^*$, and $k_{7D}$ for $ES2_D^*$), or the alternate, unlabeled site (through steps $k_{11}$ for $ES1_{ALT}^*$ and $k_{11}$ for $ES2_{ALT}^*$, assuming the chemistry of this step is not isotopically sensitive).

Scheme 4

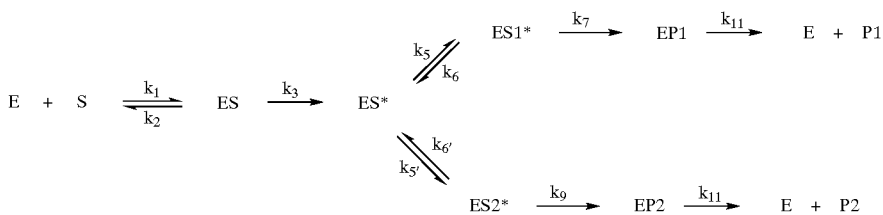

Scheme 5

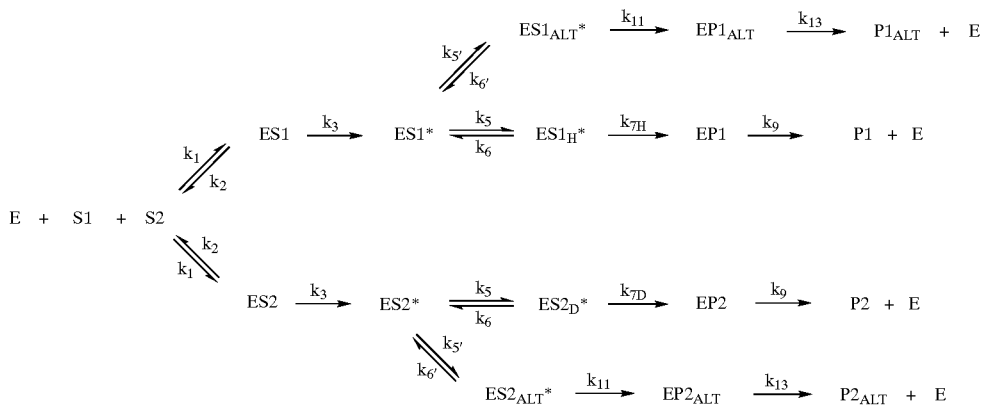

$$\left(\frac{[P1]/[P2]}{[P1_{ALT}]/[P2_{ALT}]}\right)_{obs} = \frac{\frac{k_{7H}}{k_{7D}} + \frac{k_{7H}}{k_6}}{1 + \frac{k_{7H}}{k_6}} \quad \text{(Eq. 18)}$$

Equation 18 is the kinetic expression that describes the observed, combined intermolecular competitive KIE for Scheme 5 when $k_5'>0$, and assuming $K_{eq}=1$ for both pairs of ES1* and ES2* complexes. The step $k_5'$ is a step that leads to alternate ES complex formation. The combined intermolecular competitive KIE is the ratio of the KIE for product formation at the isotopically sensitive position ([P1]/[P2]) to the KIE for the formation of the alternate, isotopically insensitive product ([P1$_{ALT}$]/[P2$_{ALT}$]). Equation 18 shows that when $k_6 \gg k_{7H}$, the combined intermolecular competitive KIE is equal to the intrinsic KIE ($k_{7H}/k_{7D}$) for that compound.

Equation 18 also describes how alternate product formation can unmask isotope effects and relative reaction rates for CYP reactions. The formation of a second molecule of water can also serve as an alternate product and therefore can unmask isotope effects. If water formation is increased upon deuteration of substrate, a large intermolecular isotope effect could be observed even if exchange is not rapid between the two ES* orientations. Rapid exchange can be confirmed by a comparison of the overall product formation from deuterated and protio substrates, independently. The degree of unmasking can be made by comparing the value for the intramolecular and intermolecular KIEs (described below).

Next, intramolecular isotope effects, which can serve as very close estimates of intrinsic isotope effects ($k_H/k_D$) when substrates are chosen that contain at least two symmetric sites, with at least one site (but not all sites) isotopically labeled, were measured. An example for the formula for this type substrate is R—CH$_2$D. A comparison of an intramolecular isotope effect to the combined intermolecular isotope effect allows the assessment of the magnitude of $k_{7H}/k_6$ in Eq. 18. If the value for the intermolecular KIE=the value for the intramolecular KIE, and total product formation does not decrease upon deuteration of substrate, it can be concluded that $k_6 \gg k_{7H}$, and that the substrate undergoes rapid rotation in the enzyme active site. If the combined isotope effect and the intrinsic isotope effect are not equal, it is possible that steric interactions hinder rotation and influence regioselectivity.

To evaluate criterion 2, the $K_{eq}$ of multiple CYP isoforms are compared. The assessment, of the regioselectivity results, is whether or not the equilibrium constant, $K_{eq}$, for the two "activated" complexes ([ES1*] and [ES2*] in Scheme 4) is equal to 1. It is possible that a preferred binding mode, imposed by the enzyme, exists for one of the two (or more) orientations of the substrate in the active site. If there was a preferred binding mode, then the concentrations of the activated complexes would not be equal. If [ES1*]/[ES2*] in Eq. 17 is not 1, then it is not possible for the observed regioselectivity to equal the intrinsic differences in rates of metabolism at the two positions ($k_7/k_9$). This concept would appear to be in violation of the Curtin-Hammett Principle if equilibrium between these two complexes were rapid. The Curtin-Hammett Principle states that if the ground state conformations are in rapid equilibrium only differences in the transition state energies of the two reaction pathways, not ground state energies, will dictate which product is formed more rapidly. However, it is assumed that poor binding in the ground state would result in poor binding in the transition-state, and would introduce a steric effect on the resulting product ratios. Thus, only enzyme-substrate complements with $K_{eq}=1$ will provide good reactivity data. An indirect method to assess if $K_{eq}=1$ is to compare a number of individual isoforms to test whether regioselectivity is constant.

In summary, if a combined intermolecular competitive KIE for a substrate that has two metabolizable positions is equal to the intramolecular KIE for that compound, then the two products are formed from kinetically indistinguishable complexes as long as water formation is not responsible for unmasking the intermolecular isotope effect. If regioselectivity is the same for multiple isoforms, there is strong evidence that $K_{eq}=1$. Hence, regioselectivity results for a large number of isoforms provides a measure of the intrinsic differences in reactivity for the two functional groups as long as $K_{eq}=1$ for the kinetically indistinguishable "activated" complexes, and water formation isn't faster than product formation. If an isoform shows deviant regioselectivity results compared to a large number of isoforms, it is likely that enzyme-substrate interactions affect the regioselectivity for the deviant isoform, and that $K_{eq} \neq 1$.

Regioselectivity of Ortho- and Para-Methylanisole

Figure 9:
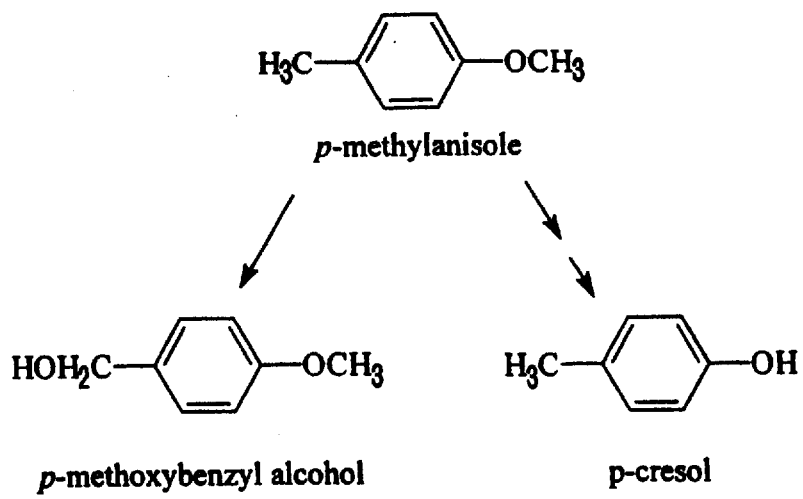
FIG. 9 shows two metabolites from the cytochrome P450 mediated metabolism of p-methylanisole.
Figure 10:
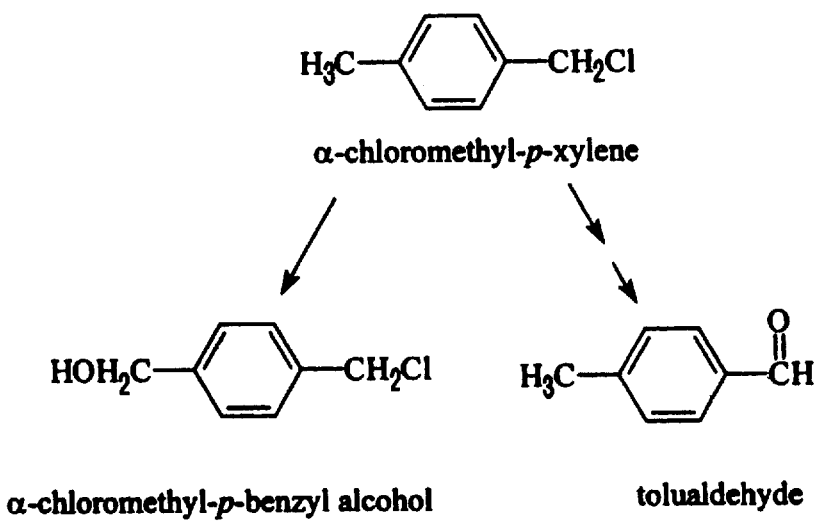
FIG. 10 shows two metabolites from the cytochrome P450 mediated metabolism of α-chloromethyl-p-xylene.

Benzylic hydroxylation (BzH) of o- and p-methylanisole (o- and p-MA) by CYP yields o- and p-methoxybenzyl alcohol, respectively. O-Dealkylation (ODAlk) of o- and p-MA yields o- and p-cresol, respectively (FIG. 9). Metabolism of the ortho isomer also yields 4-methoxy-3-methylphenol (4M3MPh) from aromatic hydroxylation. Regioselectivity was measured for d0-p-MA using expressed CYPs 1A2, 2B1, 2B6, 2C8, 2C9, 2E1 and 4B1, and the results are shown in Table 8 as the ratio of CYP-mediated BzH to ODAlk. For all isoforms that were tested, BzH is favored over ODAlk. The range of regioselectivity is from 1.3 to 20, which corresponds to a free energy of activation range ($\Delta\Delta G^{\ddagger}$) of 0.5–1.8 kcal/mol.

TABLE 8

Regioselectivity, Intermolecular Competitive (INTER) and Intramolecular (INTRA) Kinetic Isotope Effects and Calculated Primary (P) and Secondary (S) Kinetic Isotope Effects for p-Methylanisole

| CYP | Regioselectivity[a] (SD) | INTER KIE (SD) | INTRA KIE (SD) | P (PE) | S (PE) |
|---|---|---|---|---|---|
| 1A2 | 12 (2) | 5.9 (2) | 4.64 (4) | 5.0 (3) | 1.08 (5) |
| 2B1 | 2.2 (3) | 5.8 (3) | 3.69 (3) | 4.3 (3) | 1.16 (6) |
| 2B6 | 3.3 (1) | 6.8 (4) | 3.74 (3) | 4.6 (3) | 1.22 (8) |
| 2C8 | 9.5 (8) | nd[b] | nd | nd | nd |
| 2C9 | 20 (7) | 2.6 (2) | 4.3 (1) | nc[c] | nc |
| 2E1 | 4.3 (4) | 6.6 (1) | 4.24 (1) | 4.9 (1) | 1.16 (2) |
| 4B1 | 1.33 (3) | 1.42 (1) | 6.08 (3) | nc | nc |
| Avg (PE) | | 6 (1) | 4.4 (3) | 5 (1) | 1.2 (2) |
| n[d] | | 4[e] | 6[f] | 4[e] | 4[se] |

Each result is the average of either three, four, five, or six individual determinations, and the number in parenthesis indicates the standard deviation (SD) or propagated error (PE) in the last significant digit in the value.
[a]Regioselectivity is the ratio of BzH to ODAlk.
[b]Nd, not determined.
[c]Nc, not calculated because the intermolecular KIE is less than the intramolecular KIE.
[d]Number of values used for the calculation of the average.
[e]Results from CYPs 1A2, 2B1, 2B6, 2E1 used for the calculation of the average.
[f]All of the intramolecular KIE values were used for the calculation of the average.

The range of regioselectivity for o-MA, when expressed as BzH:ODAlk was 1.2–3 for CYPs 1A2, 2B1, 2C9, and 2E1 ($\Delta\Delta G^{\ddagger}$ 0.1–0.65), and for 2B6 and 4B1 the regioselectivities were 0.52 and 0.7, respectively (Table 9). The regioselectivity range, when expressed as the ratio of BzH to aromatic hydroxylation (Arom) was 0.3–0.6 ($\Delta\Delta G^{\ddagger}$ –0.7 to –0.3) for isoforms 1A2, 2B1, and 2E1, and 1.6–22 2E1 ($\Delta\Delta G^{\ddagger}$ 0.3–2) for isoforms 2B6, 2C9, and 4B1. Isoform 2C8 produced about the same amount of product from all three postitions. Ring hydroxylation products accounted for approximately 30–60% of total products for all isoforms except 2B6 and 4B1, which gave 15 and 2% phenol product, respectively (Table 9).

TABLE 9

Metabolite Profile for o-Methylanisole Expressed as Mol-%

| CYP | o-MBA | o-CR | Phenol |
|---|---|---|---|
| 1A2 | 34 | 12 | 54 |
| 2B1 | 19 | 18 | 63 |
| 2B6 | 29 | 56 | 15 |

TABLE 9-continued

Metabolite Profile for o-Methylanisole Expressed as Mol-%

| CYP | o-MBA | o-CR | Phenol |
|---|---|---|---|
| 2C8 | 31 | 36 | 33 |
| 2C9 | 46 | 22 | 32 |
| 2E1 | 27 | 16 | 57 |
| 4B1 | 39 | 59 | 2 |

Isotope Effects for ortho- and para-Methylanisole

Equal concentrations of p-MA and p-MA-$\alpha$-$^2$H$_3$ were incubated with CYPs 1A2, 2B1, 2B6, 2C9, 2E1 and 4B1 in order to measure intermolecular competitive KIEs. Identical experiments were carried out for the ortho isomers. Product formation by 2C8 was very low, most likely because o- and p-MA are poor substrates for 2C8; therefore, isotope effects could not be accurately measured for 2C8. For p-MA, a combined competitive KIE was calculated by dividing the isotope effect for p-methoxybenzyl alcohol formation by the isotope effect for p-cresol formation. The combined KIEs range from 5.9–6.8 with isoforms 1A2, 2B1, 2B6, and 2E1, and the average is 6±1 (Table 8). The values are 2.6 and 1.4 for CYPs 2C9 and 4B1, respectively. For o-MA, a combined KIE was calculated for each isoform by dividing the isotope effect for p-methoxybenzyl alcohol formation by the product of the isotope effects for p-cresol formation and aromatic hydroxylation. The values range from 9 to 14, and the average is 11±3 (Table 10).

Intramolecular KIE were measured for o- and p-MA using o- and p-methylanisole-$\alpha$-$^2$H$_1$, respectively, with CYPs 1A2, 2B1, 2B6, 2C9, 2E1 and 4B1. The average KIE for p-MA was 4.4±0.3, and the range of values was 3.69–6.08 (Table 8). For o-MA the average was 6.2±0.6, and the range of values was 5.7–6.9 (Table 9).

TABLE 10

Regioselectivity, Intermolecular Competitive and Intramolecular Kinetic Isotope Effects and Calculated Primary and Secondary Kinetic Isotope Effects for o-Methylanisole

| CYP | Regioselectivity[a] (SD) BzH: ODAlk BzH: Arom | | | | INTER KIE | (SD) | INTRA KIE | (SD) | P | (PE) | S | (PE) |
|---|---|---|---|---|---|---|---|---|---|---|---|---|
| 1A2 | 2.9 | (3) | 0.63 | (2) | 9.15 | (3) | 5.7 | (1) | 6.7 | (3) | 1.17 | (3) |
| 2B1 | 1.2 | (2) | 0.31 | (9) | 9.3 | (7) | 5.78 | (7) | 6.8 | (7) | 1.2 | (1) |
| 2B6 | 0.52 | (3) | 2.0 | (3) | 10.43 | (8) | 6.78 | (5) | 7.8 | (2) | 1.15 | (2) |
| 2C8 | 1.0 | (2) | 1.0 | (4) | nd[a] | | nd | | nd | | nd | |
| 2C9 | 2.5 | (7) | 1.6 | (9) | 12 | (1) | 6.3 | (3) | 8 | (1) | 1.2 | (2) |
| 2E1 | 1.6 | (1) | 0.48 | (6) | 10 | (1) | 5.95 | (6) | 7.1 | (5) | 1.19 | (8) |
| 4B1 | 0.7 | (1) | 22 | (2) | 14.94 | (6) | 6.90 | (5) | 8.9 | (2) | 1.29 | (2) |
| Avg (PE) | | | | | 11 | (3) | 6.2 | (6) | 8 | (3) | 1.2 | (4) |
| n[b] | | | | | 6[c] | | 6[c] | | 6[c] | | 6[c] | |

Each result is the average of three, four, five, or six individual determinations, and the number in parenthesis indicates the standard deviation (SD) or propagated error (PE) in the last significant digit in the value.
[a]Nd, not determined.
[b]Number of values used for the calculation of the average.
[c]Results from CYPs 1A2, 2B1, 2B6, 2C9, 2E1, and 4B1 used for the calculation of the average.

Primary (P) and secondary (S) KIE were calculated for o- and p-MA by the method of Hanzlik et al. (*J. Am. Chem. Soc.* 107, 7164–7, 1985) according to the equations 19–22. Here d1/d0 is equal to the observed intramolecular KIE using o- or p-methylanisole-α-$^2$H$_1$ as substrate (before statistical correction for the relative number of hydrogen to deuterium), and d0/d3 is the observed intermolecular combined KIE.

$$S = \sqrt[3]{\frac{(d0/d3)}{[(d1/d0)/2]}} \quad \text{(Eq. 21)}$$

$$P = [(d1/d0)/2]S \quad \text{(Eq. 22)}$$

Intramolecular KIE that are measured using d1 substrates are assumed to be free from masking. Intermolecular KIE measured with d3 substrates are free from masking when the value is greater than the intramolecular KIE value, therefore P and S were calculated only for isoforms that met this criteria. For p-MA, the range of P was 4.3–5.0, with an average was 5±1, and the range of S was 1.08–1.22, with an average of 1.15±0.22 for CYPs 1A2, 2B1, 2B6, and 2E1. For o-MA, the range of P was 6.7–8.9, with an average was 8±3, and the range of S was 1.15–1.29, with an average of 1.2±0.4 for isoforms 1A2, 2B1, 2B6, 2C9, 2E1, and 4B1.

Total Product Formation with D0 and D3 Substrates

Total product formation were independently measured for o- and p-MA-α-$^1$H$_3$ and -α-$^2$H$_3$ in order to assess the amount of branching for both substrates. The data in Table 11 shows the amounts of p-MBA and p-cresol formed, expressed in nmol, from the metabolism of p-MA-d0 and d3 for CYPs 1A2, 2B1, 2B6, 2C9, 2E1, and 4B1, and the products from p-MA-d0 substrate for 2C8. Metabolism of o-MA in similar experiments yields o-MBA, o-cresol, and a phenolic product identified as 4-methoxy-3-methylphenol (Table 12). For every enzyme and both of the isomeric substrates, the average amount of alcohol formed from d3 substrate is less than the amount formed from d0 substrate, and the difference is statistically significant at the 0.05 significance level. For o- and p-MA, the average amount of cresol formed from d3 substrate is statistically greater than the amount formed from d0 substrate (α=0.05), except when o-MA is metabolized by 2C9. The average amount of 4M3MPh formed from o-MA-d0 is statistically different (α=0.05) from the amount formed from o-MA-d3 with isoforms 1A2, 2B1, and 2C9. No statistical difference was observed for CYPs 2B6, 2E1, or 4B1 (α=0.05).

TABLE 11

Alcohol, Cresol and Total Product Formation from Metabolism of p-Methylanisole and p-Methylanisole-α-$^2$H$_3$ by Multiple CYP Isoforms

| CYP | substrate | nmol p-MBA (SD) | | nmol p-CR (SD) | | nmol total TP[a] (SD) | |
|---|---|---|---|---|---|---|---|
| 1A2 | D0 | 23* | (3) | 2* | (4) | 25* | (3) |
| | D3 | 13* | (2) | 8* | (2) | 21* | (3) |
| 2B1 | D0 | 4.2* | (3) | 2.0* | (3) | 6.2* | (5) |
| | D3 | 0.9* | (1) | 3.3* | (3) | 4.2* | (4) |
| 2B6 | D0 | 7.0* | (2) | 2.10* | (2) | 9.1 | (2) |
| | D3 | 2.39* | (6) | 9* | (2) | 11 | (2) |
| 2C8 | D0 | 1.89 | (3) | 0.20 | (2) | 2.08 | (4) |
| | D3 | nd[b] | | nd | | nd | |
| 2C9 | D0 | 8* | (1) | 0.42* | (9) | 8* | (1) |
| | D3 | 4.3* | (4) | 1.16* | (7) | 5.4* | (4) |
| 2E1 | D0 | 23.8* | (9) | 5.6* | (4) | 29.4 | (8) |
| | D3 | 10.6* | (7) | 18.2* | (4) | 29 | (1) |
| 4B1 | D0 | 63* | (1) | 48* | (1) | 111* | (2) |
| | D3 | 48* | (1) | 52* | (2) | 100* | (1) |

Each result is the average of three, four or five individual determinations and the number in parenthesis indicates the standard deviation (SD) in the last significant digit in the value.
[a]TP, nmole p-MBA + nmole p-CR.
[b]Nd, not determined, due to low levels of product formation.
*Denotes statistical significance between the amount of product formed from metabolism of the D0 substrate as compared to the D3 substrate (α = 0.05).

The total product (TP) formation is shown in Tables 11 and 12 for o- and p-MA as the sum of the individual amounts of products. The amount of TP formation from d0 and d3 p-MA is statistically different at the 0.05 significance level for CYPs 1A2, 2B1, 2C9, and 4B1, and are not statistically different for 2B6 and 2E1. Statistical comparison of TP from d0 and d3 o-MA (α=0.05) showed differences for CYPs 2B1, 2C9, and 2E1, and no differences for 1A2, 2B6, and 4B1.

Regioselectivity of α-Chloromethyl-p-xylene
Metabolism of α-chloromethyl-p-xylene

TABLE 12

Alcohol, Cresol, Phenol and Total Product Formation from Metabolism of o-Methylanisole and o-Methylanisole-α-$^2$H$_3$ by Multiple CYP Isoforms

| CYP | sub-strate | nmol o-MBA (SD) | | nmol o-CR (SD) | | nmol 4M3MPh (SD) | | nmol TP$^a$ (SD) | |
|---|---|---|---|---|---|---|---|---|---|
| 1A2 | D0 | 6.1* | (3) | 2.2* | (2) | 9.7* | (3) | 18.0 | (5) |
|     | D3 | 1.52* | (3) | 4.2* | (1) | 11.5* | (2) | 17.2 | (3) |
| 2B1 | D0 | 2.37* | (5) | 2.3* | (2) | 9.1* | (9) | 13* | (2) |
|     | D3 | 0.36* | (1) | 2.8* | (1) | 13* | (1) | 17* | (1) |
| 2B6 | D0 | 5.5* | (1) | 10.7* | (9) | 2.8 | (5) | 19 | (1) |
|     | D3 | 0.95* | (4) | 17* | (2) | 3.3 | (6) | 22 | (2) |
| 2C8 | D0 | 0.21 | (1) | 0.2 | (1) | 0.2 | (1) | 0.6 | (2) |
|     | D3 | nd$^b$ | | nd | | nd | | nd | |
| 2C9 | D0 | 3.1* | (3) | 1.5* | (3) | 2* | (1) | 6.9* | (9) |
|     | D3 | 0.7* | (1) | 1.4* | (3) | 1.8* | (4) | 3.9* | (6) |
| 2E1 | D0 | 6.1* | (2) | 3.8* | (2) | 13* | (2) | 23* | (2) |
|     | D3 | 0.99* | (5) | 4.7* | (2) | 13* | (1) | 19* | (1) |
| 4B1 | D0 | 18.7* | (6) | 29* | (5) | 1.1* | (5) | 48 | (6) |
|     | D3 | 3.5* | (1) | 50* | (10) | 1.9* | (5) | 55 | (10) |

Each result is the average of three, four or five individual determinations and the number in parenthesis indicates the standard deviation (SD) in the last significant digit in the value.
$^a$TP, nmole p-MBA + nmole p-CR + nmole 4M3MPh.
$^b$Nd, not determined, due to low levels of product formation.
*Denotes statistical significance between the amount of product formed from metabolism of the D0 substrate as compared to the D3 substrate (α = 0.05).

Isotope Effects for α-Chloromethyl-p-xylene

Combined intermolecular competitive KIEs were measured for α-ClMpX using equal concentrations of d0 and d3 substrates. The combined KIE is the isotope effect for the formation of α-chloromethyl-p-benzyl alcohol divided by the isotope effect for the formation of p-tolualdehyde.

The combined KIEs range from 5.5–8.8 with isoforms 1A2, 2B1, 2B6, 2E1, and 4B1 (Table 9). The amounts of p-tolualdehyde formed by 2C8 and 2C9 were very low and could not be measured in the intermolecular competitive KIEs.

Intramolecular isotope effects were measured with α-chloromethyl-p-xylene-α'-$^2$H$_1$ for seven isoforms (Table 13). The range is 6.0–8.7, and the average is 7±2. The individual contributions from the primary and secondary isotope effects were calculated for 1A2, 2B1, and 2B6, since the intermolecular isotope effects for these isoforms were not masked. The average primary isotope effect is 7±2, and the average secondary isotope effect is 1.0±1.

Total Product Formation with D$_0$ and D$_3$ Substrates

The amounts of α-chloromethyl-p-benzyl alcohol, p-tolualdehyde, and p-toluic acid were measured and total product formation was calculated after the independent incubation of α-ClMpX-α'-$^1$H$_3$ and α-ClMpX-α'-$^2$H$_3$ with CYPs 1A2, 2B1, 2B6, 2C9, 2E1, and 4B1. p-Tolualdehyde was metabolized further by three isoforms 1A2, 2B1, and 2E1 to produce small amounts of p-toluic acid. The amounts of p-toluic acid formed and the percentages of the total amounts of product formed were 1.3±0.4 nmoles (3%) for 1A2; 0.7±0.2 (3%) for 2B1; and 2.8±0.2 (10%) for 2E1. For all six isoforms, complete substitution of deuterium for hydrogen at the —CH$_3$ group caused a decrease in benzylic hydroxylation, when evaluated at the 0.05 level of significance, using the student's t-test (Table 14).

TABLE 14

Alcohol, Aldehyde, Toluic Acid and Total Product Formation from Metabolism of a α-Chloromethyl-p-xylene and α-Chloromethyl-p-xylene-α'-$^2$H$_3$ by Multiple CYP Isoforms

| CYP | substrate | nmol p-Alc$^a$ (SD) | | nmol p-Ald$^b$ + TolA$^c$ (SD) | | nmol TP$^d$ (SD) | |
|---|---|---|---|---|---|---|---|
| 1A2 | D0 | 8.7* | (3) | 41 | (4) | 50 | (4) |
|     | D3 | 1.3* | (2) | 46 | (1) | 47 | (1) |
| 2B1 | D0 | 7.9* | (5) | 14* | (2) | 22 | (2) |
|     | D3 | 1.3* | (1) | 20.0* | (4) | 21.3 | (5) |
| 2B6 | D0 | 9.2* | (5) | 7* | (1) | 16* | (1) |
|     | D3 | 1.82* | (1) | 12* | (1) | 14* | (1) |
| 2C8 | D0 | 0.11 | (1) | nd$^e$ | | nd | |
|     | D3 | nd | | nd | | nd | |
| 2C9 | D0 | 3.35* | (3) | 0.4* | (1) | 3.8* | (1) |
|     | D3 | 0.10* | (1) | 1.7* | (3) | 1.8* | (3) |

TABLE 13

Regioselectivity, Intermolecular Competitive (INTER) and Intramolecular (INTRA) Kinetic Isotope Effects and Calculated Primary (P) and Secondary (S) Kinetic Isotope Effects for α-Chloromethyl-p-xylene

| CYP | Regioselectivity$^a$ (SD) | | INTER KIE (SD) | | INTRA KIE (SD) | | P (PE) | | S (PE) | |
|---|---|---|---|---|---|---|---|---|---|---|
| 1A2 | 4.5 | (3) | 7.12 | (4) | 6.0 | (1) | 6.4 | (3) | 1.06 | (2) |
| 2B1 | 1.8 | (2) | 7.1 | (1) | 6.9 | (3) | 7.0 | (7) | 1.01 | (6) |
| 2B6 | 0.76 | (8) | 8.8 | (3) | 8.7 | (2) | 8.7 | (6) | 1.01 | (5) |
| 2C8 | nd$^b$ | | nd | | 6.2 | (7) | nd | | nd | |
| 2C9 | 0.12 | (2) | nd | | 6.7 | (2) | nd | | nd | |
| 2E1 | 5.4 | (8) | 5.5 | (2) | 6.0 | (3) | nc$^c$ | | nc | |
| 4B1 | 0.035 | (3) | 5.5 | (2) | 8.6 | (1) | nc | | nc | |
| Avg (PE) | | | 7.7 | (4) | 7 | (2) | 7 | (2) | 1.0 | (1) |
| n$^d$ | | | 3$^e$ | | 7 | | 3$^e$ | | 3$^e$ | |

Each result is the average of either three or six individual determinations, and the number in parenthesis indicates the standard deviation (SD) or propagated error (PE) in the last significant digit in the value.
$^a$Regioselectivity is the ratio of metabolism at the α-chloromethyl group to metabolisin at the benzylic position using d0-α-chloromethyl-p-xylene as the substrate.
$^b$Nd, not determined.
$^c$Nc, not calculated because the intermolecular KIE is less than the intramolecular KIE.
$^d$Number of values used for the calculation of the average.
$^e$Results from CYPs 1A2, 2B1, 2B6 were used for the calculation of the average.

TABLE 14-continued

Alcohol, Aldehyde, Toluic Acid and Total Product
Formation from Metabolism of a α-Chloromethyl-p-xylene and
α-Chloromethyl-p-xylene-α'-$^2$H$_3$ by Multiple CYP Isoforms

| CYP | substrate | nmol p-Alc[a] (SD) | | nmol p-Ald[b] + TolA[c] (SD) | | nmol TP[d] (SD) | |
|---|---|---|---|---|---|---|---|
| 2E1 | D0 | 4.5* | (4) | 25 | (4) | 29 | (4) |
| | D3 | 0.78* | (3) | 30 | (1) | 31 | (1) |
| 4B1 | D0 | 62* | (2) | 2.2* | (2) | 65* | (2) |
| | D3 | 15.2* | (5) | 1.87* | (5) | 17.0* | (4) |

Each result is the average of either three individual determinations, and the number in parenthesis indicates the standard deviation (SD) or propagated error (PE) in the last significant digit in the value.
[a]α-Chloromethyl-p-benzyl alcohol;
[b]p-Tolualdehyde;
[c]p-Toluic acid formed from the metabolism of p-tolualdehyde; p-toluic acid formation was undetectable for CYPs 2B6, 2C9, and 4B1.
[d]TP, the total amount of products was calculated by the addition of the amounts of individual products on this table.
[e]Nd, not determined, due to low levels of product formation.
*Denotes statistical significance between the amount of product formed from metabolism of the D0 substrate as compared to the D3 substrate, using the student's t-test, at a significance level of 0.05.

For CYPs 2B1, 2B6, and 2C9, alternate product formation increased upon deuterium substitution whereas for 1A2 and 2E1, the amount of alternate product formation with the —CD$_3$ substrates is not significantly different from product formation with the —CH$_3$ substrates (P=0.05). There is a small, but statistically significant decrease in the amount of alternate product formation ($\alpha$=0.05) with 4B1 when the substrate is deuterated.

Discussion

The structural/steric influence of an enzyme's architecture normally plays an important part in determining rates of product formation, regioselectivity and stereospecificity. When a large number of CYP isoforms are considered, it is easy to imagine that there is room for a great deal of variability in rates of product formation, regioselectivity and stereospecificity due to structural variability around the active site. This is true in many instances (Ortiz de Montellano, P. R. (1995) *Cytochrome P450 structure, mechanism, and biochemistry*, 2nd ed., Plenum Press, New York). On the other hand, if regioselectivity is measured for a large number of isoforms, and the results are found to be the same for all enzymes, it is possible that regioselectivity is controlled mostly by electronic factors, and the steric component is minor. If the steric component is minor, it is relatively certain that K$_{eq}$=1.

Small substrates are likely to have fewer steric interactions with an enzyme, as compared to large substrates. It is likely that regioselectivity results for a single substrate would agree for a large number of CYP isoforms when steric factors are small or absent. This statement is supported by isotope effect studies that argue for a conserved active oxygen for multiple CYPs. In addition, the relatively hydrophobic nature of the active site for most P450s reduces the possibility of strong electronic interactions between a small substrate and the enzyme.

Figure 11:
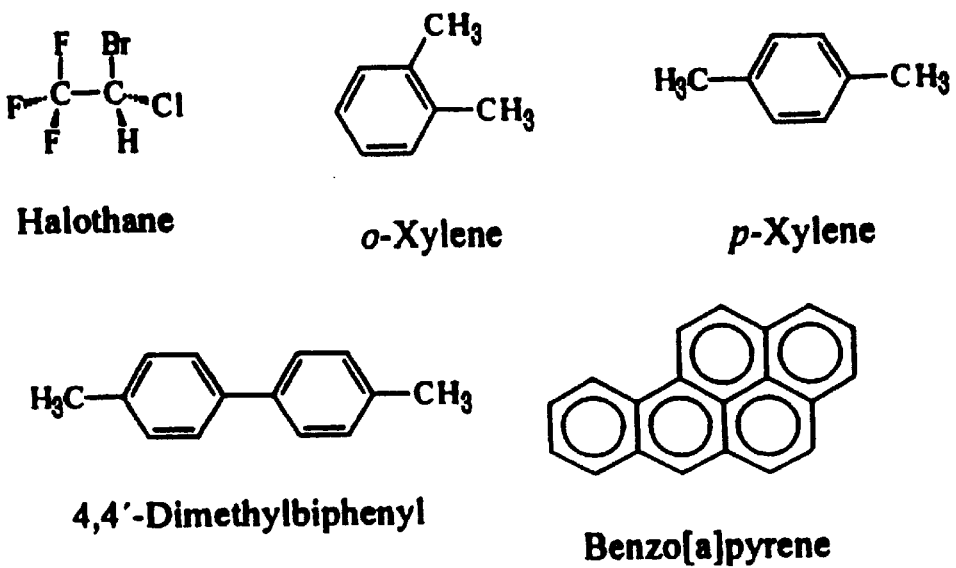
FIG. 11 shows five cytochrome P450 substrates of varying size.

Evidence in the literature for the metabolism of the compounds shown in FIG. 11 can be used to support the claim that steric factors are negligible or absent for small substrates with various CYPs. The metabolism of a group of small halogenated alkanes by CYP2E1 was described (both experimentally and computationally) by purely electronic factors (Yin et al. (1995) *Proc. Natl. Acad. Sci. USA* 92, 11076–80). Iyer, et al. used isotope effects to show that o- and p-xylene enjoyed rapid rotation in the active sites of CYPs from four sources, but that steric constraints prevented the larger 4,4'-dimethylbiphenyl molecule from moving freely in the active site (Tassaneeyakul et al. (1996) *J. Pharmacol. Exp. Ther.* 276, 101–8). Finally, Jones et al. concluded that the large molecule benzo(12)pyrene and constraints in the active sites, possibly from the I-helix, of 15 different CYPs determine the stereospecific activation of the compound (*Biochemistry* 34, 6956–61, 1995). The careful choice of small substrates in this invention allowed successful determination of which isoforms imposed active-site constraints on the substrates that were tested.

The regioselectivity of o- and p-MA and α-chloromethyl-p-xylene metabolism based on the series of isotope effect experiments in multiple CYP isoforms described above will now be discussed.

p-Methylanisole

The first step toward assessing whether or not rapid rotation of a substrate occurs in the active site of CYP is to compare intermolecular and intramolecular KIEs. For isoforms 1A2, 2B1, 2B6, and 2E1, the intermolecular KIEs for p-MA are greater than the primary KIEs, which were calculated from the intramolecular KIE values. The fact that the intermolecular KIEs are greater than the corresponding P values is not unexpected since the intermolecular isotope effects are a combination of a primary and two secondary isotope effects. The rule of the geometric mean states that isotope effects at a given reaction center are independent and multiplicative, and the data is consistent with this rule. Therefore the inter and intramolecular KIEs are equal for these isoforms.

A comparison of the amounts of total product formation for D$_0$ and D$_3$ substrates was used to assess the effect of substrate deuteration on branched pathways. Upon deuteration of the substrate at the benzylic position, the amount of p-MBA is reduced, and the amount of p-cresol is increased, and the changes are statistically significant at the 0.05 significance level, for all isoforms tested (Table 11). Total product formation for D$_0$ and D$_3$ substrates with 1A2 and 2B1 are statistically different ($\alpha$=0.05). The small differences in total product formation can be best explained by the fact that branching to water occurs. If rapid rotation occurs between the ES complexes, formation of a second alternate product only serves to unmask reactivity differences.

A number of results uphold the concept of rapid "rotation" of some substrates in the active site of CYP and no change in overall product formation upon deuteration. Lindsay Smith et al. performed experiments with anisole (*Journal of the Chemical Society Perkins Transactions II*, 621–8, 1983). Although they did not determine the intramolecular isotope effect they found that deuteration of the methyl group resulted in significant branching to para hydroxylation of anisole. This resulted in an intermolecular isotope effect of 7. This indicates that the ratios observed by these investigators might reflect the intrinsic difference in reactivity of the aromatic and demethylation pathways. Lindsay Smith et al. observed no significant change in overall turnover for the D$_3$ and D$_0$ anisole. Thus, all the branching gave the alternate product, 4-methoxyphenol, and water formation was not responsible for the large isotope effect. The relative difference in energy for p-hydroxylation of anisole and demethylation can be calculated to from the product ratios to be 0.6 kcal/mol.

Another example of efficient branching to an alternate position is the metabolism of 7-ethoxycoumarin by CYP1A2. Deuteration of the ethoxy group in the methylene position gave rise to a decrease in the deethylation pathway, an increase in aromatic hydroxylation, and no change in the overall product formation or NADPH consumption. The energy difference between the two pathways was determined to be about 1.8 kcal/mol, with O-deethylation as the favored path. The above data for 1A2, 2B1, 2B6, and 2E1 is consistent with these data found in the literature in that rapid rotation of substrate occurs in the active sites, and intermolecular KIEs are unmasked.

The data were evaluated in terms of criteria 1 and 2. Since the intermolecular KIE>primary KIE, and since the total product formation does not not significantly changed upon deuteration of the substrate, it is concluded that rotation of the substrate in the active sites of CYPs 1A2, 2B1, 2B6, and 2E1 is rapid. The regioselectivity values for isoforms 1A2, 2B1, 2B6, and 2E1 are similar, which indicates that $K_{eq}=1$. Together this data indicates that the observed regioselectivity is not influenced by steric constraints from the enzyme active site, and that benzylic hydroxylation is energetically more favorable than O-dealkylation by 0.5–1.8 kcal/mol.

The intermolecular and primary KIEs for benzylic hydroxylation of p-MA by CYP 2C9 are not equal. The most likely explanation for this observation is that the amount of branching of the metabolism to the alternate product is very low, which is indicated by the extremely high observed regioselectivity of 20:1 for BzH:ODAlk. The regioselectivity suggests a high $k_{7H}/k_5$ ratio (see Eq. 18) which can mask the KIEs and regioselectivity differences.

The inter- and intramolecular KIEs for benzylic hydroxylation of p-MA by CYP 4B1 are not equal. For 4B1, it is not likely that the amount of branching is insufficient to unmask the isotope effect since the regioselectivity, expressed as BzH:ODAlk is very low, 1.3; in fact 4B1 shows the highest amount of ODAlk relative to BzH for the series of isoforms that were tested. The reason for the nonequivalent isotope effects can be explained either by slow rotation of the substrate in the active site or steric effects from the enzyme that causes $K_{eq} \ne 1$ (with or without rapid rotation).

o-Methylanisole

The intermolecular and intramolecular KIE for o-MA with CYPs 1A2, 2B1, 2B6, 2C9, 2E1, and 4B1 are equal, which support rapid rotation of the substrate in the active sites of the enzymes. The regioselectivity, expressed as BzH:ODAlk for 1A2, 2B1, 2C9, and 2E1 ranges from 1.2–2.9, while the regioselectivity for 2B6 is 0.52 and for 4B1 is 0.7, which are clearly outliers. When expressed as BzH:Arom, the regioselectivity for 1A2, 2B1, and 2E1 are in agreement (the range is 0.3–0.6), the value for 2B6 is 2 and 4B1 is 22. The value for 2C9 has a large standard error and cannot be accurately assessed in relation to the other isoforms. The results suggest that $K_{eq}=1$ for o-MA with 1A2, 2B1, and 2E1 but not with 2B6 or 4B1. Thus steric constraints on o-MA due to the enzyme active site are apparently absent in 1A2, 2B1, and 2E1, and the rank order of reactivity is aromatic hydroxylation>benzylic hydroxylation>O-dealkylation. This data agrees with the data for p-MA and CYPs 1A2, 2B1, 2B6, and 2E1 in that benzylic hydroxylation is energetically more favorable than O-dealkylation.

When the ratio of branching increases relative to metabolism at the benzylic position with the ortho isomer, the inter- and intramolecular KIE for 2C9 are unmasked, and the regioselectivity results agree with the majority of the data for the other isoforms in that BzH is preferred over ODAlk. Deuteration of the substrate does not cause a significant increase in alternate product o-cresol, and the average amount of 4M3MPh is 2 for d0 substrate, and 1.8 for d3 substrate, a small or negligible change. Total product formation for o-MA-d3 is approximately half of the value for the d0 substrate. It is possible that branching to water is responsible for unmasking the intermolecular KIE for o-MA and 2C9.

Inspection of the data for o-MA with 4B1 shows interesting results. The intermolecular isotope effect is not masked and total product formation for d0- and d3-substrates is equal. However, the regioselectivity is the opposite of the values observed for the majority of isoforms and substrates. It is probable that rapid rotation of the two functional groups in the active site occurs since the benzylic and methoxy groups are in close proximity to each other. Therefore, it is not surprising that the intermolecular isotope effect is unmasked for 4B1. The fact that the amount of phenol product from o-MA is extremely low together with the inverse regioselectivity results, expressed as BzH:ODAlk, suggest that $K_{eq} \ne 1$ or, in terms of the Curtin-Hammett principle, the transition-state for benzylic hydroxylation is sterically hindered.

It is proposed as part of the invention that the active site of 4B1 may have a narrow channel over the heme, which does not permit fast rotation of the substrate para-MA, but which allows the p-MA to translate away from the heme, flip over, and translate back towards the heme. The proposed narrow channel can accommodate either of the two functional groups, but accommodates the methoxy group better. This is indicated by (i) the fact that regioselectivity for p-MA shows the lowest value when compared to the majority of isoforms tested, and (ii) metabolism of the methoxy group is preferred over metabolism of the benzylic group for o-MA, which is opposite to the results for the majority of isoforms. Almost no ring hydroxylation is observed when o-MA is metabolized by 4B1, in contrast to other isoforms. This also supports the idea of a preferred binding mode.

It has been suggested that the presence of an amino, substituted amino group, or an oxygen atom may confer substrate specificity for 4B1 (80). The presence of a positively charged amino acid in the active site of 4B1, near the heme, may confer an electrostatic component to the binding and regioselectivity. A positive charge could interact with either N or O in the substrates, and bias the position of the substrate in the active site.

The isotope effect results for o-MA with 2B6 suggest that the substrates undergo rapid rotation in the active site. However, the regioselectivity values for 2B6, when expressed as BzH:ODAlk and BzH:Arom, are opposite to the regioselectivity values for 1A2, 2B1, and 2E1. Data in the literature agrees with the results disclosed herein. Metabolism of toluene by expressed 2B6 gave a high ratio of BzH:ODAlk when compared to other isoforms. It is proposed as part of the invention that the active site of 2B6 is large enough to allow for the rapid rotation of para-MA and that 2B6 has a narrow channel in the active site near the heme. The narrow channel is responsible for constraining the ortho isomer of MA in one orientation. In conclusion, the present data suggests that $K_{eq} \ne 1$ for the o-MA-2B6 complex.

An additional observation of the present regioselectivity data for o-MA is that the ratios of ring hydroxylation para to the methoxy group to ODAlk, according to isoform, are 4.5(1A2), 3.5(2B1), 1.5(2C9), and 3.5(2E1). These data are similar to the ratios of p-hydroxyanisole to phenol (average ratio=2.9) that were observed when anisole (Ph-OCH$_3$) was metabolized by four microsomal systems. The present data and Lindsay Smith's data are in contrast to the ratios of ODAlk:Arom measured herein for 2B6 and 4B1, which are 0.3 and 0.03, respectively. This lends additional support to the hypothesis that steric factors contribute significantly to the observed-regioselectivity and KIEs for o-MA with 2B6 and 4B1.

Figure 12:
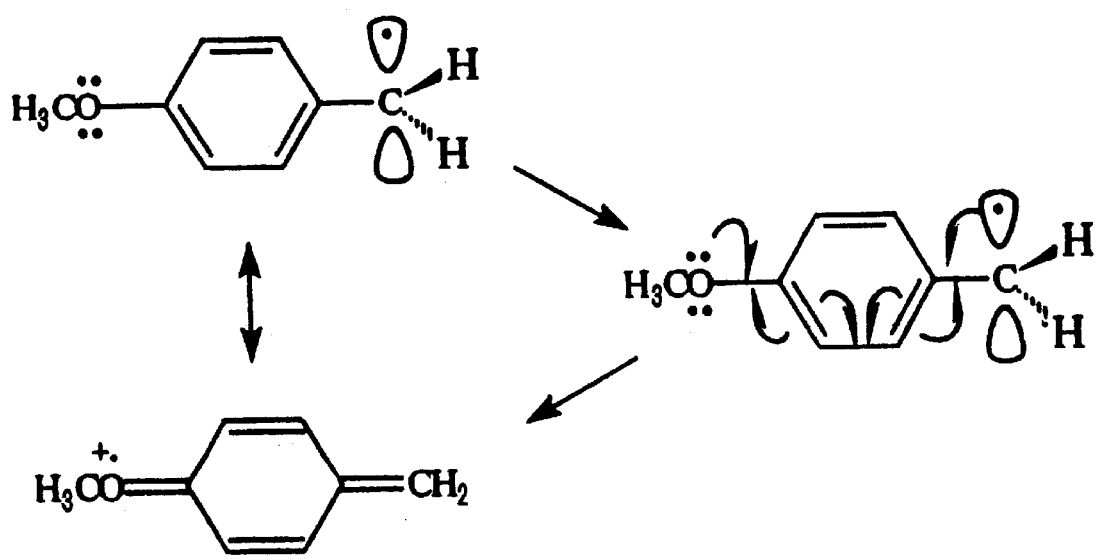
FIG. 12 shows resonance stabilization towards a carbon based radical for o-methylanisole.

The degree of symmetry in the transition-state can be assessed using the P values calculated from the intramolecular KIEs for metabolism at the benzylic position. The average P value for p-MA with CYPs 1A2, 2B1, 2B6, and 2E1 is 5±1, and the average P for o-MA is 8±3. The average P value for octane was 7.6, which was postulated to have a symmetrical transition-state (Jones et al. (1987) *J. Am. Chem. Soc.* 109, 2171–3). The average P value for p-MA of 5 implies an asymmetric transition-state and an exothermic reaction relative to H-atom abstraction from octane. The average P value for o-MA suggests a symmetrical transition state. It is suggested as part of the invention that the p-methoxy group provides resonance stabilization in the transition-state and accounts for the lower P value for p-MA as compared to the P value for octane (see FIG. 12).

The reason for the differences in the average intramolecular KIEs for o- and p-MA is not known, but is most likely explained by the fact that the two isomers are electronically different. According to the Melander and Westheimer (Melander, L. (1960) *Isotope Effects on Reaction Rates*, Ronald Press, New York), the magnitude of an intrinsic KIE is governed by the symmetry of the transition-state. Therefore, the present data indicates that the transition-state for the carbon-hydrogen bond breakage of p-MA is earlier than the transition-state for o-MA. Based on the Hammond postulate, the reaction for p-MA is more exothermic, and the product is more stable, when compared to o-MA. This comparison is based on the assumption that the transition states for both isomers are linear, which may not be true since steric hindrance in the ortho compound could induce a non-linear transition state. But the effect of a non-linear transition-state would be expected to lower an isotope effect. If the para compound is used as a reference (and was linear) the ortho isomer would be expect to have a lower intrinsic KIE as compared to the para isomer. It is possible that resonance effects may be responsible for differences in stabilization of the ortho and para reactants and products, and thus the different KIEs.

α-Chloromethyl-p-xylene

The results in Table 13 show that the intermolecular KIE≡primary KIE. Rapid rotation of the substrate in the active site is inferred for CYPs 1A2, 2B1, and 2B6. Among these three isoforms, 1A2 and 2B1 show similar regioselectivity results. Total product formation is not decreased upon deuteration of substrate for 1A2 and 2B1; therefore water formation is not responsible for unmasking the KIE. For 1A2 and 2B6, it is concluded that $K_{eq}=1$, and that metabolism at the α-chloro-methyl group is energetically more favorable than at the benzylic position by 0.36–0.93 kcal/mol.

The preference for metabolism at the α-chloro-methyl group, as compared to the benzylic position, is the predicted preference based solely on a comparison of the stability of the resultant radical products of hydrogen atom abstraction. The product formed from hydrogen atom abstraction at the carbon atom adjacent to the Cl is resonance stabilized by Cl atom. Weaker, inductive effects from the para-positioned benzylic group stabilize the product formed from hydrogen atom abstraction at the —$CH_3$ group.

While the isotope effect results for 2B6 indicate rapid rotation of the substrate in the active site, the regioselectivity data suggest that steric constraints in the active site are significant. This is based on comparison of regioselectivity results to the results for 1A2 and 2B1. The results also correlate with the results for interaction of o-MA with 2B6, which suggested binding-site restrictions.

The regioselectivity data for 2C9 cannot be assessed for rapid rotation, but an interesting point can be made based upon a comparison of the results to the observed regioselectivity for p-MA. Metabolism at the —$CH_3$ group of p-methylanisole and α-chloromethyl-p-xylene by 2C9 is highly favored over metabolism at the positions para to this methyl group, by 20:1 and 8:1, respectively, when compared to most of the other isoforms that were tested. It is possible that the proposed region of positive charge in the active site of 2C9 (Jones et al. (1996) *Drug Metab. Dispos.* 24, 1–6) interacts with the lone pair(s) of electrons from the oxygen in the methoxy group and the chlorine in the α-chloromethyl group. This would act to keep the substrates contained, and subsequently influence the regioselectivity results by this electrostatic interaction.

The intermolecular KIE is not equal to the intramolecular KIE for 2E1, which indicates that rotation of the substrate is not fast in the active site. Incubation of the ortho isomer of this compound would potentially permit rapid exchange of the substituents in the active site, and would allow the assessment of regioselectivity results without steric or other constraints.

The isotope effect results for 4B1 signify that rotation of the substrate is not rapid. The regioselectivity data shows a drastic preference for benzylic hydroxylation to metabolism at the α-chloromethyl group, the preference is ~30:1. Deuteration of the substrate shows a statistically significant, but very small, decrease in alternate product formation, from 2.2 nmol to 1.87 nmol. The regioselectivity and noncompetitive product data suggest a large structural constraint imposed by the enzyme. Another possibility for potential 4B1-substrate interaction is the presence of a positively charged region in the active site. This idea was used to explain the regioselectivity data for o-MA, and 4B1 substrates preferences (Blaise Smith et al. (1995) *Biochem. Pharmacol.* 50, 1567–75). A list of known 4B1 substrates contains compounds that usually have an amino group, a substituted amino group, or an oxygen atom.

The accurate determination of whether or not $K_{eq}=1$ (criterion 2) is the most challenging element of the use of the disclosed methodology for separating electronic and steric factors. The present invention's method of comparing regioselectivity values for multiple isoforms is an indirect method. While the invention concludes that the concept is valid, there are some potential shortfalls. The technique requires the use of a large number of isoforms for metabolism studies. If compounds are not good substrates for a large enough number of isoforms, the sample size for assessing criterion 2 will be small. If regioselectivity values vary widely for a small sample size, it may not possible determine which isoform(s), if any, impose steric constraints on the substrate.

Among the present data for α-chloromethyl-p-xylene, only three isoforms (1A2, 2B1, and 2B6) show rapid rotation of the substrate in the active site, as judged by the comparison of intermolecular and intramolecular isotope effect values. Regioselectivity values for two of the three isoforms were in agreement (1A2 and 2B1), and the other isoform (2B6) showed the opposite regioselectivity value. With a sample size of only three, it is difficult to prove that the two isoforms whose values agree are not outliers, and that the distinct value does not represent a larger set of consensus data. However, information was gained by the comparison of groups of data from multiple substrates. For instance, it was concluded that isoforms 2B6 and 4B1 imposed structural constraints on the substrate o-methylanisole, and the data for α-chloromethyl-p-xylene was evaluated with this information in mind. For both o-methylanisole and α-chloromethyl-p-xylene, the regioselectivity data for isoforms 2B6 and 4B1 agree, and in both cases the regioselectivity values indicate that metabolism occurs more often at the less energetically favorable site (judging from the predicted stability of the proposed carbon based radical product). The consistency of the data lends support to the invention. Regioselectivity values and isotope effect experiments with additional isoforms as well as additional substrates can be obtained in order to strengthen the initial hypotheses.

From these results, as well as the results of Lindsay Smith et al. (*Journal of the Chemical Society Perkins Transactions II*, 621–8, 1983) and Harada et al. (*J. Biol. Chem.* 259, 3005–10, 1984), a rank order of reactivity of functional groups that are metabolized with freedom from structural constraints from the apoprotein can be established. The following order of reactivity: α-chloromethyl hydroxylation>benzylic hydroxylation>O-deethylation>aromatic oxidation>O-dealkylation is predicted. While Lindsay Smith et al. and Harada et al. did not perform a rigorous set of isotope effect experiments to check for rapid rotation of substrate, stoichiometric results from both data sets indicated that rapid rotation was likely.

In summary, a methodology for determining whether the electronic component of CYP-mediated reactions are free from the structural component has been developed. The relatively small size of these substrates is partially responsible for the success of this model. Electronic models correctly predict the primary site of metabolism for about 80% of substrates. For CYP enzymes that do not permit rapid rotation of substrates, an electronic component still exist in combination with the steric component. As such, electronic models are still required in predictive models for most CYP enzymes.

The regioselectivity results from these experimental studies can be compared to, and used for the validation of existing computational or chemical methods for predicting CYP reactions. In addition, the experimental data can be used to help refine computational models, and as guidelines for the development of new models. Ultimately, methods for predicting the electronic component to reactivity can beicombined with methods for predicting the influence of protein structure on metabolism. Ideally, this will allow for the construction of complete, more accurate models, that is, models that will incorporate the influence of both electronics and steric factors, without imposing limits on substrate size.

In this example, chemicals and reagents were obtained as described in Example 2.

Synthesis of Alcohols and Toluenes

Methyl 4-methoxybenzoate and methyl-2-methoxybenzoate were used as starting materials for synthesis of the corresponding substituted benzyl-α-$^2H_2$ alcohols, and substituted toluenes-α, α, α-$^2H_3$ and -α-$^2H_1$ were synthesized from the corresponding $D_2$ and $D_0$ alcohols, respectively, and purified according to the procedures described in Examples 2 and 3

Synthesis of 4-Methoxy-3-methyl-phenol

The synthesis for the phenol was a two step synthesis via the Vilsmer-Haack condensation to obtain the aldehyde and then by the Baeyer-Villiger oxidation to give the phenol. Phosphorus oxychloride (5.1 mL, 0.057 mol) was added the dropwise to a solution of 2-methylanisole (5.33 mL, 0.043 mol) in dimethylformamide (6 g) under nitrogen. After addition, the mixture was heated and refluxed for 4 h, cooled then added to 100 mL of water. An excess of 10% NaOH was added and the solution was extracted with 4×100 mL of ether. The ether layers were washed with water and then brine solution, dried over magnesium sulfate and evaporated under reduced pressure. The dark oil that remained (5.0 g, 77%) was purified by column chromatography (silica gel: 90% hexane, 10% ethyl acetate). The remaining oil (1.78 g, 28%) was dissolved in dichloromethane (100 mL) and then 3.03 g, (0.018 mol) 3-chloroperbenzoic acid was added. The mixture was refluxed under nitrogen for ~5 h, cooled, and then evaporated under reduced pressure. The residue was dissolved in ethyl acetate and washed with aqueous saturated sodium bicarbonate. The organic layer was dried over magnesium sulfate and evaporated under reduced pressure. The dark oil that remained was dissolved in 7 mL of methanol and 5.5 mL of 10% aqueous potassium hydroxide solution was added. The solution was stirred under nitrogen for ~2 h, water was added, and the solution was extracted with ether. The ether layers were combined and washed with saturated sodium bicarbonate solution and then with water. The ether was dried over magnesium sulfate and evaporated under reduced pressure. The oil that remained (1.21 g, 74%) was recrystallized twice with hexane to give long white needles (0.34 g, <1%). The purity was assessed by NMR and GC-MS.

Synthesis of α-Chloromethyl-p-benzyl-α-$^2H_2$ Alcohol

To a solution of 4-(chloromethyl)benzoic acid (2.5 g, 0.015 mol) in ether was added an excess of diazomethane in ether. After the excess of diazomethane had evaporated from the reaction, the ether was evaporated under reduced pressure leaving solid (2.68 g, 99% crude yield) which was then dissolved in ether and added dropwise to a solution of lithium aluminum deuteride (0.73 g, 0.017 mol) in ether cooled to 0° C. A white semi-solid was isolated (2.31 g, 99%) after work-up as per the para-substituted benzyl-α-$^2H_2$ alcohols in Example 2. This compound was used without further purification.

Synthesis of α-Chloromethyl-p-benzyl Alcohol

The reaction was performed using the same method as the method described above for the synthesis of α-chloromethyl-p-benzyl-α-$^2H_2$ alcohol, except lithium aluminum hydride was replaced with lithium luminum deuteride (82% yield).

Synthesis of α-Chloromethyl-p-xylene-d3 and α-Chloromethyl-p-xylene-d1

These were prepared in the same manner as the methylanisoles. The oils that remained were first purified by silical gel column chromatography (100% hexane) and then an alumina column (100% hexane).

Preparation of HepG2 Expressed CYP, Incubation Conditions, Controls, Product Isolation, and Data Analysis The methods and details of protein expression and preparation for isoforms 2B6, 2B8, and 4B1, incubation conditions, sample work-up, and data analysis were the same as described above in Example 2 except for the following details. Competitive isotope effect experiments were performed in triplicate with mixtures of $D_0$ and $D_3$ substrates, each at a final concentration of 0.125 μM. The independent measurements of product formation from $D_0$ and $D_3$ substrates were performed at final concentrations of 0.25 μM. Product formation from $D_0$ substrates was measured with 10 nmol of the corresponding substituted benzyl alcohol dideuterated at the benzylic carbon as the internal standard; for $D_3$ substrates the 10 nmol of the corresponding nondeuterated benzyl alcohol internal was used as the standard. o-Cresol, p-cresol, and 4-methoxy-3-methylphenol were quantified with 20 nmol of p-bromobenzaldehyde as the internal standard, against a standard curve. A small amount of background o- or p-cresol was quantified and subtracted from the observed amount of the corresponding cresol product.

Product Analysis by GC-MS

An HP-1 column was used for product quantification with the same GC-MS run conditions as those stated in the Experimental section of Chapter II except the oven conditions were 50° C. for 0.5 min, 10° C./min to 145° C. and 20° C./min to 250° C., and 2 min at 250° C. An HPWax column was used for the identification of 4-methoxy-3-methylphenol. Refer to Example 2 for the remaining details.

Identification of o-Methylanisole Metabolites

Three product peaks were observed after GC-MS analysis of samples from incubations of o-methylanisole and CYP. Two of the peaks were unambiguously identified as 4-methoxybenzyl alcohol and o-cresol by comparison to authentic standards. A third peak for all isoforms exhibited mass spectral fragment patterns and GC retention times on both HP-1 and HPWax columns that were identical to the authentic compound 4-methoxy-3-methylphenol. Since a mass spectral fragment pattern is normally unique for any given chemical, the third peak has been labeled 4-methoxy-3-methylphenol.

However, authentic compounds corresponding to the three other possible phenolic regioisomers were not available for comparison to the third peak. If the mass spectral fragment patterns, retention times, and area counts relative to internal standard are the same for all four isomers, then the data for 4-methoxy-3-methylphenol represents a sum of the ring hydroxylation products. All o-MA incubation samples were analyzed on an HPWax column, which is more polar than an HP-1 column. The HPWax column was used to separate peaks for other isomeric compounds that normally overlap on an HP-1 column. Analysis of all o-MA incubation samples on the HPWax column did not result in any degree of peak separation. Therefore, it is reasonably certainty that the third product is 4-methoxy-3-methylphenol.

Statistical Analysis

All statistical analysis was performed with the student's t-test assuming equal variances using the Data Analysis Toolpak in Microsoft Excel 97.

EXAMPLE 5

Regioselectivity as a Measure of Relative Rate Constants for Hydrogen Atom Abstraction As explained above, experimental metabolite ratios may be used to parameterize the theoretical model for CYP reactions given rapid rotation of the substrate, indicating the absence of enzyme imposed steric constraints. An additional means of confirming such rapid rotation in CYP enzymes is by examination of the relative rates of benzylic hydroxylation and O-dealkylation of 4-methylanisole. The observed ratio of products from the two reactions permits confirmation of whether the reactions can be simply modeled with electronic factors.

Table 15 demonstrates that for reactions on 4-methylanisole by various CYP enzymes, rapid rotation rates are present.

TABLE 15

The regioselectivity, and inter- and intramolecular kinetic isotope effects for 4-methylanisole

| Enzyme | Benzylic/ O-Dealkylation | δΔG$^†$ (kcal/mole) | Intramolecular KIE | Intermolecular KIE |
|---|---|---|---|---|
| CYP2E1 | 5.41 | 1.06 | 4.02 | 6.53 |
| CYP3A4 | 12.83 | 1.61 | 5.27 | 2.76 |

TABLE 15-continued

The regioselectivity, and inter- and intramolecular kinetic isotope effects for 4-methylanisole

| Enzyme | Benzylic/ O-Dealkylation | δΔG$^†$ (kcal/mole) | Intramolecular KIE | Intermolecular KIE |
|---|---|---|---|---|
| CYP2B6 | 3.93 | 0.86 | 4.58 | 7.60 |
| CYP2C8 | 8.26 | 1.32 | 3.60 | 3.60 |
| CYP2C9 | 19.62 | 1.87 | 3.92 | 3.52 |
| CYP1A1 | 5.91 | 1.12 | 4.23 | 2.17 |
| CYP1A2 | 17.98 | 1.82 | 3.79 | 5.94 |
| Mean | 10.60 (5.85) | 1.38 (0.39) | 4.20 | 4.59 |

In addition to the normal isotope effects observed for the benzylic hydroxylation reactions, inverse isotope effects are observed for demethylation. This indicates that the rate of interchange of the methyl and methoxy groups is fast for most enzymes tested. All enzymes favor benzylic oxidation, with an average different in $\Delta G^†$ of 1.3 kcal/mole. This standard deviation is within the predictive error of the models. Thus, this data further supports the use of experimental metabolite ratios to provide relative rate constants for oxidation of different functional groups.

To parameterize hydrogen atom abstraction, the results of a recent study proved exciting, not only in terms of mechanistic insight but because it presented with a potential apoprotein independent model for CYP mediated reactions. While studying the mechanism of N-dealkylation reactions, a number of experiments were conducted with the well characterized hydrogen atom abstractor t-butoxy radical. These studies extended previous work by others which uses a laser to flash photolyze t-butylperoxide to t-butoxy radical. The classic method uses diphenylmethanol to follow the rate of hydrogen atom abstraction of a competing reaction.

Of particular interest was comparing the isotope effect profiles for t-butoxy radical hydrogen atom abstraction, the deprotonation of a radical cation after outer-sphere electron transfer and CYP mediated reactions. It was found that not only were the isotope effect profiles similar, they were essentially identical for the t-butoxy and CYP mediated reactions with substituted dimethylanilines. This led to the hypothesis that t-butoxy radical is a good model for CYP mediated reactions in general.

Figure 14:
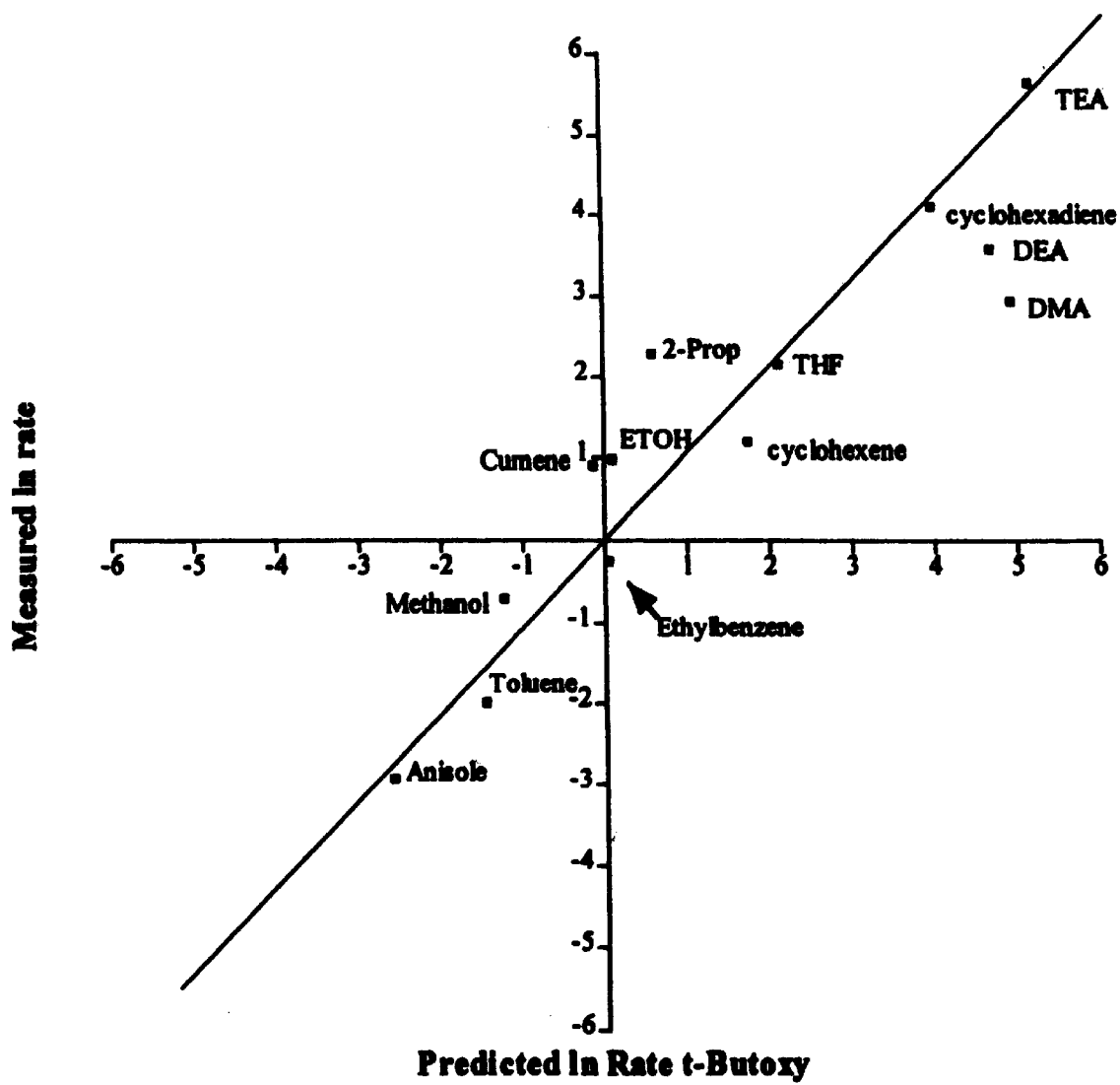
FIG. 14 shows a correlation between experimental reaction rates with t-butoxy radical and DFT energies.

Using BLYP/6-31G* density function methods to obtain ground state descriptors the linear relationship (see Equation 24 and FIG. 14) between 14 experimentally measured rate constants (ln rate) for hydrogen atom abstraction by t-butoxy radical and the BLYP/6-31G* heat of reaction ($H_{reac}$) and radical intermediate HOMO energy in kcau/mol ($E_{HOMO}$) was obtained. The standard error of the estimate for this correlation is around 0.9 kcal/mole (see FIG. 14).

$$\ln \text{rate} = 12.43 + 0.22(\Delta H_R) + 1.84(E_{HOMO}) \qquad \text{Eq. 24}$$

These results support the use of chemical systems to experimentally parameterize computational models.

EXAMPLE 6

Regioselectivity as a Measure of Relative Rate Constants for Aromatic Oxidation

Figure 13:
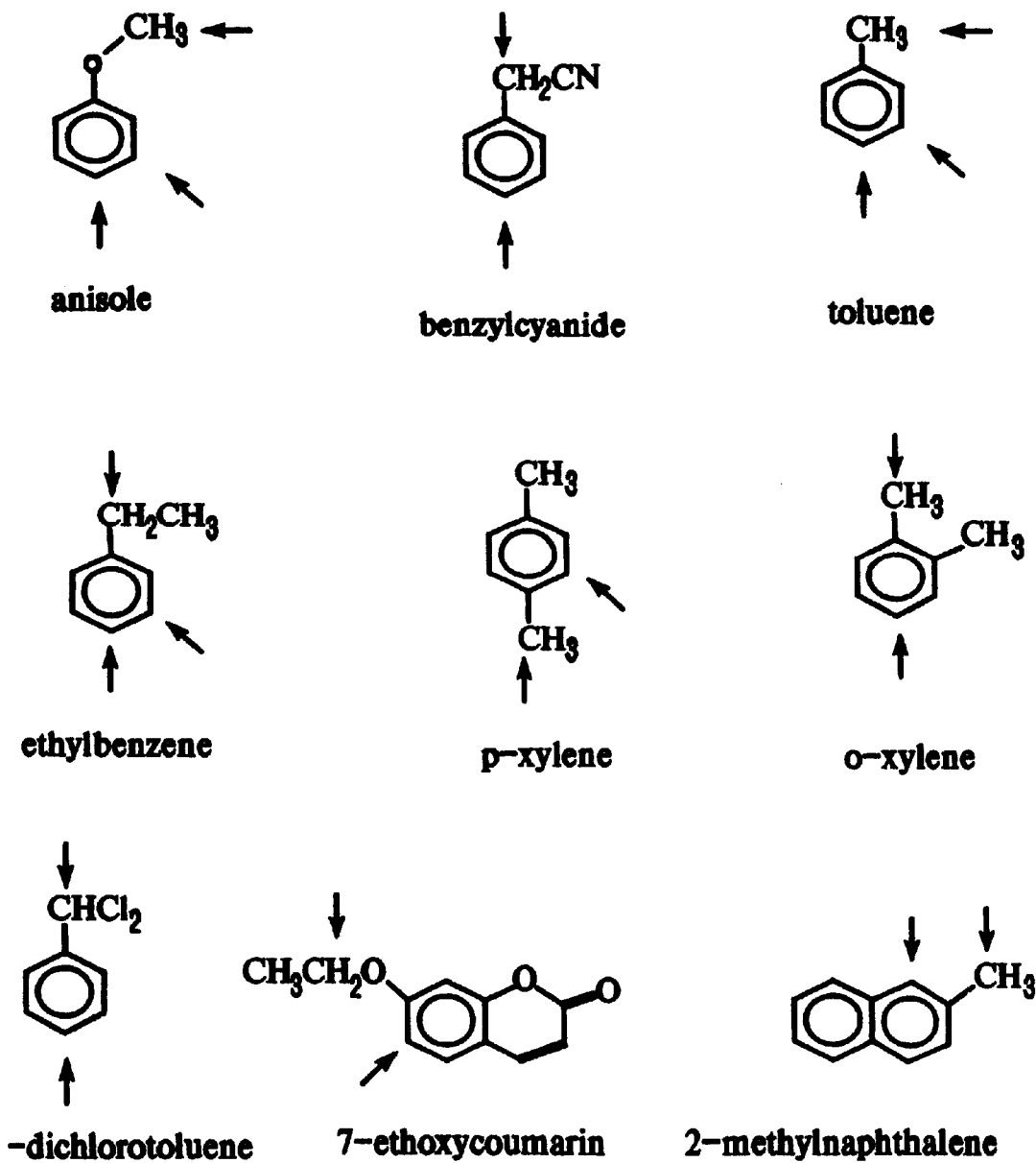
FIG. 13 shows substrates used to parameterize aromatic oxidation.

Experimental metabolite ratios may also be used to parameterize the aromatic oxidation reaction in a theoretical model for CYP reactions. As with hydrogen atom abstraction discussed in the previous Examples, experimental ratios of aromatic oxidation to an alternate position may be determined using various CYP enzymes. An example of substrates that can be used to parameterize aromatic hydroxylation reactions are given in FIG. 13. These substrates were chosen based on their small size, the presence of an alternate position for metabolism, and their hydrophobicity.

In order for the substrates to be useful, the average of the rotation rates in the active sites should be rapid. For five of the substrates, 7-ethoxycoumarin, toluene, o-xylene, p-xylene, and anisole, isotope effect studies have shown that rapid exchange of the relevant positions does occur. The remainder of the substrates cannot form hydrogen bonds. Therefore, hydrophobic interactions are most likely to be involved in binding of these substrates, and rotation is likely to be rapid. Several human expressed CYP enzymes were used in these studies, including CYP1A1, 1A2, 2A6, 2B6, 2C8, 2C9, 2D6, 2E1, 3A4, and 3A5. The use of multiple enzymes insures that a reasonable average of any orientation preferences within the active site (see FIG. 1).

The analysis and construction of a model for both hydrogen abstraction and aromatic oxidation will require a combination of data from both reactions. This is accomplished using Equations 5 and 6 above.

All references cited herein are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A computer implemented method for predicting the regiospecific metabolism of a compound metabolized by one or more enzymes with broad substrate specificity, the method comprising:
   (a) providing one or more equations, each relating one or more quantum chemical descriptors to the activation energy of a metabolic transformation of a functional group on the compound, where the one or more equations (i) do not account for steric interactions of the compound with the one or more enzymes, and (ii) were generated by parameterizing one or more expressions for quantum chemical activation energy with experimental data;
   (b) applying the one or more equations to two or more separate functional groups on the compound to thereby predict an activation energy value associated with the metabolic transformation of each of the two or more separate functional groups; and
   (c) predicting the regiospecific metabolism of the compound based on the activation energy values identified at (b).

2. The method of claim 1, wherein the one or more quantum chemical descriptors include at least one of relative heats of formation, ionization potentials, and spin contamination parameters.

3. The method of claim 1, wherein the metabolic transformations associated with the one or more equations include at least one of a hydrogen atom abstraction and an oxygen addition.

4. The method of claim 1 wherein at least one of the one or more equations relates the activation energy to the heat of reaction of the metabolic transformation of the functional group on the compound.

5. The method of claim 1 wherein said experimental data comprises relative rates of substrate rotation in the active site of the enzyme obtained by determining isotope effect profiles for at least one of the metabolic transformations.

6. The method of claim 1, wherein the one or more equations were further parameterized using ab initio quantum chemical calculations of parameters.

7. The method of claim 6, wherein the one or more equations were parameterized by application of the ab initio quantum chemical calculations to the one or more equations for quantum chemical activation energy, which were formulated using an equation for semiempirical quantum chemical activation energy.

8. The method of claim 1, wherein the one or more enzymes with broad substrate specificity includes a mono oxygenase.

9. The method of claim 8, wherein the mono oxygenase is a cytochrome P-450 enzyme.

10. The method of claim 9, wherein said cytochrome P-450 enzyme is selected from the group consisting of human enzymes CYP2E1, CYP3A4, CYP2B6, CYP2C8, CYP2C9, CYP1A1, CYP1A2, CYP2C19, CYP2D6, CYP1B1, and CYP2A6.

11. The method of claim 1 wherein the functional groups on the compound include at least one of C—R; C—C; C=C; C≡C; C=O; C—N; C=N; —S—; —N—; —N=; —CHO; —OH; and —COR.

12. The method of claim 1, wherein at least one of the one or more equations relates the activation energy associated with a hydrogen atom abstraction at a functional group to
   (i) a heat of reaction for a hydrogen atom abstraction at a functional group and
   (ii) an ionization potential of a radical resulting from the hydrogen atom abstraction.

13. The method of claim 1, wherein the at least one equation is $$\Delta H_{act} = -4.16 + 0.165(\Delta H_R) + 1.78(IP_{rad})$$

where $\Delta H_{act}$ is the activation energy associated with the hydrogen atom abstraction, $\Delta H_R$ is the heat of reaction for the hydrogen atom abstraction, and $IP_{rad}$ is the ionization potential of a radical resulting from the hydrogen atom abstraction.

14. The method of claim 1, wherein at least one of the one or more equations relates the activation energy associated with an aromatic oxidation to
   (i) a heat of reaction for an aromatic oxidation reaction in the substrate, and
   (ii) a correction for UHF spin contamination in an equation based on AM1 calculation.

15. The method of claim 1, wherein the at least one equation is $$\Delta H_{arom} = 15.86 + 0.32(\Delta H_R) + 1.31(\Delta S^2)$$

where $\Delta H_{arom}$ is the heat of reaction for an aromatic oxidation reaction, $\Delta H_R$ is the heat of reaction for the aromatic oxidation, and $\Delta S^2$ is a correction for spin contamination in the equation.

16. The method of claim 1, wherein the one or more quantum chemical descriptors include at least one of relative heat of formation, orbital energy, and spin parameters.

17. The method of claim 1, wherein the one or more equations were generated by parameterizing the one or more expressions for quantum chemical activation energy with experimental data by regression of the experimental data on the quantum chemical descriptors.

18. The method of claim 1, further comprising determining whether metabolism of the compound results in one or more of the following:
   (1) the production of an excess concentration of a toxic metabolite;
   (2) an excessive rate of metabolism of a pharmaceutically useful substance;
   (3) an inadequate rate of metabolism of a pharmaceutically useful substance; and
   (4) an excessive rate of metabolism of a non-pharmaceutically useful substance into a toxic metabolite.

19. The method of claim 1, wherein the one or more equations for quantum chemical activation energy were formulated using an equation for semiempirical quantum chemical activation energy.

20. A computer implemented method for predicting the regiospecific metabolism of a compound metabolized by one or more enzymes with broad substrate specificity, the method comprising:
   (a) providing two or more equations, each relating one or more quantum chemical descriptors to the activation energy of a metabolic transformation of a functional group on the compound, where at least two of the two or more equations (i) do not account for steric interactions of the compound with the one or more enzymes, (ii) were generated by parameterizing one or more expressions for quantum chemical activation energy with experimental data, and (iii) separately predict activation energy for at least a first enzyme-mediated reaction and a second enzyme-mediated reaction;
   (b) applying the two or more equations to two or more separate functional groups on the compound to thereby predict an activation energy value associated with the metabolic transformation of each of the two or more separate functional groups, wherein the metabolic transformation of at least one functional group comprises the first enzyme-mediated reaction and the metabolic transformation of at least one other functional group comprises the second enzyme-mediated reaction; and
   (c) predicting the regiospecific metabolism of the compound based on the activation energy values identified at (b).

21. The method of claim 20, wherein the first enzyme-mediated reaction comprises hydrogen atom abstraction.

22. The method of claim 20, wherein the second enzyme-mediated reaction comprises oxygen addition.

23. The method of claim 20, wherein the first enzyme-mediated reaction comprises hydroxylation.

24. The method of claim 20, wherein the second enzyme-mediated reaction comprises aromatic oxidation.

25. The method of claim 20, wherein the first enzyme-mediated reaction comprises hydrogen atom abstraction, aromatic oxidation, olefinic oxidation, carbonyl metabolism, N-oxidation, or S-oxidation.

26. The method of claim 20, wherein the one or more quantum chemical descriptors for at least one of the two more equations include at least one of relative heats of formation, ionization potentials, and spin contamination parameters.

27. The method of claim 20, wherein the two or more equations were generated by parameterizing the one or more expressions for quantum chemical activation energy with experimental data by regression of the experimental data on the quantum chemical descriptors.

28. The method of claim 20, further comprising determining whether metabolism of the compound results in one or more of the following:
   (1) the production of an excess concentration of a toxic metabolite;
   (2) an excessive rate of metabolism of a pharmaceutically useful substance;
   (3) an inadequate rate of metabolism of a pharmaceutically useful substance; and
   (4) an excessive rate of metabolism of a non-pharmaceutically useful substance into a toxic metabolite.

29. The method of claim 20 wherein at least one of the two or more equations relates the activation energy to the heat of reaction of the metabolic transformation of the functional group on the compound.

30. The method of claim 20, wherein at least one of the two or more equations for quantum chemical activation energy were formulated using an equation for semiempirical quantum chemical activation energy.

31. The method of claim 20 wherein said experimental data comprises relative rates of substrate rotation in the active site of the enzyme obtained by determining isotope effect profiles for at least one of the metabolic transformations.

32. The method of claim 20, wherein the one or more equations were further parameterized using ab initio quantum chemical calculations of parameters.

33. The method of claim 32, wherein the at least one of the two or more equations was parameterized by application of the ab initio quantum chemical calculations to the one or more equations for quantum chemical activation energy, which were formulated using an equation for semiempirical quantum chemical activation energy.

34. The method of claim 20, wherein the one or more enzymes with broad substrate specificity includes a mono oxygenase.

35. The method of claim 34, wherein the mono oxygenase is a cytochrome P-450 enzyme.

36. The method of claim 35, wherein said cytochrome P-450 enzyme is selected from the group consisting of human enzymes CYP2E1, CYP3A4, CYP2B6, CYP2C8, CYP2C9, CYP1A1, CYP1A2, CYP2C19, CYP2D6, CYP1B1, and CYP2A6.

37. The method of claim 20 wherein the functional groups on the compound include at least one of C—R; C—C; C=C; C≡C; C=O; C—N; C=N; —S—; —N—; —N=; —CHO; —OH; and —COR.

38. The method of claim 20, wherein at least one of the two or more equations relates the activation energy associated with a hydrogen atom abstraction at a functional group to
   (i) a heat of reaction for a hydrogen atom abstraction at a functional group and
   (ii) an ionization potential of a radical resulting from the hydrogen atom abstraction.

39. The method of claim 20, wherein at least one of the two or more equations relates the activation energy associated with an aromatic oxidation to
   (i) a heat of reaction for an aromatic oxidation reaction in the substrate, and
   (ii) a correction for UHF spin contamination in an equation based on AM1 calculation.

40. The method of claim 20, wherein the one or more quantum chemical descriptors include at least one of relative heat of formation, orbital energy, and spin parameters.

* * * * *